United States Patent
Park et al.

(10) Patent No.: US 11,380,846 B2
(45) Date of Patent: *Jul. 5, 2022

(54) COMPOUND FOR ORGANIC ELECTRIC ELEMENT, ORGANIC ELECTRIC ELEMENT COMPRISING THE SAME AND ELECTRONIC DEVICE THEREOF

(71) Applicant: DUK SAN NEOLUX CO., LTD., Cheonan-si (KR)

(72) Inventors: Jung Cheol Park, Suwon-si (KR); Yeon Hee Choi, Cheonan-si (KR); Mun Jae Lee, Cheonan-si (KR); Soung Yun Mun, Cheonan-si (KR); Ki Won Kim, Suwon-si (KR); Namjin Park, Cheonan-si (KR); Jung Wook Lee, Gunsan-si (KR)

(73) Assignee: DUK SAN NEOLUX CO., LTD., Cheonan-si (KR)

( * ) Notice: Subject to any disclaimer, the term of this patent is extended or adjusted under 35 U.S.C. 154(b) by 252 days.

This patent is subject to a terminal disclaimer.

(21) Appl. No.: 15/576,989

(22) PCT Filed: May 18, 2016

(86) PCT No.: PCT/KR2016/005273
§ 371 (c)(1),
(2) Date: Nov. 27, 2017

(87) PCT Pub. No.: WO2016/190600
PCT Pub. Date: Dec. 1, 2016

(65) Prior Publication Data
US 2018/0083197 A1   Mar. 22, 2018

(30) Foreign Application Priority Data

May 27, 2015 (KR) .......................... 10-2015-0073550

(51) Int. Cl.
*H01L 51/00* (2006.01)
*C09K 11/06* (2006.01)
*C07D 307/91* (2006.01)
*H01L 51/50* (2006.01)
*C07D 307/77* (2006.01)
(Continued)

(52) U.S. Cl.
CPC ........ *H01L 51/0061* (2013.01); *C07D 307/77* (2013.01); *C07D 307/91* (2013.01); *C07D 409/04* (2013.01); *C07F 7/0812* (2013.01); *C09K 11/06* (2013.01); *H01L 51/006* (2013.01); *H01L 51/0059* (2013.01); *H01L 51/0094* (2013.01); *H01L 51/50* (2013.01); *C09K 2211/1007* (2013.01); *C09K 2211/1011* (2013.01); *C09K 2211/1014* (2013.01); *C09K 2211/1018* (2013.01); *H01L 51/0003* (2013.01); *H01L 51/0004* (2013.01); *H01L 51/0005* (2013.01); *H01L 51/0052* (2013.01); *H01L 51/0058* (2013.01); *H01L 51/0073* (2013.01); *H01L 51/0074* (2013.01); *H01L 51/5012* (2013.01); *H01L 51/5056* (2013.01); *H01L 51/5072* (2013.01); *H01L 51/5088* (2013.01); *H01L 51/5092* (2013.01); *H01L 51/5096* (2013.01)

(58) Field of Classification Search
CPC .. C07D 307/77; C07D 307/91; C07D 409/04; C07F 7/0812; C09K 11/06; C09K 2211/1007; C09K 2211/1011; C09K 2211/1014; C09K 2211/1018; H01L 51/0003; H01L 51/0004; H01L 51/0005; H01L 51/0052; H01L 51/0058; H01L 51/006; H01L 51/0061; H01L 51/0073; H01L 51/0074; H01L 51/0094; H01L 51/50; H01L 51/5012; H01L 51/5056; H01L 51/5072; H01L 51/5088; H01L 51/5092
See application file for complete search history.

(56) References Cited

U.S. PATENT DOCUMENTS

| 9,028,977 B2 | 5/2015 | Bae et al. |
| 9,799,835 B2 | 10/2017 | Kim et al. |
| 2007/0278938 A1 | 12/2007 | Yabunouchi et al. |

(Continued)

FOREIGN PATENT DOCUMENTS

| CA | 102046613 A | 5/2011 |
| CN | 104650029 A | 5/2015 |

(Continued)

OTHER PUBLICATIONS

Non-Final Office Action issued in corresponding application JP2017561706 dated May 7, 2019, 2 pages.

(Continued)

*Primary Examiner* — Dawn L Garrett
(74) *Attorney, Agent, or Firm* — Vorys, Sater, Seymour & Pease LLP; Mih Suhn Koh

(57) ABSTRACT

Provided are a compound represented by Formula 1, and an organic electric element comprising a first electrode, a second electrode, and an organic material layer formed between the first electrode and the second electrode, wherein the organic material layer comprised the compound represented by Formula 1, and the driving voltage of an organic electronic device can be lowered, and the luminous efficiency, color purity and life time of an organic electronic device can be improved by comprising the compound represented by Formula 1 in the organic material layer.

12 Claims, 1 Drawing Sheet

(51) Int. Cl.
*C07D 409/04* (2006.01)
*C07F 7/08* (2006.01)

(56) References Cited

U.S. PATENT DOCUMENTS

| | | | |
|---|---|---|---|
| 2010/0001636 A1* | 1/2010 | Yabunouchi | C07D 307/91 |
| | | | 313/504 |
| 2012/0043531 A1 | 2/2012 | Jung et al. | |
| 2012/0146014 A1* | 6/2012 | Kato | C07D 307/91 |
| | | | 257/40 |
| 2013/0069049 A1* | 3/2013 | Park | C07D 487/04 |
| | | | 257/40 |
| 2014/0034915 A1 | 2/2014 | Lee et al. | |
| 2014/0183500 A1* | 7/2014 | Ikeda | C07D 405/04 |
| | | | 257/40 |
| 2014/0291643 A1 | 10/2014 | Ogita et al. | |
| 2016/0133850 A1* | 5/2016 | Matsuura | H01L 51/0058 |
| | | | 257/40 |
| 2017/0317289 A1* | 11/2017 | Lee | C07D 409/12 |

FOREIGN PATENT DOCUMENTS

| | | |
|---|---|---|
| EP | 2 177 516 A1 | 4/2010 |
| EP | 2 502 908 A1 | 9/2012 |
| EP | 2 816 025 A1 | 12/2014 |
| JP | 2012-503027 A | 2/2012 |
| KR | 10-2008-0061800 A | 7/2008 |
| KR | 10-2014-0017400 A | 2/2014 |
| KR | 10-2014-0057439 A | 5/2014 |
| KR | 10-2014-0102089 A | 8/2014 |
| KR | 10-2014-0123460 A | 10/2014 |
| KR | 10-2015-0016896 A | 2/2015 |
| KR | 1530049 B1 * | 6/2015 |
| KR | 10-2016-0027940 A | 3/2016 |
| KR | 10-2017-0096770 A | 8/2017 |
| WO | 2006/128800 A1 | 12/2006 |
| WO | 2009/145016 A1 | 12/2009 |
| WO | 2011/021520 A1 | 2/2011 |
| WO | 2011/059099 A1 | 5/2011 |
| WO | 2014/077558 A1 | 5/2014 |
| WO | 2014/088047 A1 | 6/2014 |
| WO | 2014/104144 A1 | 7/2014 |
| WO | 2014/142472 A1 | 9/2014 |
| WO | 2014/157574 A1 | 10/2014 |
| WO | 2015/020348 A1 | 2/2015 |
| WO | WO 2016/064110 A1 * | 4/2016 |

OTHER PUBLICATIONS

Japanese Non-Final Office Action, dated Nov. 27, 2018.
Extended European Search Report, dated Mar. 7, 2019, 11 pages.
RN 1627727-20-1 and RN 1627726-89-9, STN REG, Oct. 1, 2014, 2 pages.
Chinese Office Action for corresponding CN Application No. 201680030815.1, dated Apr. 23, 2020, 11 pages.

* cited by examiner

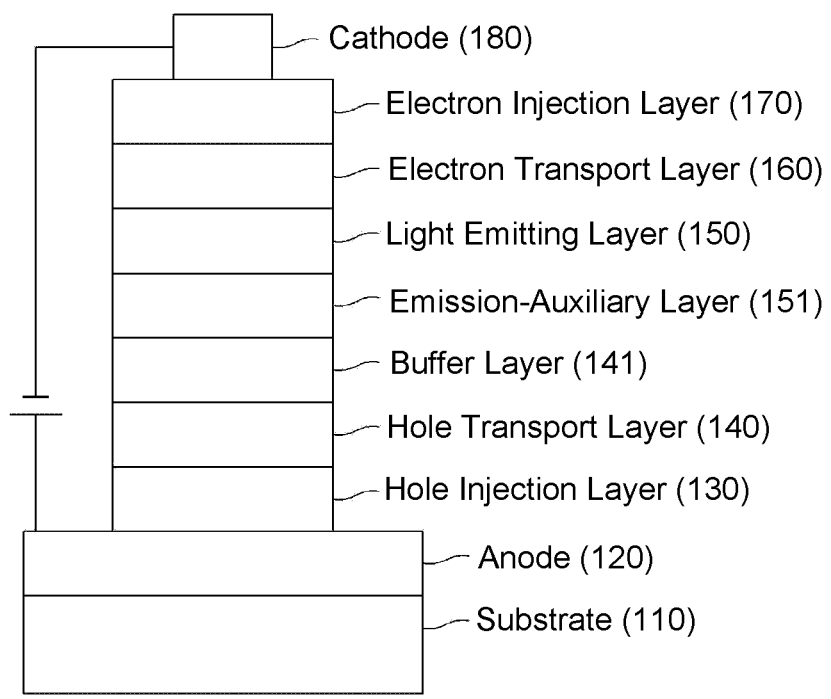

COMPOUND FOR ORGANIC ELECTRIC ELEMENT, ORGANIC ELECTRIC ELEMENT COMPRISING THE SAME AND ELECTRONIC DEVICE THEREOF

CROSS-REFERENCE TO RELATED APPLICATION

This patent application claims priority from and the benefit under 35 U.S.C. 119(a) of Korean Patent Application No. 10-2015-0073550, filed on May 27, 2015, which is hereby incorporated by reference for all purposes as if fully set forth herein. Further, this application claims the benefit of priority in countries other than U.S.A, which is hereby incorporated by reference herein.

BACKGROUND

Technical Field

The present invention relates to compounds for organic electric elements, organic electric elements comprising the same, and electronic devices thereof.

Background Art

In general, an organic light emitting phenomenon refers to a phenomenon in which electric energy is converted into light energy of an organic material. An organic electric element utilizing the organic light emitting phenomenon usually has a structure including an anode, a cathode, and an organic material layer interposed therebetween. In many cases, the organic material layer has a multi-layered structure having respectively different materials in order to improve efficiency and stability of an organic electric element, and for example, may include a hole injection layer, a hole transport layer, a light emitting layer, an electron transport layer, an electron injection layer, or the like.

Materials used as an organic material layer in an organic electric element may be classified into a light emitting material and a charge transport material, for example, a hole injection material, a hole transport material, an electron transport material, an electron injection material, and the like according to its function.

Currently, the power consumption is required more and more as size of display becomes larger and larger in the portable display market. Therefore, the power consumption is a very important factor in the portable display with a limited power source of the battery, and efficiency and life span issue also must be solved.

Efficiency, life span, driving voltage, and the like are correlated with each other. For example, if efficiency is increased, then driving voltage is relatively lowered, and the crystallization of an organic material due to Joule heating generated during operation is reduced as driving voltage is lowered, as a result of which life span shows a tendency to increase. However, efficiency cannot be maximized only by simply improving the organic material layer. This is because long life span and high efficiency can be simultaneously achieved when an optimal combination of energy levels and T1 values, inherent material properties (mobility, interfacial properties, etc.), and the like among the respective layers included in the organic material layer is given.

Further, recently, in order to solve the emission problem in a hole transport layer and driving voltage of an organic electric element, it is needed to form an emission-auxiliary layer (multilayered hole transport layer) between the hole transport layer and a light emitting layer, and it is time to develop different emission-auxiliary layers according to respective light emitting layers.

In general, an electron which is transferred from an electron transport layer to a light emitting layer and a hole which is transferred from a hole transport layer to the light emitting layer are recombined to form an exciton in a light emitting layer.

However, the material used for the hole transport layer has a low HOMO value and therefore has a low T1 value. As a result, the exciton generated in the light emitting layer is transferred to the hole transport layer, resulting in a charge unbalance in the light emitting layer and light is emitted at the interface of the hole transport layer.

When light is emitted at the interface of the hole transport layer, color purity and efficiency of the organic electronic device are lowered and the lifetime is shortened. Therefore, it is strongly desired to develop a light-emitting auxiliary layer material having a HOMO energy level between the HOMO energy level of the hole transport layer and the HOMO energy level of the light emitting layer, a high T1 value and a hole mobility within a proper driving voltage range (within a blue device driving voltage range of a full device).

However, this cannot be achieved simply by the structural properties of the core of an emission-auxiliary layer material. High efficiency and long lifespan of device can be achieved when the characteristics of the core and the sub-substituent and the proper combination of the emission-auxiliary layer and the hole transport layer and of the emission-auxiliary layer and the light-emitting layer are met.

On the other hand, it is required to develop a hole injection/transport layer material that retards penetration/diffusion of metal oxides from an anode electrode (ITO) into an organic layer, which is one cause for the shortened life span of an organic electric element, and has stability against Joule heat generated during the operation of an organic electric element, that is, a high glass transition temperature. Also, it has been reported that a low glass transition temperature of a hole transport layer material has a great effect on the life span of an organic electric element because the uniformity of a thin film surface collapses during the operation of the element. In addition, deposition is a main method of forming an OLED, and thus there is an actual need to develop a material that is durable to such a deposition method, that is, a highly heat-resistant material.

That is, it should be preceded that the materials consisting an organic material layer of the element, for example, a hole injection material, a hole transport material, a light emitting material, an electron transport material, an electron injection material, or the like, are supported by a stable and efficient material. Particularly, it is strongly required to develop materials of the emission-auxiliary layer and the hole transport layer.

SUMMARY

In order to solve one or more of the above-mentioned problems in prior art, an aspect of the present invention is to provide a compound having efficient electron blocking ability and hole transport ability and allowing to improve luminous efficiency, to lower a driving voltage, to have a high heat-resistance, and to improve color purity and lifetime of the element, an organic electric element comprising the same, and an electronic device thereof.

In accordance with an aspect of the present invention, the compound represented by the following formula is provided.

The following formula represents the compound having dibenzofuran fused with an aromatic ring and bonded to the tertiary amine

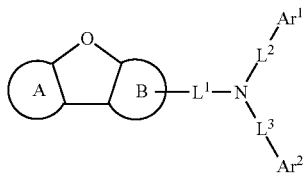

In another aspect of the present invention, organic electric elements comprising the compound represented by the formula above and electronic devices including the organic electric element are provided.

According to the embodiments of the present invention, by using a specific compound having a substituent which enhances the planity of a molecule as a material of the organic electric device, hole transport ability and thermal stability are improved, and the HOMO energy level and the high T1 value are easy to balance the charge in the light emitting layer. As a result, luminous efficiency, heat-resistance, and lifetime of the organic electric elements can be improved and a driving voltage of the organic electric elements can be lowered.

BRIEF DESCRIPTION OF THE DRAWINGS

The FIGURE illustrates an example of an organic light emitting diode according to an embodiment of the present invention.

DETAILED DESCRIPTION

Hereinafter, some embodiments of the present invention will be described in detail with reference to the accompanying illustrative drawings.

In designation of reference numerals to components in respective drawings, it should be noted that the same elements will be designated by the same reference numerals although they are shown in different drawings. Further, in the following description of the present invention, a detailed description of known functions and configurations incorporated herein will be omitted when it may make the subject matter of the present invention rather unclear.

In addition, terms, such as first, second, A, B, (a), (b) or the like may be used herein when describing components of the present invention. Each of these terminologies is not used for defining an essence, order or sequence of a corresponding component but used merely to distinguish the corresponding component from other component(s). It should be noted that if it is described in the specification that one component is "connected," "coupled" or "joined" to another component, a third component may be "connected," "coupled," and "joined" between the first and second components, although the first component may be directly connected, coupled or joined to the second component.

In addition, it will be understood that when an element such as a layer, film, region or substrate is referred to as being "on" or "over" another element, it can be directly on the other element or intervening elements may also be present. In contrast, when an element is referred to as being "directly on" another element, there are no intervening elements present.

As used in the specification and the accompanying claims, unless otherwise stated, the following is the meaning of the term as follows.

Unless otherwise stated, the term "halo" or "halogen" as used herein includes fluorine (F), chlorine (Cl), bromine (Br), or iodine (I).

Unless otherwise stated, the term "alkyl" or "alkyl group" as used herein has a single bond of 1 to 60 carbon atoms, and means aliphatic functional radicals including a linear alkyl group, a branched chain alkyl group, a cycloalkyl group (alicyclic), or an alkyl group substituted with a cycloalkyl.

Unless otherwise stated, the term "halo alkyl" or "halogen alkyl" as used herein includes an alkyl group substituted with a halogen.

Unless otherwise stated, the term "alkenyl" or "alkynyl" as used herein has, but not limited to, double or triple bonds of 2 to 60 carbon atoms, and includes a linear alkyl group, or a branched chain alkyl group.

Unless otherwise stated, the term "cycloalkyl" as used herein means, but not limited to, alkyl forming a ring having 3 to 60 carbon atoms.

The term "alkoxyl group", "alkoxy group" or "alkyloxy group" as used herein means an oxygen radical attached to an alkyl group, but not limited to, and has 1 to 60 carbon atoms.

The term "aryloxyl group" or "aryloxy group" as used herein means an oxygen radical attached to an aryl group, but not limited to, and has 6 to 60 carbon atoms.

Unless otherwise stated, the term "fluorenyl group" or "fluorenylene group" as used herein means, univalent or bivalent functional group which R, R' and R'' are all hydrogen in the structural formula below, "substituted fluorenyl group" or "substituted fluorenylene group" means, functional group which at least any one of R, R' and R'' is a functional group other than hydrogen, and fluorenyl group" or "fluorenylene group" comprises spiro compound which is formed by linking R and R' together with the carbon bonded to them.

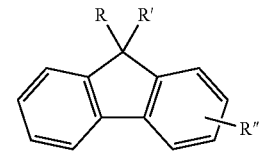

Unless otherwise stated, the term "aryl group" or "arylene group" as used herein has, but not limited to, 6 to 60 carbon atoms. The aryl group or arylene group include a monocyclic rings, ring assemblies, fused polycyclic system or spiro compounds.

Unless otherwise stated, the term "heterocyclic group" as used herein means, but not limited to, a non-aromatic ring as well as an aromatic ring like "heteroaryl group" or "heteroarylene group". The heterocyclic group as used herein means, but not limited to, a ring containing one or more heteroatoms, and having 2 to 60 carbon atoms. Unless otherwise stated, the term "heteroatom" as used herein represents at least one of N, O, S, P, and Si. The heterocyclic group means a monocyclic, ring assemblies, fused polycyclic system or spiro compound containing one or more heteroatoms.

Also, the term "heterocyclic group" may include $SO_2$ instead of carbon consisting of cycle. For example, "heterocyclic group" includes compound below.

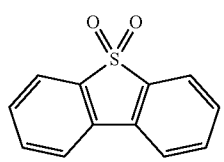 [SMILES: O=S1(=O)c2ccccc2-c2ccccc21]

Unless otherwise stated, the term "ring" as used herein means, a monocyclic and polycyclic, an aliphatic ring and heterocyclic group containing at least one heteroatom, and an aromatic ring and a non-aromatic ring.

Unless otherwise stated, the term "polycyclic" as used herein means, ring assemblies like biphenyl and terphenyl, fused polycyclic system and spiro compound, an aromatic ring and a non-aromatic ring, and an aliphatic ring and heterocyclic group containing at least one heteroatom.

Unless otherwise stated, the term "ring assemblies" as used herein means, two or more cyclic systems (single rings or fused systems) which are directly joined to each other by double or single bonds are named ring assemblies when the number of such direct ring junctions is one less than the number of cyclic systems involved. The ring assemblies also mean, same or different ring systems are directly joined to each other by double or single bonds.

Unless otherwise stated, the term "fused polycyclic system" as used herein means, fused ring type which has at least two atoms as the common members, fused two or more aliphatic ring systems and a fuesd hetero ring system containing at least one heteroatom. Fused polycyclic system is an aromatic ring, a hetero aromatic ring, an aliphatic ring, or the combination of these.

Unless otherwise stated, the term "spiro compound" as used herein has, a spiro union which means union having one atom as the only common member of two rings. The common atom is designated as 'spiro atom'. The compounds are defined as 'monospiro-', 'dispiro-' or 'trispiro-' depending on the number of spiro atoms in one compound.

Also, when prefixes are named subsequently, it means that substituents are listed in the order described first. For example, an arylalkoxy means an alkoxy substituted with an aryl, an alkoxylcarbonyl means a carbonyl substituted with an alkoxyl, and an arylcarbonylalkenyl also means an alkenyl substitutes with an arylcarbonyl, wherein the arylcarbonyl may be a carbonyl substituted with an aryl.

Unless otherwise stated, the term "substituted or unsubstituted" as used herein means that substitution is carried out by at least one substituent selected from the group consisting of, but not limited to, deuterium, halogen, an amino group, a nitrile group, a nitro group, a $C_1$-$C_{20}$ alkyl group, a $C_1$-$C_{20}$ alkoxy group, a $C_1$-$C_{20}$ alkylamine group, a $C_1$-$C_{20}$ alkylthio group, a $C_6$-$C_{20}$ arylthio group, a $C_2$-$C_{20}$ alkenyl group, a $C_2$-$C_{20}$ alkynyl group, a $C_3$-$C_{20}$ cycloalkyl group, a $C_6$-$C_{60}$ aryl group, a $C_6$-$C_{20}$ aryl group substituted by deuterium, a fluorenyl group, a $C_8$-$C_{20}$ arylalkenyl group, a silane group, a boron group, a germanium group, and a $C_2$-$C_{20}$ heterocyclic group containing at least one heteroatom selected from the group consisting of O, N, S, Si, and P.

In the present description, a 'group name' corresponding to an aryl group, an arylene group, a heterocyclic group, and the like exemplified for each symbol and its substituent may be written in the name of functional group reflecting the valence, and may also be described under the name of a parent compound. For example, in the case of phenanthrene, which is a kind of aryl group, it may be described by distinguishing valence such as 'phenanthryl (group)' when it is 'monovalent group', and as 'phenanthrylene (group)' when it is 'divalent group', and it may also be described as a parent compound name, 'phenanthrene', regardless of its valence. Similarly, in the case of pyrimidine, it may be described as 'pyrimidine' regardless of its valence, and it may also be described as the name of corresponding functional group such as pyrimidinyl (group) when it is 'monovalent group', and as 'pyrimidylene (group)' when it is 'divalent group'.

Otherwise specified, the formulas used in the present invention are as defined in the index definition of the substituent of the following formula.

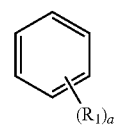

Wherein, when a is an integer of zero, the substituent $R^1$ is absent, when a is an integer of 1, the sole $R^1$ is linked to any one of the carbon atoms constituting the benzene ring, when a is an integer of 2 or 3, the substituent $R^1$s may be the same and different, and are linked to the benzene ring as follows. when a is an integer of 4 to 6, the substituents $R^1$s may be the same and different, and are linked to the benzene ring in a similar manner to that when a is an integer of 2 or 3, hydrogen atoms linked to carbon constituents of the benzene ring being not represented as usual.

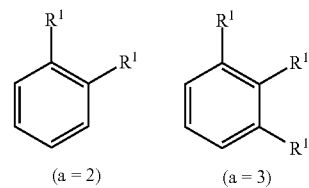

The FIGURE illustrates an organic electric element according to an embodiment of the present invention.

Referring to the FIGURE, an organic electric element 100 according to an embodiment of the present invention includes a first electrode 120 formed on a substrate 110, a second electrode 180, and an organic material layer between the first electrode 110 and the second electrode 180, which contains the inventive compound. Here, the first electrode 120 may be an anode (positive electrode), and the second electrode 180 may be a cathode (negative electrode). In the case of an inverted organic electric element, the first electrode may be a cathode, and the second electrode may be an anode.

The organic material layer may include a hole injection layer 130, a hole transport layer 140, a light emitting layer 150, an electron transport layer 160, and an electron injection layer 170 formed in sequence on the first electrode 120. Here, at least one layer of the organic material layer may be omitted, the organic material layer may further include a hole blocking layer, an electron blocking layer, an emission-auxiliary layer 151, an electron transport auxiliary layer, a buffer layer 141, etc., and the electron transport layer 160 or the like may serve as the hole blocking layer.

Although not shown, the organic electric element according to an embodiment of the present invention may further include at least one protective layer or one capping layer formed on at least one of the sides the first and second electrodes, which is a side opposite to the organic material layer.

The inventive compound employed in the organic material layer may be used as a material of a hole injection layer 130, a hole transport layer 140, an electron transport layer 160, an electron transport auxiliary layer, as a host or a dopant material of a light emitting layer 150, or as a material a capping layer material. For example, the inventive compound may be used as material of the light emitting layer 150, the hole transport layer 140, and/or the emission-auxiliary layer 151, preferably, as the hole transport layer 140, and/or the emission-auxiliary layer 151.

On the other hand, even if the core is the same core, the band gap, the electrical characteristics, the interface characteristics, and the like may be different depending on which substituent is bonded at which position. Therefore, it is necessary to study the selection of the core and the combination of the sub-substituent. Specially, long life span and high efficiency can be simultaneously achieved when the optimal combination of energy levels and T1 values, inherent material properties (mobility, interfacial properties, etc.), and the like among the respective layers of an organic material layer is achieved.

As already described above, generally, in order to solve the emission problem with a hole transport layer of an organic electric element, it is preferable that an emission-auxiliary layer is formed between the hole transport layer and a light emitting layer, and it is necessary to develop different emission-auxiliary layers according to respective light emitting layers (R, G, B).

On the other hand, it is very difficult to infer the characteristics of an emission-auxiliary layer, even if the core of an emission-auxiliary layer is similar, because it is necessary to grasp the correlation between the emission-auxiliary layer and a hole transport layer and a light emitting layer (host).

According to the present invention, energy levels and $T_1$ values between organic material layers, inherent material properties (mobility, interfacial properties, etc.), and the like can be optimized by forming a hole transport layer and/or an emission-auxiliary layer which comprise the compound represented by the Formula 1, and thus it is possible to simultaneously improve the life span and efficiency of the organic electronic element.

The organic electric element according to an embodiment of the present invention may be manufactured using various deposition methods. The organic electric element according to an embodiment of the present invention may be manufactured using a PVD (physical vapor deposition) method or CVD (chemical vapor deposition) method. For example, the organic electric element may be manufactured by depositing a metal, a conductive metal oxide, or a mixture thereof on the substrate to form the anode 120, forming the organic material layer including the hole injection layer 130, the hole transport layer 140, the light emitting layer 150, the electron transport layer 160, and the electron injection layer 170 thereon, and then depositing a material, which can be used as the cathode 180, thereon. Also, an emitting auxiliary layer 151 may be formed between a hole transport layer 140 and a light emitting layer 150, and an electron transport auxiliary layer may be formed between a light emitting layer 150 and an electron transport layer 160.

And also, the organic material layer may be manufactured in such a manner that a smaller number of layers are formed using various polymer materials by a soluble process or solvent process, for example, spin coating, nozzle printing, inkjet printing, slot coating, dip coating, roll-to-roll, doctor blading, screen printing, or thermal transfer, instead of deposition. Since the organic material layer according to the present invention may be formed in various ways, the scope of protection of the present invention is not limited by a method of forming the organic material layer.

The organic electric element according to an embodiment of the present invention may be of a top emission type, a bottom emission type, or a dual emission type depending on the material used.

A WOLED (White Organic Light Emitting Device) readily allows for the formation of ultra-high definition images, and is of excellent processability as well as enjoying the advantage of WOLED (White Organic Light Emitting Device) has advantages of high resolution realization, an excellent processability, and being produced by using conventional color filter technologies for LCDs. Various structures for WOLED which mainly used as back light units have been suggested and patented. WOLED may employ various arrangement methods, representatively, a parallel side-by-side arrangement method of R (Red), G (Green), B (Blue) light-emitting units, a vertical stack arrangement method of RGB light-emitting units, and a CCM (color conversion material) method in which electroluminescence from a blue (B) organic light emitting layer, and the present invention may be applied to such WOLED.

Also, the organic electric element according to an embodiment of the present invention may be any one of an organic light emitting diode, an organic solar cell, an organic photo conductor, an organic transistor, and an element for monochromatic or white illumination.

Another embodiment of the present invention provides an electronic device including a display device which includes the above described organic electric element, and a control unit for controlling the display device. Here, the electronic device may be a wired/wireless communication terminal which is currently used or will be used in the future, and covers all kinds of electronic devices including a mobile communication terminal such as a cellular phone, a personal digital assistant (PDA), an electronic dictionary, a point-to-multipoint (PMP), a remote controller, a navigation unit, a game player, various kinds of TVs, and various kinds of computers.

Hereinafter, an organic electric element according to an aspect of the present invention will be described.

The compound according to an aspect of the present invention is represented by the following Formula 1.

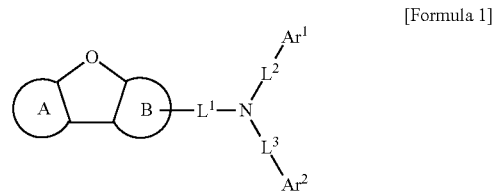

[Formula 1]

In formula 1 above, each of symbols may be defined as follows.

A ring and B ring may be each independently a $C_6$-$C_{10}$ aryl group, A ring may be optionally substituted with at least one of $R^1$, B ring may be optionally substituted with at least one of $R^2$, and the case where A ring and B ring are simultaneously $C_6$ aryl groups may be excluded.

Preferably, A ring and B ring may be each independently a $C_6$ or $C_{10}$ aryl group, more preferably, may be phenyl or naphthyl, but the case where A ring and B ring are simultaneously phenyl is excluded.

$R^1$ and $R^2$ may be each independently selected from the group consisting of deuterium, tritium, halogen, a cyano group, a nitro group, a $C_6$-$C_{60}$ aryl group, a fluorenyl group, a $C_2$-$C_{60}$ heterocyclic group containing at least one heteroatom selected from the group consisting of O, N, S, Si, and P, a fused ring group of a $C_3$-$C_{60}$ aliphatic ring and a $C_6$-$C_{60}$ aromatic ring, a $C_1$-$C_{50}$ alkyl group, a $C_2$-$C_{20}$ alkenyl group, a $C_2$-$C_{20}$ alkynyl group, a $C_1$-$C_{30}$ alkoxyl group, and a $C_6$-$C_{30}$ aryloxyl group.

When $R^1$ and $R^2$ are each the aryl group, fluorenyl group, heterocyclic group, fused ring group, alkyl group, alkenyl group, alkynyl group, alkoxyl group, or aryloxy group, they may be each optionally further substituted with one or more substituents selected from the group consisting of deuterium, halogen, a silane group substituted or unsubstituted with a $C_1$-$C_{20}$ alkyl group or a $C_6$-$C_{20}$ aryl group, a siloxane group, a boron group, a germanium group, a cyano group, a nitro group, a $C_1$-$C_{20}$ alkylthio group, a $C_1$-$C_{20}$ alkoxyl group, a $C_1$-$C_{20}$ alkyl group, a $C_2$-$C_{20}$ alkenyl group, a $C_2$-$C_{20}$ alkynyl group, a $C_6$-$C_{20}$ aryl group, a $C_6$-$C_{20}$ aryl group substituted with deuterium, a fluorenyl group, a $C_2$-$C_{20}$ heterocyclic group containing at least one heteroatom selected from the group consisting of O, N, S, Si, and P, a $C_3$-$C_{20}$ cycloalkyl group, a $C_7$-$C_{20}$ arylalkyl group, and a $C_8$-$C_{20}$ arylalkenyl group.

When $R^1$ and $R^2$ are each the aryl group, they may be preferably $C_6$-$C_{30}$ aryl group, more preferably $C_6$-$C_{10}$ aryl group; when $R^1$ and $R^2$ are each a heterocyclic group group, they may be preferably a $C_2$-$C_{30}$ heterocyclic group group, more preferably $C_2$-$C_{13}$ heterocyclic group group; when $R^1$ and $R^2$ are each a fused ring group, they may be preferably a fused ring group of a $C_3$-$C_{30}$ aliphatic ring and a $C_6$-$C_{30}$ aromatic ring, more preferably a fused ring group of a $C_3$-$C_6$ aliphatic ring and a $C_6$-$C_{10}$ aromatic ring; when $R^1$ and $R^2$ are each a an alkyl group, they may be preferably $C_1$-$C_{10}$ alkyl group, more preferably $C_1$-$C_4$ alkyl group; when $R^1$ and $R^2$ are each a an alkenyl group, they may be preferably $C_1$-$C_{10}$ alkenyl group, more preferably $C_1$-$C_4$ alkenyl group. For example, $R^1$ and $R^2$ may be each independently a cyano group, methyl, tert-butyl, ethenyl, phenyl, naphthyl, benzothienyl, dibenzofuryl, benzoisoquinolyl, or benzocyclobuthenyl and the like, they may be each optionally further substituted with deuterium.

$L^1$ may be $C_6$-$C_{60}$ arylene group.

The arylene group of $L^1$ may be optionally further substituted with one or more substituents selected from the group consisting of deuterium, halogen, a silane group substituted or unsubstituted with a $C_1$-$C_{20}$ alkyl group or a $C_6$-$C_{20}$ aryl group, a siloxane group, a boron group, a germanium group, a cyano group, a nitro group, a $C_1$-$C_{20}$ alkylthio group, a $C_1$-$C_{20}$ alkoxyl group, a $C_1$-$C_{20}$ alkyl group, a $C_2$-$C_{20}$ alkenyl group, a $C_2$-$C_{20}$ alkynyl group, a $C_6$-$C_{20}$ aryl group, a $C_6$-$C_{20}$ aryl group substituted with deuterium, a fluorenyl group, a $C_2$-$C_{20}$ heterocyclic group containing at least one heteroatom selected from the group consisting of O, N, S, Si, and P, a $C_3$-$C_{20}$ cycloalkyl group, a $C_7$-$C_{20}$ arylalkyl group, and a $C_2$-$C_{20}$ arylalkenyl group.

The arylene group of $L^1$ may be preferably a $C_6$-$C_{30}$ arylene group, more preferably $C_6$-$C_{16}$ arylene group. For example, $L^1$ may be phenylene, naphthylene, biphenyl, phenanthrylene or a combination thereof, and the like, and they may be optionally further substituted with deuterium, methyl or naphthyl.

$L^2$ and $L^3$ may be each independently a single bond or a $C_6$-$C_{60}$ arylene group.

The arylene group of $L^2$ and $L^3$ may be optionally further substituted with one or more substituents selected from the group consisting of deuterium, halogen, a silane group substituted or unsubstituted with a $C_1$-$C_{20}$ alkyl group or a $C_6$-$C_{20}$ aryl group, a siloxane group, a boron group, a germanium group, a cyano group, a nitro group, a $C_1$-$C_{20}$ alkylthio group, a $C_1$-$C_{20}$ alkoxyl group, a $C_1$-$C_{20}$ alkyl group, a $C_2$-$C_{20}$ alkenyl group, a $C_2$-$C_{20}$ alkynyl group, a $C_3$-$C_{20}$ cycloalkyl group, a $C_7$-$C_{20}$ arylalkyl group, and a $C_8$-$C_{20}$ arylalkenyl group.

When $L^2$ and $L^3$ are an arylene group, they may be preferably a $C_6$-$C_{30}$ arylene group, more preferably $C_6$-$C_{10}$ arylene group. For example, $L^2$ and $L^3$ may be each independently single bond, phenylene or naphthylene, and the like, and they may be optionally further substituted with deuterium.

$Ar^1$ and $Ar^2$ may be each independently a $C_6$-$C_{60}$ aryl group.

The aryl group of $Ar^1$ and $Ar^2$ may be optionally further substituted with one or more substituents selected from the group consisting of deuterium, halogen, a silane group substituted or unsubstituted with a $C_1$-$C_{20}$ alkyl group or a $C_6$-$C_{20}$ aryl group, a siloxane group, a boron group, a germanium group, a cyano group, a nitro group, a $C_1$-$C_{20}$ alkylthio group, a $C_1$-$C_{20}$ alkoxyl group, a $C_1$-$C_{20}$ alkyl group, a $C_2$-$C_{20}$ alkenyl group, a $C_2$-$C_{20}$ alkynyl group, a $C_6$-$C_{20}$ aryl group substituted with deuterium, a fluorenyl group, a $C_3$-$C_{20}$ cycloalkyl group, a $C_7$-$C_{20}$ arylalkyl group, and a $C_8$-$C_{20}$ arylalkenyl group, and when these substituents are adjacent, they are linked each other to form a ring.

The aryl group of $Ar^1$ and $Ar^2$ may be preferably $C_6$-$C_{30}$ aryl group, more preferably $C_6$-$C_{18}$ aryl group. For example, $Ar^1$ and $Ar^2$ may be each independently phenyl, naphthyl, biphenyl, phenanthryl, fluoranthene, triphenylene, and the like, and they may be optionally further substituted with deuterium, fluoro, ethenyl, methoxy, triphenylsilane or trimethylsilane.

Here, the compound represented by formula

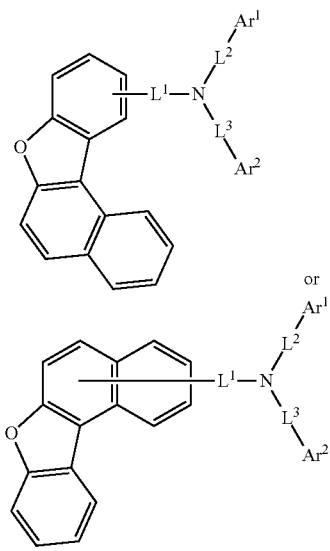

is excluded from the compound represented by formula 1, and $Ar^1$, $Ar^2$ and $L^1$ to $L^3$ are the same as defined in formula 1.

The Formula 1 may be represented by any one of the following Formulas 2 to 9.

<Formula 2>

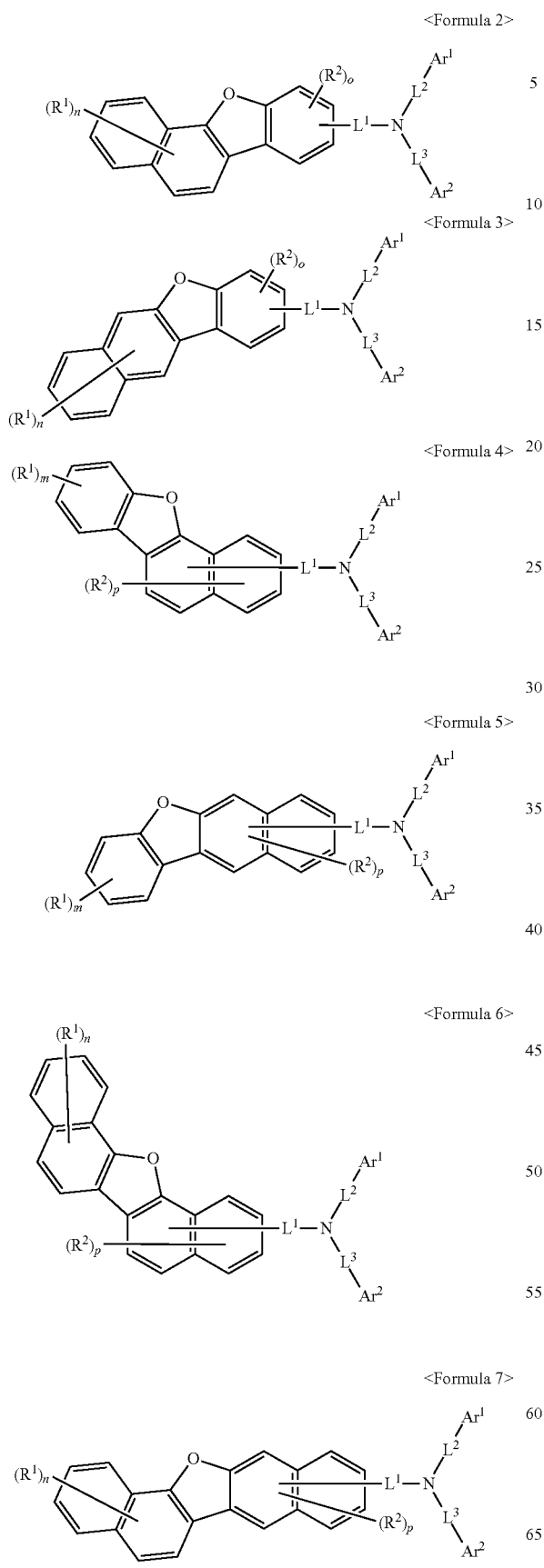

<Formula 3>

<Formula 4>

<Formula 5>

<Formula 6>

<Formula 7>

<Formula 8>

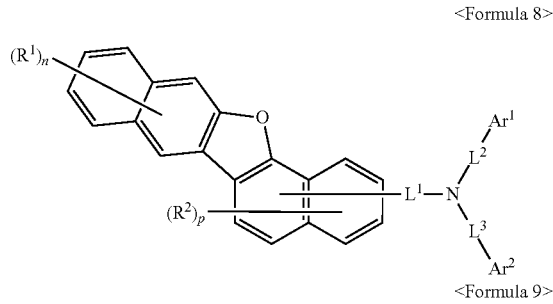

<Formula 9>

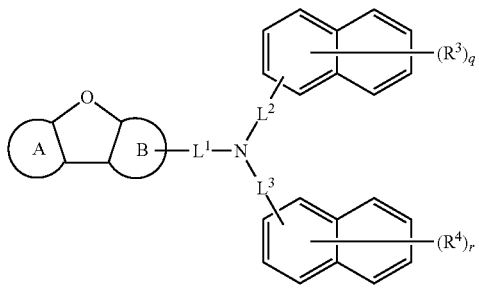

In Formulas 2 to 9, $R^1$, $R^2$, $L^1$ to $L^3$, $Ar^1$ and $Ar^2$ are the same as defined in Formula 1, m is an integer of 0 to 4, n is an integer of 0 to 6, o is an integer of 0 to 3, p is an integer of 0 to 5, and a plurality of $R^1$ and $R^2$ are each the same or different from each other when m, n, o and p are each an integer of 2 or more.

Also, the Formula 1 may be represented by any one of the following Formula 10 or 11.

<Formula 10>

<Formula 11>

In Formulas 10 and 11, A ring and B ring are the same as defined in Formula 1.

$L^1$ may be $C_6$-$C_{30}$ arylene group, $L^2$ and $L^3$ may be each independently a single bond or a $C_6$-$C_{30}$ arylene group, $Ar^2$ may be a $C_6$-$C_{30}$ aryl group.

$R^3$ and $R^4$ are each independently selected from the group consisting of deuterium, halogen, a silane group substituted or unsubstituted with a $C_1$-$C_{20}$ alkyl group or a $C_6$-$C_{20}$ aryl group, a siloxane group, a boron group, a germanium group, a cyano group, a nitro group, a $C_1$-$C_{20}$ alkylthio group, a $C_1$-$C_{20}$ alkoxyl group, a $C_1$-$C_{20}$ alkyl group, a $C_2$-$C_{20}$ alkenyl group, a $C_2$-$C_{20}$ alkynyl group, a $C_6$-$C_{20}$ aryl group substituted with deuterium, a fluorenyl group, a $C_7$-$C_{20}$ arylalkyl group, and a $C_8$-$C_{20}$ arylalkenyl group, q and r are each independently an integer of 0 to 7, and a plurality of $R^3$ and $R^4$ are each the same or different from each other when q and r are each an integer of 2 or more.

Specifically, the compound represented by Formula 1 may be any one of the following compounds.

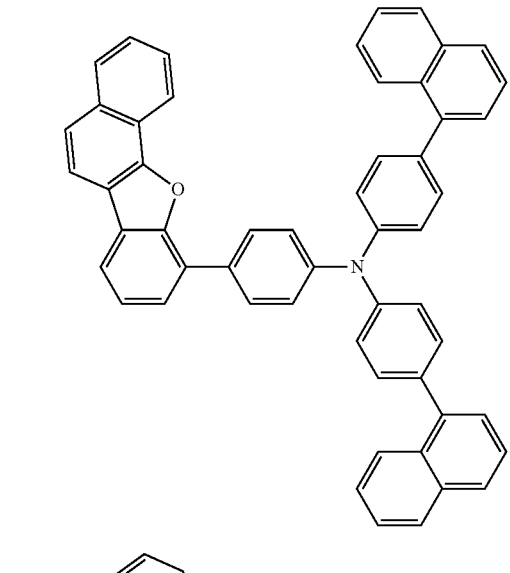

P-1

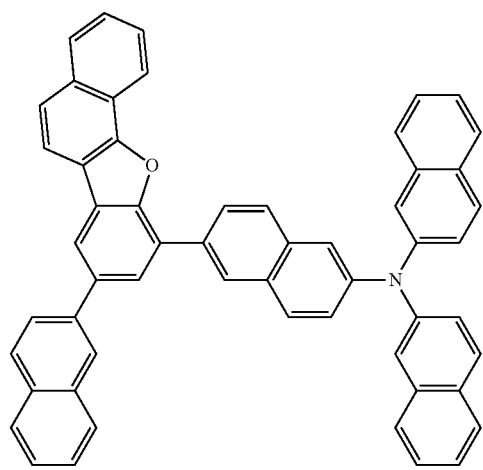

P-2

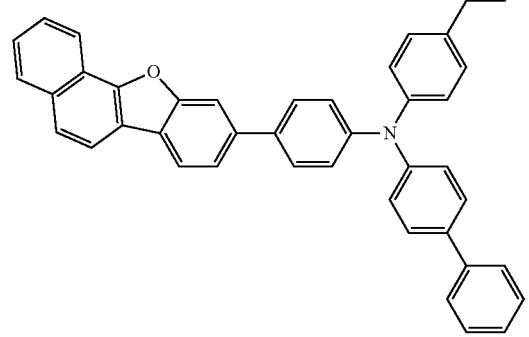

P-3

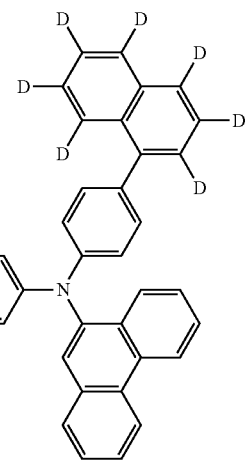

P-4

P-5

P-6

P-7
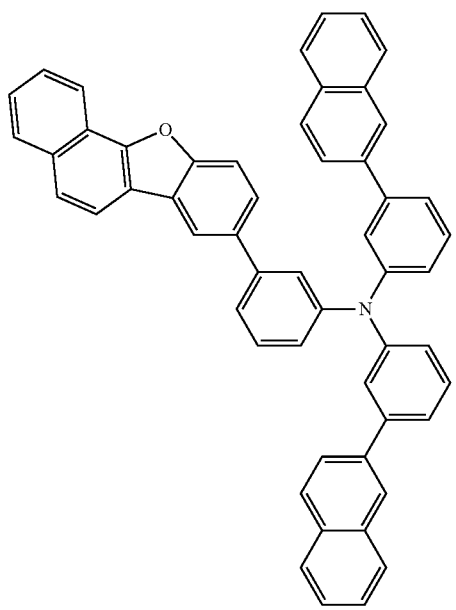
P-8
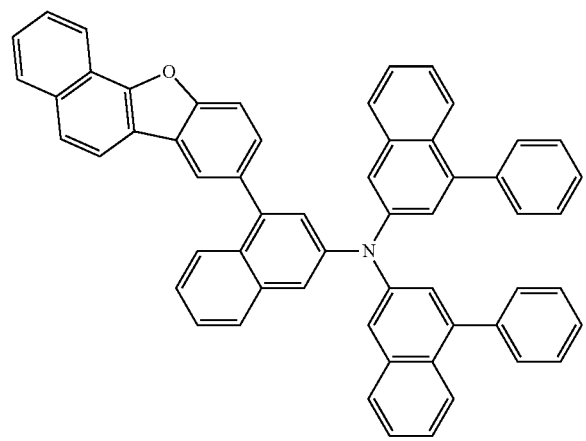
P-9
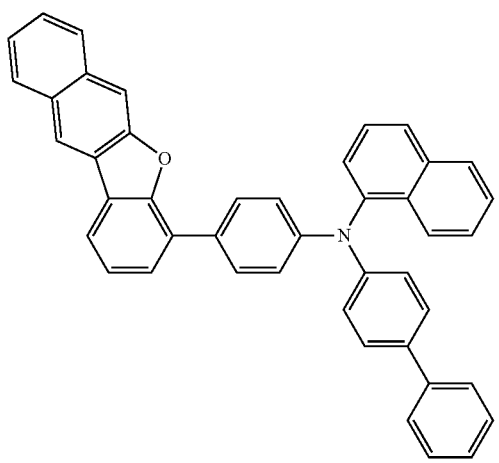
P-10
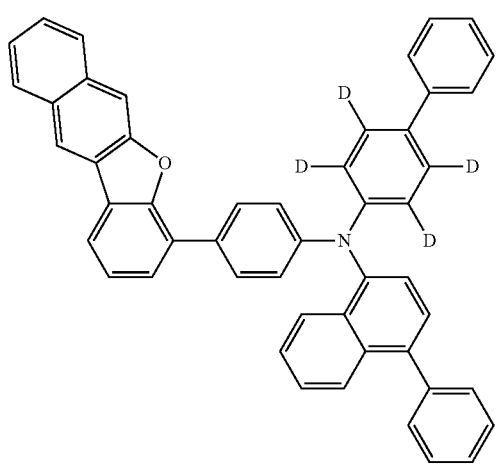
P-11
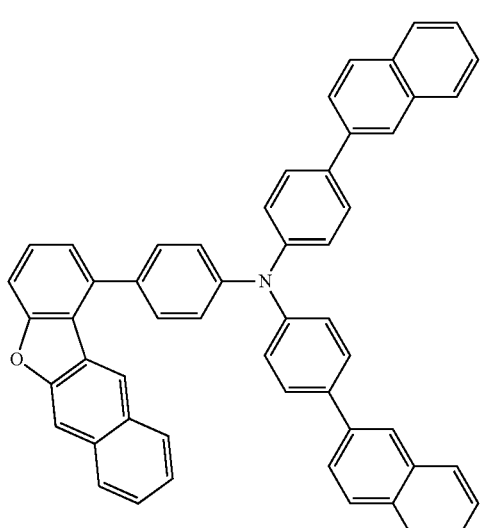
P-12
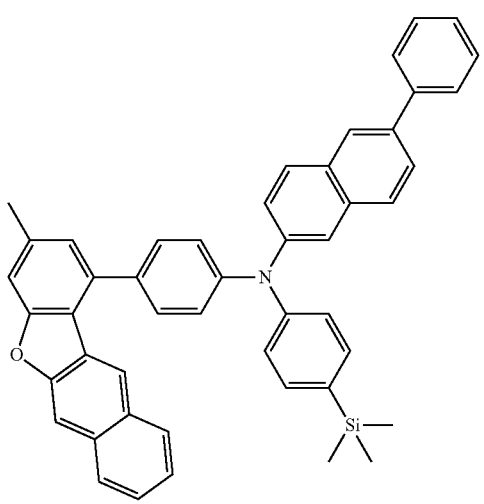

P-13
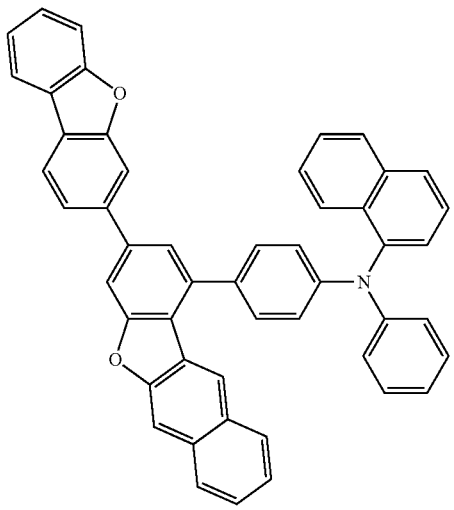
P-14
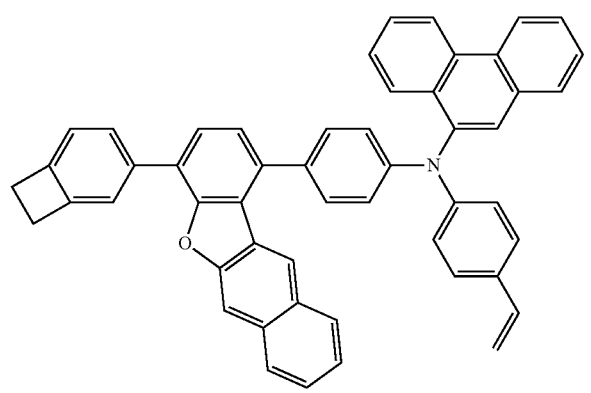
P-15
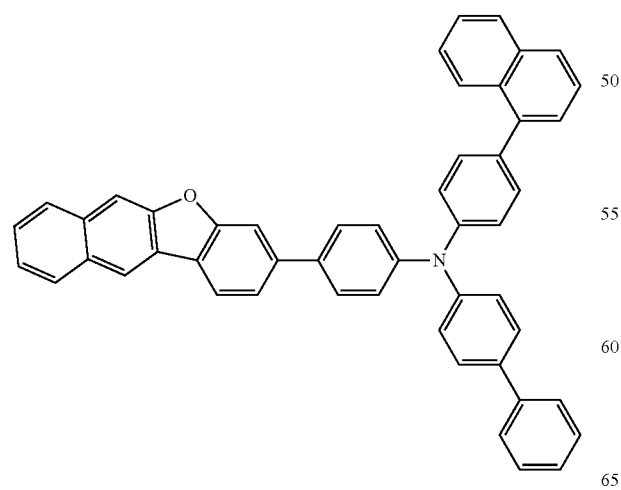
P-16
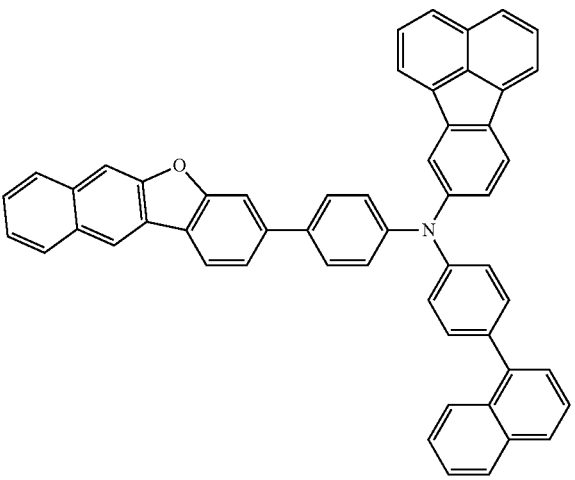
P-17
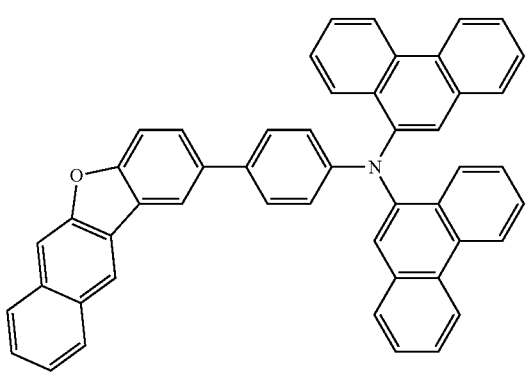
P-18
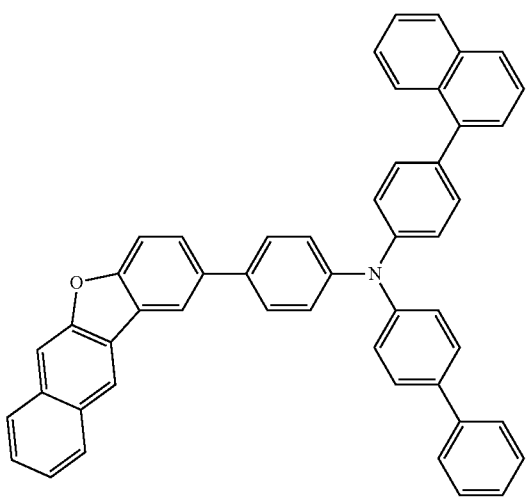

P-19
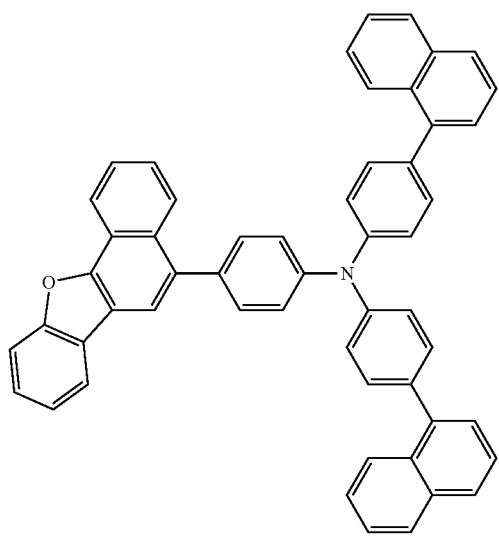
P-22
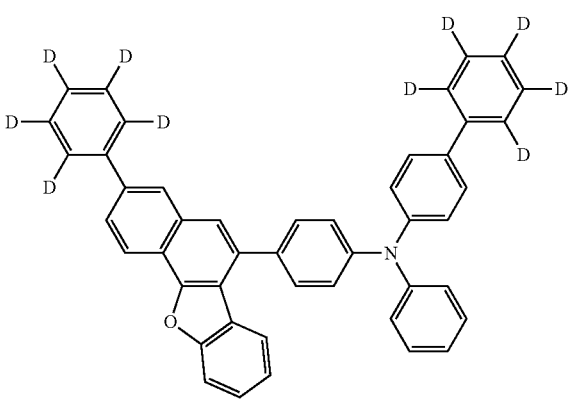
P-20
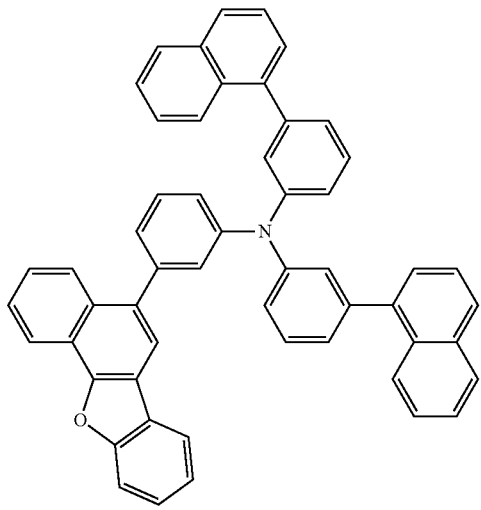
P-23
P-21
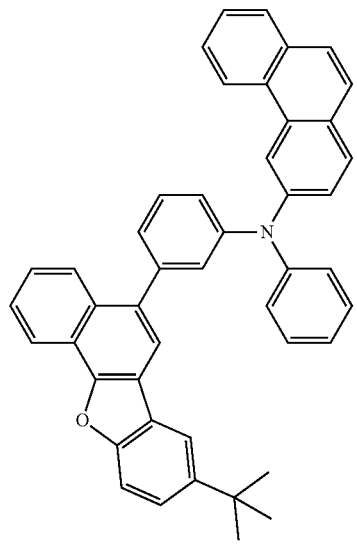
P-24
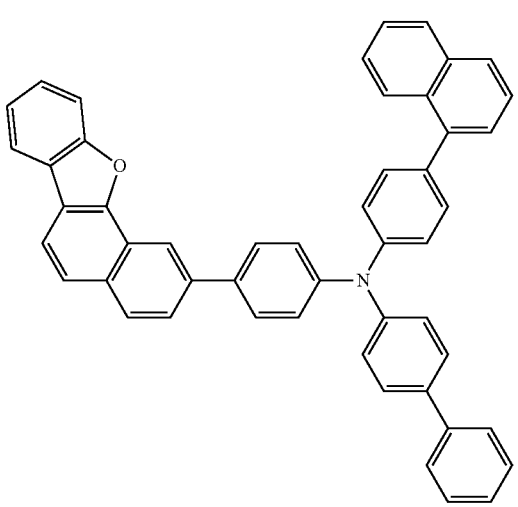

P-25
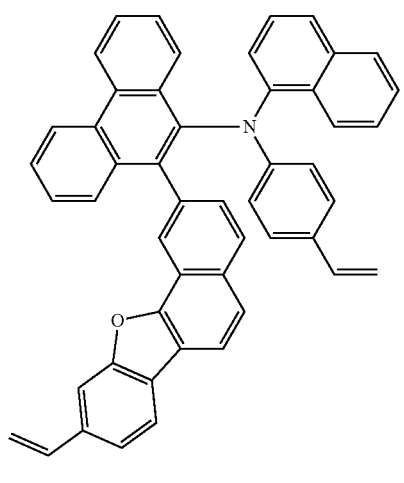
P-26
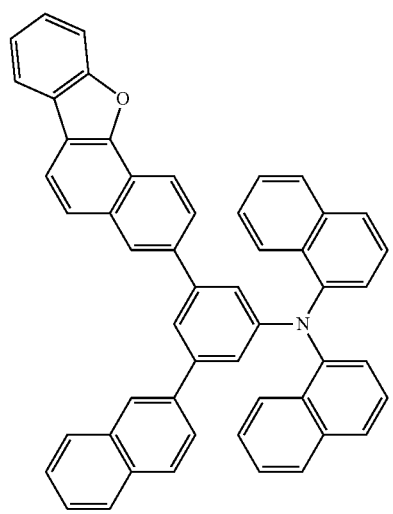
P-27
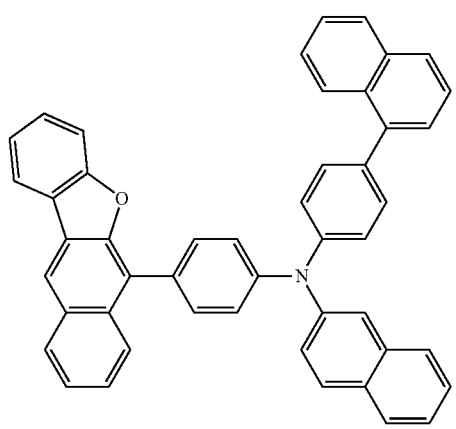
P-28
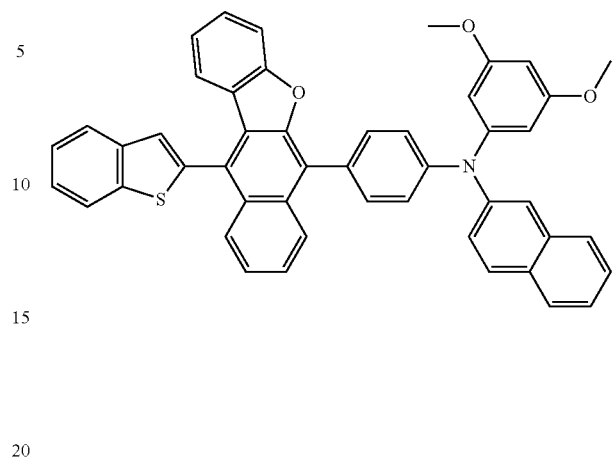
P-29
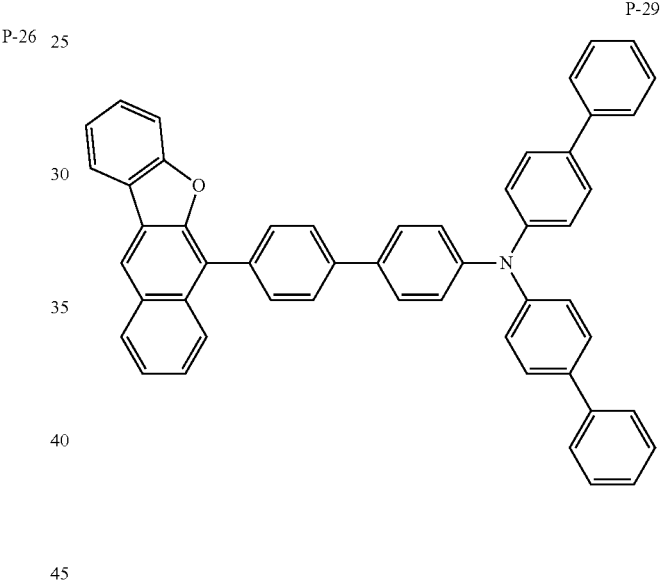
P-30
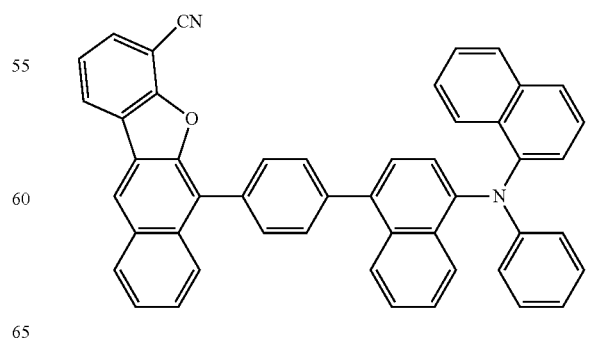

P-31
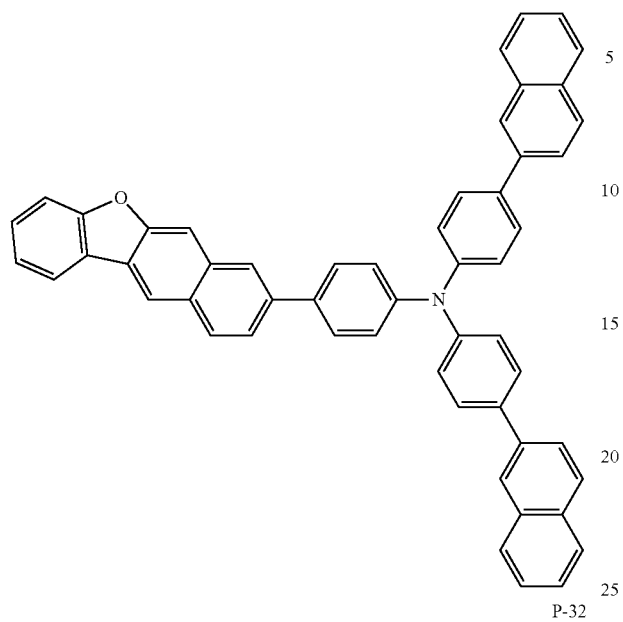
P-32
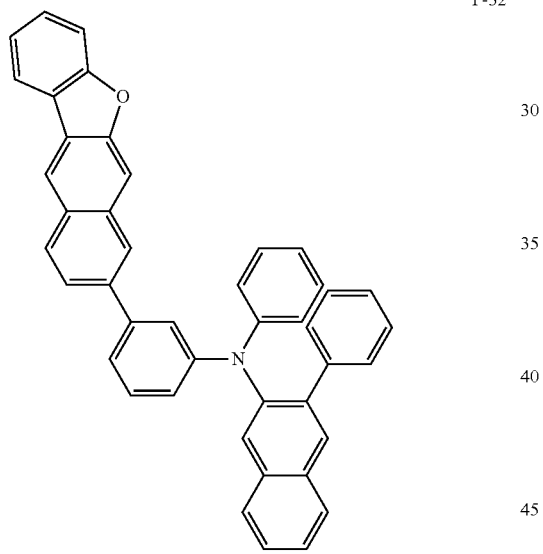
P-33
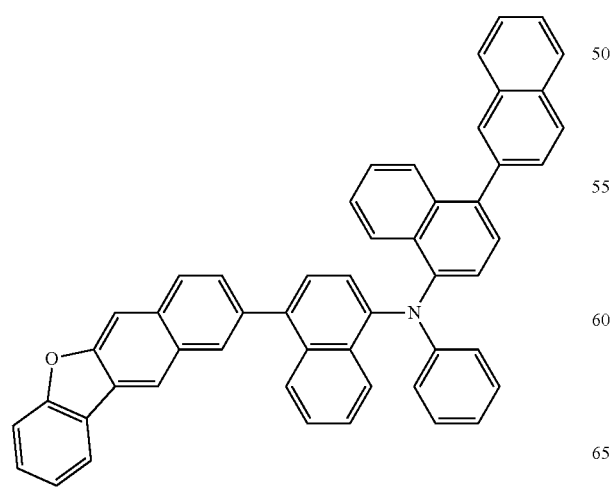
P-34
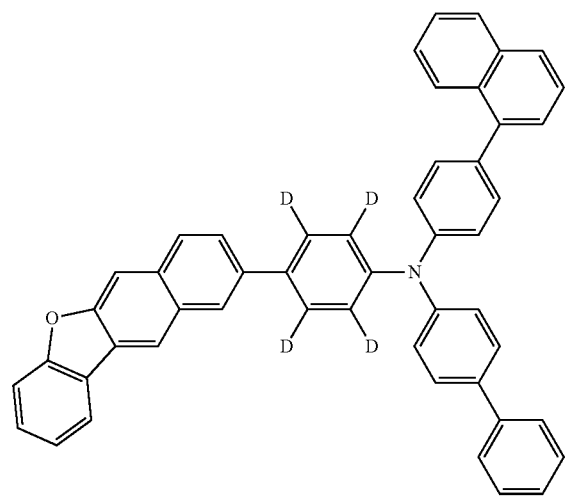
P-35
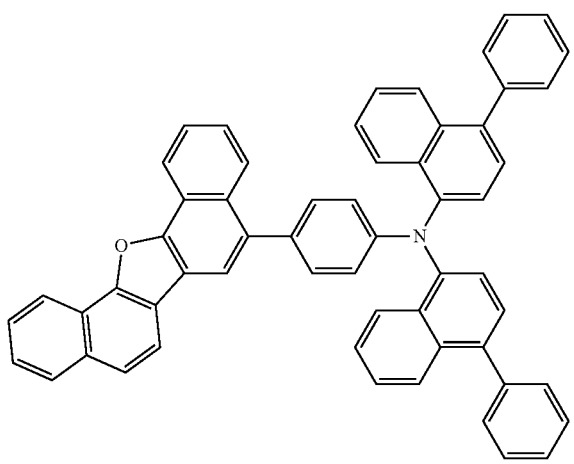
P-36
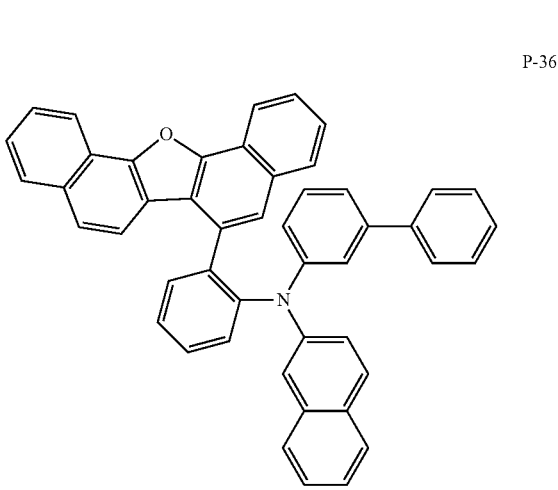

P-37
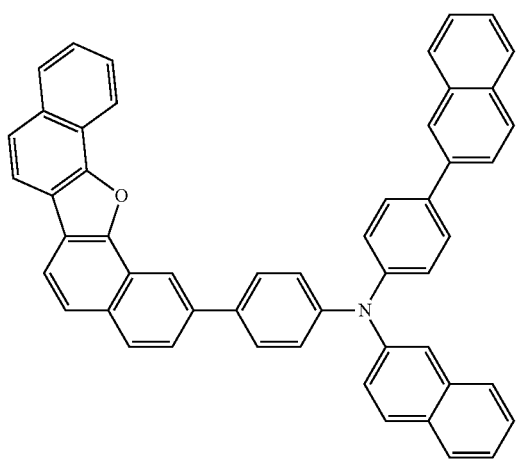
P-38
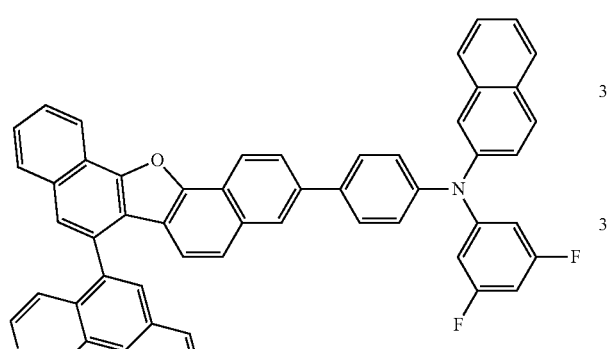
P-39
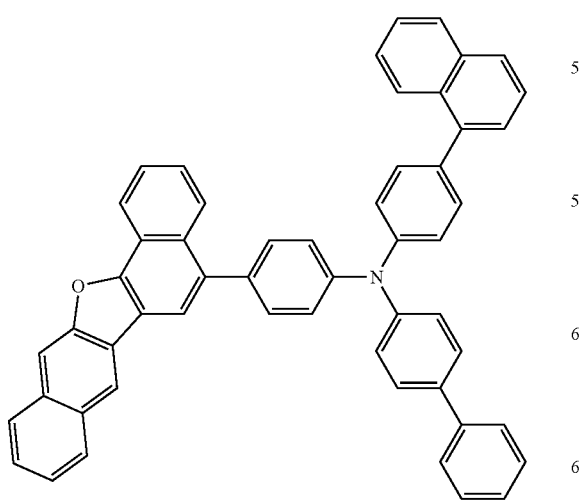
P-40
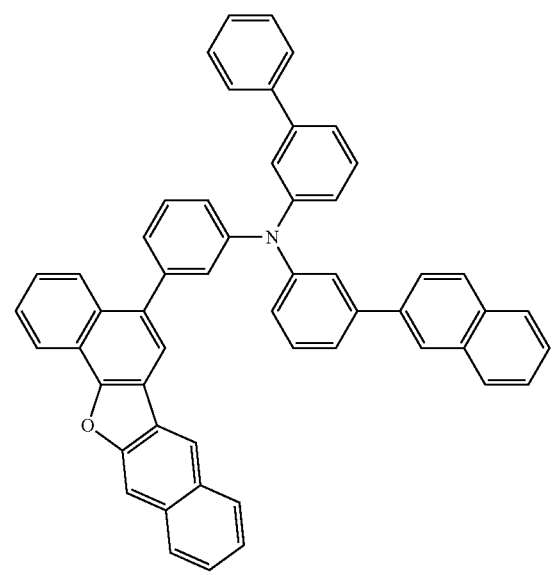
P-41
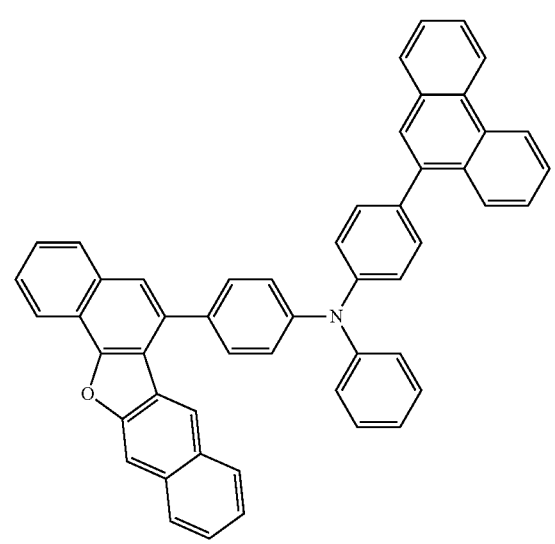
P-42
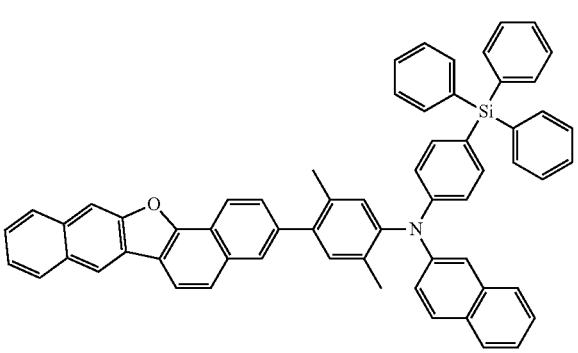

P-43
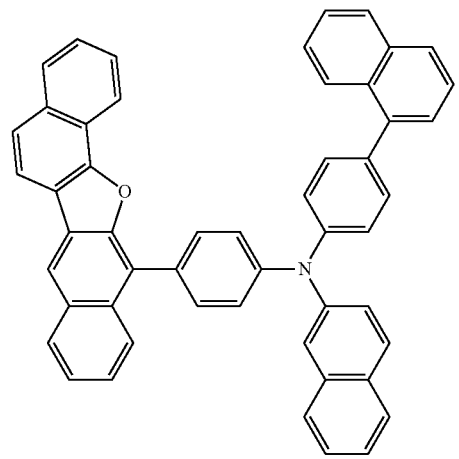
P-44
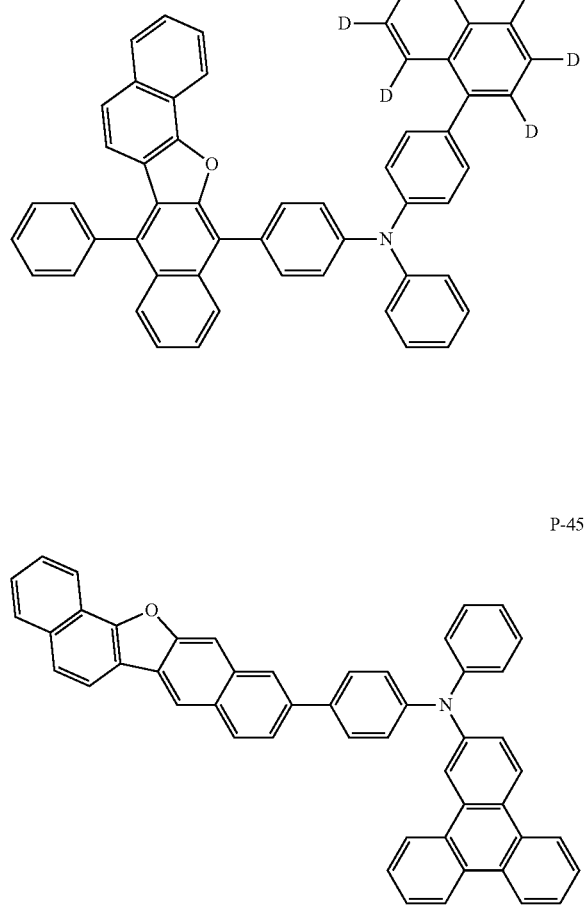
P-45
P-46
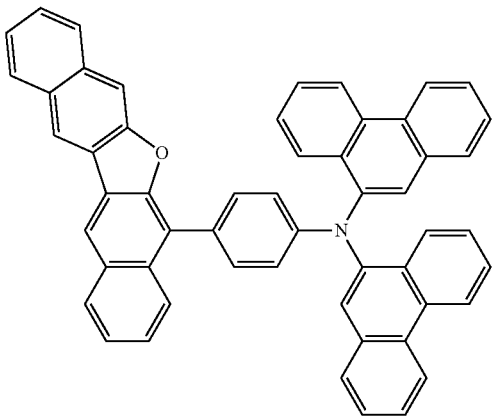
P-47
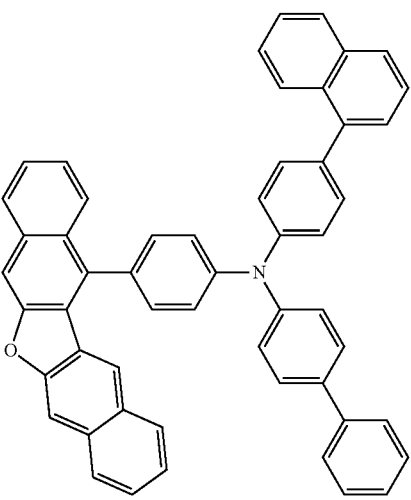
P-48
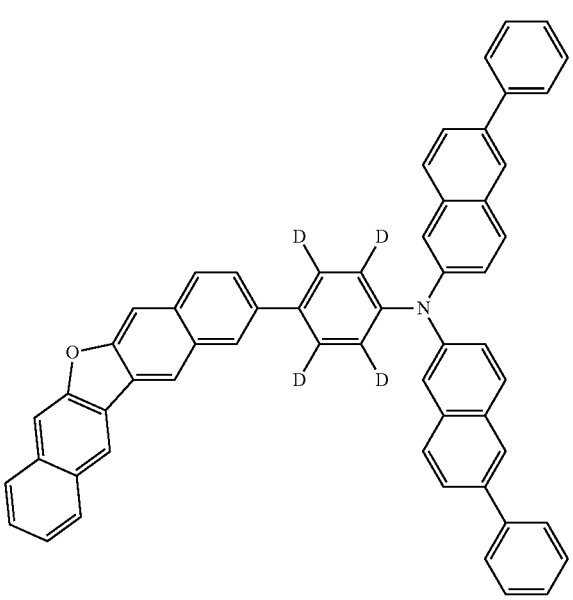
In another aspect of the present invention, the present invention provides an organic electric element comprising a first electrode, a second electrode, and an organic material layer formed between the first electrode and the second electrode. The organic material layer may comprise at least one layer of a hole injection layer, a hole transport layer, an emission-auxiliary layer, a light emitting layer, an electron transport-auxiliary layer, an electron transport layer and an electron injection layer, and at least one compound of the above compounds may be comprised in the organic material layer. That is, the organic material layer may be formed as a single compound or a mixture of two or more kinds represented by Formula 1. Preferably, a single compound or a mixture of two or more kinds may be comprised in a hole transport layer and/or an emission-auxiliary layer, or a hole transport layer and/or an emission-auxiliary layer may be formed by the compound.

Hereinafter, Synthesis method of the compound represented by Formula 1 according to one embodiment of the present invention and preparation method of an organic electric element will be described in detail by way of examples. However, the present invention is not limited to the following examples.

SYNTHESIS EXAMPLE

The compound (final products) represented by Formula 1 according to the present invention are synthesized by reacting Sub 1 and Sub 2 as shown in Reaction Scheme 1, but are not limited thereto.

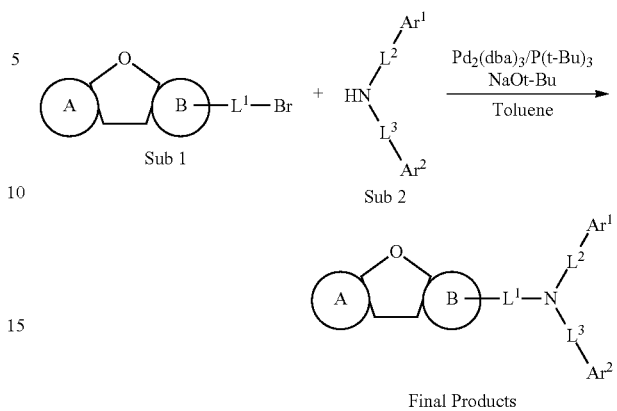

A ring, B ring, $L^1$ to $L^3$, $Ar^1$ and $Ar^2$ are each identical as defined in formula 1 above.

I. Synthesis of Sub 1

Sub 1 of the Reaction Scheme 1 can be synthesized according to, but not limited to, the reaction route of the following Reaction Scheme 2.

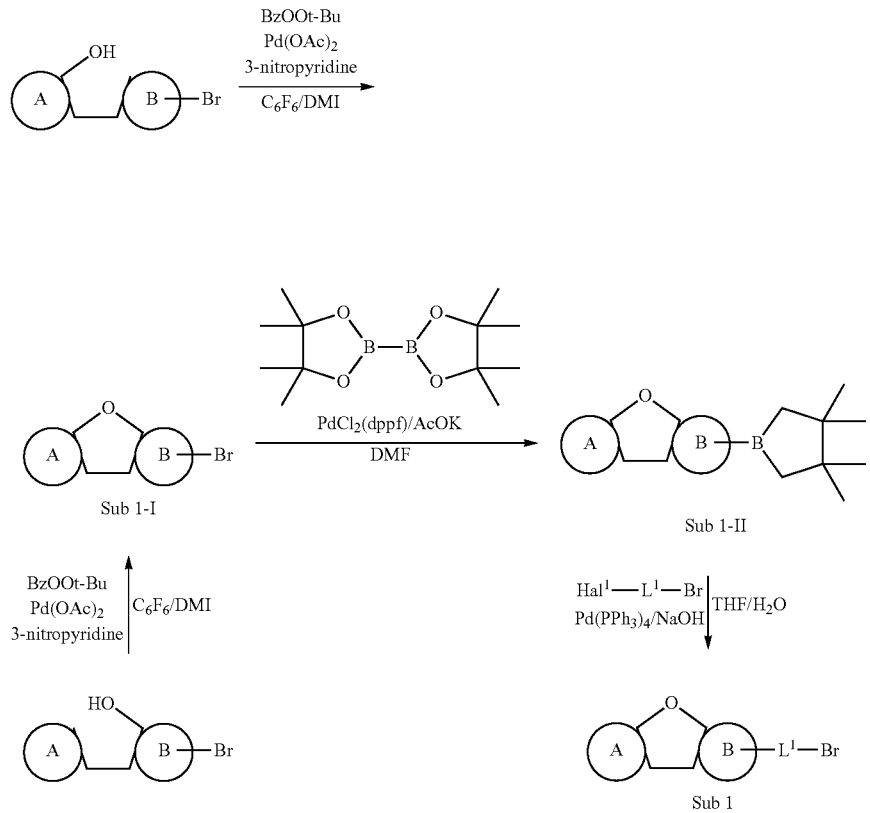

wherein $Hal^1$ is Br or I

Synthesis Examples of compounds comprised in Sub 1 are as follows.

1. Synthesis Example of Sub 1-3

<Reaction Scheme 3>

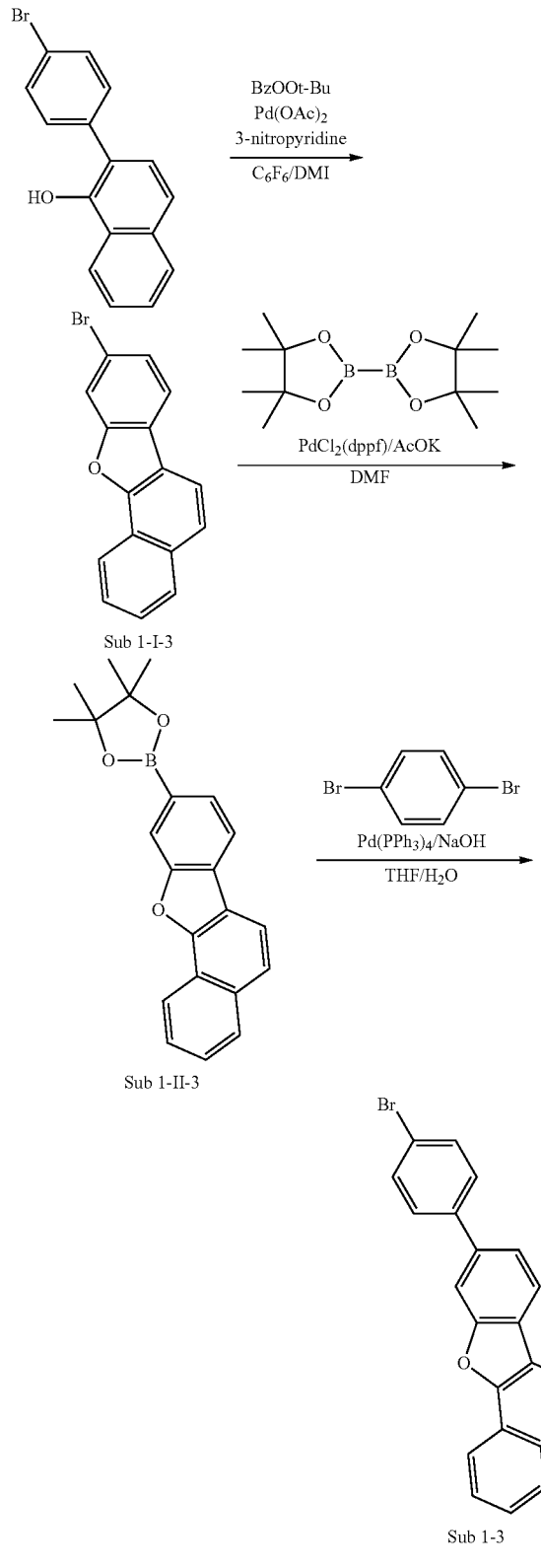

(1) Synthesis of Sub 1-I-3

The starting material 2-(4-bromophenyl)naphthalen-1-ol (29.89 g, 99.91 mmol) was placed into a round bottom flask together with Pd(OAc)$_2$ (2.24 g, 9.99 mmol), 3-nitropyridine (1.24 g, 9.99 mmol), then, dissolved in C$_6$F$_6$ (150 ml) and DMI (100 ml). And then, tert-butyl peroxybenzoate (38.81 g, 199.83 mmol) was added, and stirred 90° C. When the reaction was completed, the reaction product was extracted with CH$_2$Cl$_2$ and water, and then, the organic layer was dried with MgSO$_4$ and concentrated. Then, the concentrate was passed through silica gel column and recrystallized to obtain 12.77 g (yield: 43%) of the product.

(2) Synthesis of Sub 1-II-3

Sub 1-I-3 (12.77 g, 42.97 mmol) obtained in the above synthesis was added into a round bottom flask, then, dissolved in DMF (215 ml). After adding Bis(pinacolato) diboron (12.00 g, 47.27 mmol), Pd(dppf)Cl$_2$ (1.05 g, 1.29 mmol), KOAc (12.65 g, 128.92 mmol), stirring at 90° C. was followed. When the reaction was completed, DMF was removed by distillation, and then extracting with CH$_2$Cl$_2$ and water was followed. The organic layer was dried with MgSO$_4$ and concentrated. Then, the concentrate was passed through silica gel column and recrystallized to obtain 12.43 g (yield: 84%) of the product.

(3) Synthesis of Sub 1-3

Sub 1-II-3 (12.43 g, 36.11 mmol) obtained in the above synthesis was added into a round bottom flask, then, dissolved in THF (120 ml). After adding 1,4-dibromobenzene (9.37 g, 39.72 mmol), Pd(PPh$_3$)$_4$ (1.25 g, 1.08 mmol), NaOH (4.33 g, 108.34 mmol), water (60 ml), stirring at 80° C. was followed. When the reaction was completed, DMF was removed by distillation, and then extracting with CH$_2$Cl$_2$ and water was followed. The organic layer was dried with MgSO$_4$ and concentrated. Then, the concentrate was passed through silica gel column and recrystallized to obtain 10.51 g (yield: 78%) of the product.

2. Synthesis Examples of Sub 1-9

<Reaction Scheme 4>

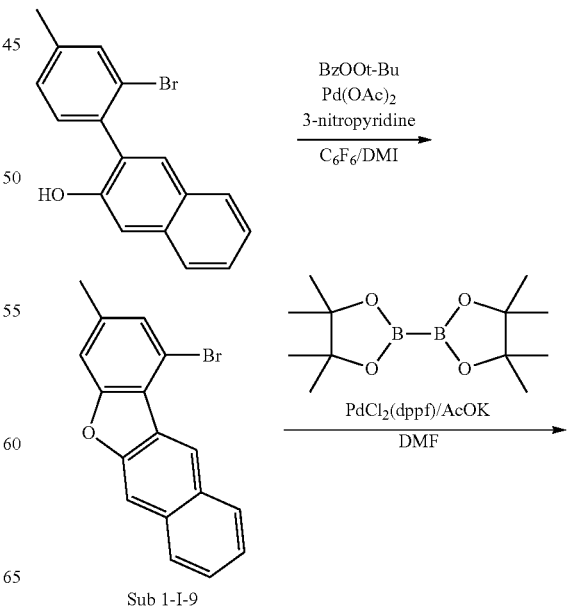

3. Synthesis Examples of Sub 1-15

<Reaction Scheme 5>

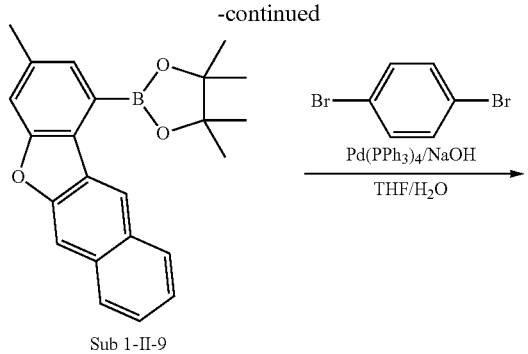

Sub 1-II-9

Sub 1-9

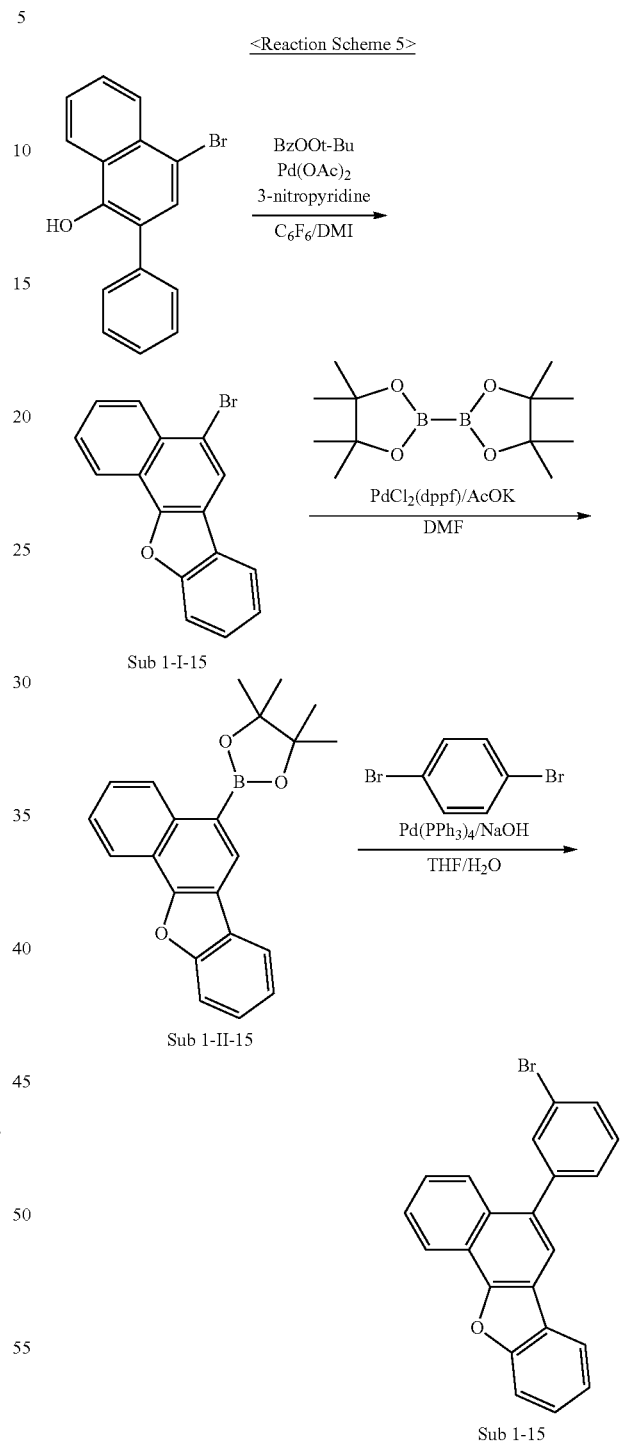

Sub 1-I-15

Sub 1-II-15

Sub 1-15

(1) Synthesis of Sub 1-I-9

Pd(OAc)$_2$ (4.03 g, 17.96 mmol), 3-nitropyridine (2.23 g, 17.96 mmol), tert-butyl peroxybenzoate (69.76 g, 359.14 mmol), C$_6$F$_6$ (270 ml), DMI (180 ml) were added to the starting material 3-(2-bromo-4-methylphenyl)naphthalen-2-ol (56.24 g, 179.57 mmol), and then 22.91 g (yield: 41%) of the product was obtained by using the same manner as described above for the synthesis of Sub 1-I-3.

(2) Synthesis of Sub 1-II-9

Bis(pinacolato)diboron (20.57 g, 80.99 mmol), Pd(dppf)Cl$_2$ (1.80 g, 2.21 mmol), KOAc (21.68 g, 220.88 mmol), DMF (370 ml) were added to Sub 1-I-9 (22.91 g, 73.63 mmol) obtained in the above synthesis, and then 19.52 g (yield: 74%) of the product was obtained by using the same manner as described above for the synthesis of Sub 1-II-3.

(3) Synthesis of Sub 1-9

1,4-dibromobenzene (14.14 g, 59.94 mmol), Pd(PPh$_3$)$_4$ (1.89 g, 1.63 mmol), NaOH (6.54 g, 163.47 mmol), THF (190 ml), water (95 ml) were added to Sub 1-II-9 (19.52 g, 54.49 mmol) obtained in the above synthesis, and then 13.72 g (yield: 65%) of the product was obtained by using the same manner as described above for the synthesis of Sub 1-3.

(1) Synthesis of Sub 1-I-15

Pd(OAc)$_2$ (4.04 g, 18.01 mmol), 3-nitropyridine (2.24 g, 18.01 mmol), tert-butyl peroxybenzoate (69.98 g, 360.28 mmol), C$_6$F$_6$ (270 ml), DMI (180 ml) were added to the starting material 4-bromo-2-phenylnaphthalen-1-ol (53.89 g, 180.14 mmol), and then 24.09 g (yield: 45%) of the product was obtained by using the same manner as described above for the synthesis of Sub 1-I-3.

(2) Synthesis of Sub 1-II-15

Bis(pinacolato)diboron (22.65 g, 89.18 mmol), Pd(dppf)Cl$_2$ (1.99 g, 2.43 mmol), KOAc (23.87 g, 243.21 mmol), DMF (400 ml) were added to Sub 1-I-15 (24.09 g, 81.07 mmol) obtained in the above synthesis, and then 18.98 g (yield: 68%) of the product was obtained by using the same manner as described above for the synthesis of Sub 1-II-3.

(3) Synthesis of Sub 1-15

1,3-dibromobenzene (14.31 g, 60.65 mmol), Pd(PPh$_3$)$_4$ (1.91 g, 1.65 mmol), NaOH (6.62 g, 165.42 mmol), THF (190 ml), water (95 ml) were added to Sub 1-II-15 (18.98 g, 55.14 mmol) obtained in the above synthesis, and then 12.76 g (yield: 62%) of the product was obtained by using the same manner as described above for the synthesis of Sub 1-3.

4. Synthesis Examples of Sub 1-18

<Reation Scheme 6>

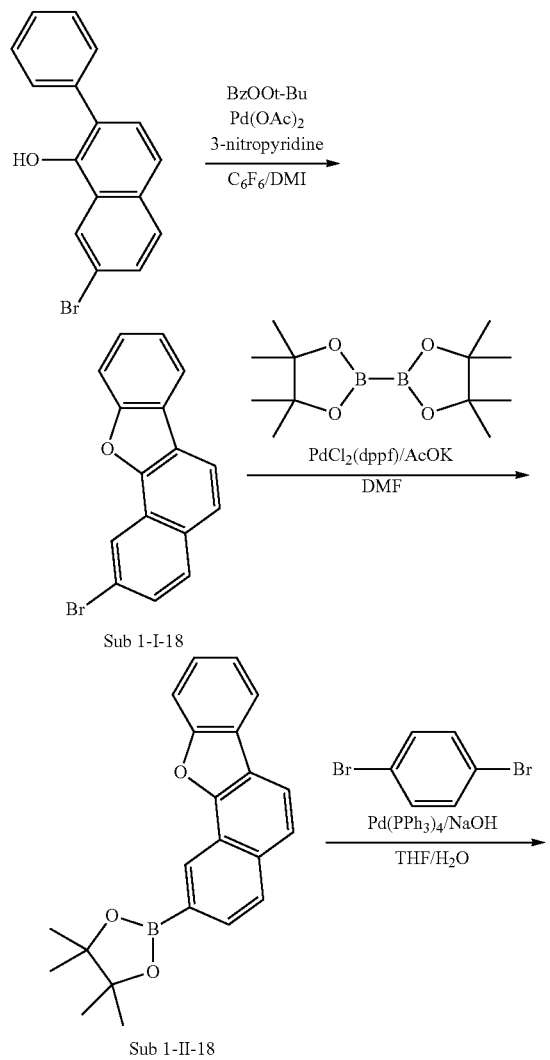

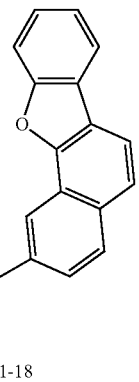
Sub 1-18

(1) Synthesis of Sub 1-I-18

Pd(OAc)$_2$ (2.70 g, 12.01 mmol), 3-nitropyridine (1.49 g, 12.01 mmol), tert-butyl peroxybenzoate (46.66 g, 240.21 mmol), C$_6$F$_6$ (180 ml), DMI (120 ml) were added to the starting material 7-bromo-2-phenylnaphthalen-1-ol (35.93 g, 120.10 mmol), and then 16.42 g (yield: 46%) of the product was obtained by using the same manner as described above for the synthesis of Sub 1-I-3.

(2) Synthesis of Sub 1-II-18

Bis(pinacolato)diboron (15.44 g, 60.78 mmol), Pd(dppf)Cl$_2$ (1.35 g, 1.66 mmol), KOAc (16.27 g, 165.77 mmol), DMF (275 ml) were added to Sub 1-I-18 (16.42 g, 55.26 mmol) obtained in the above synthesis, and then 15.22 g (yield: 80%) of the product was obtained by using the same manner as described above for the synthesis of Sub 1-II-3.

(3) Synthesis of Sub 1-18

1,4-dibromobenzene (11.47 g, 48.64 mmol), Pd(PPh$_3$)$_4$ (1.53 g, 1.33 mmol), NaOH (5.31 g, 132.65 mmol), THF (160 ml), water (95 ml) were added to Sub 1-II-18 (15.22 g, 44.22 mmol) obtained in the above synthesis, and then 11.06 g (yield: 67%) of the product was obtained by using the same manner as described above for the synthesis of Sub 1-3.

5. Synthesis Examples of Sub 1-22

<Reaction Scheme 7>

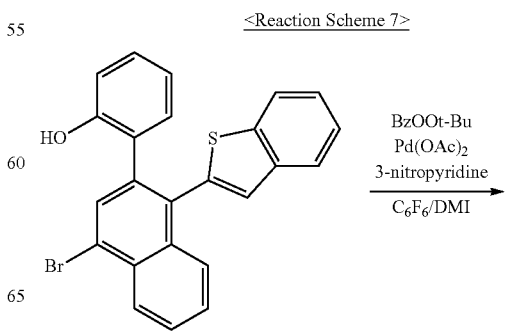

38

6. Synthesis Examples of Sub 1-28

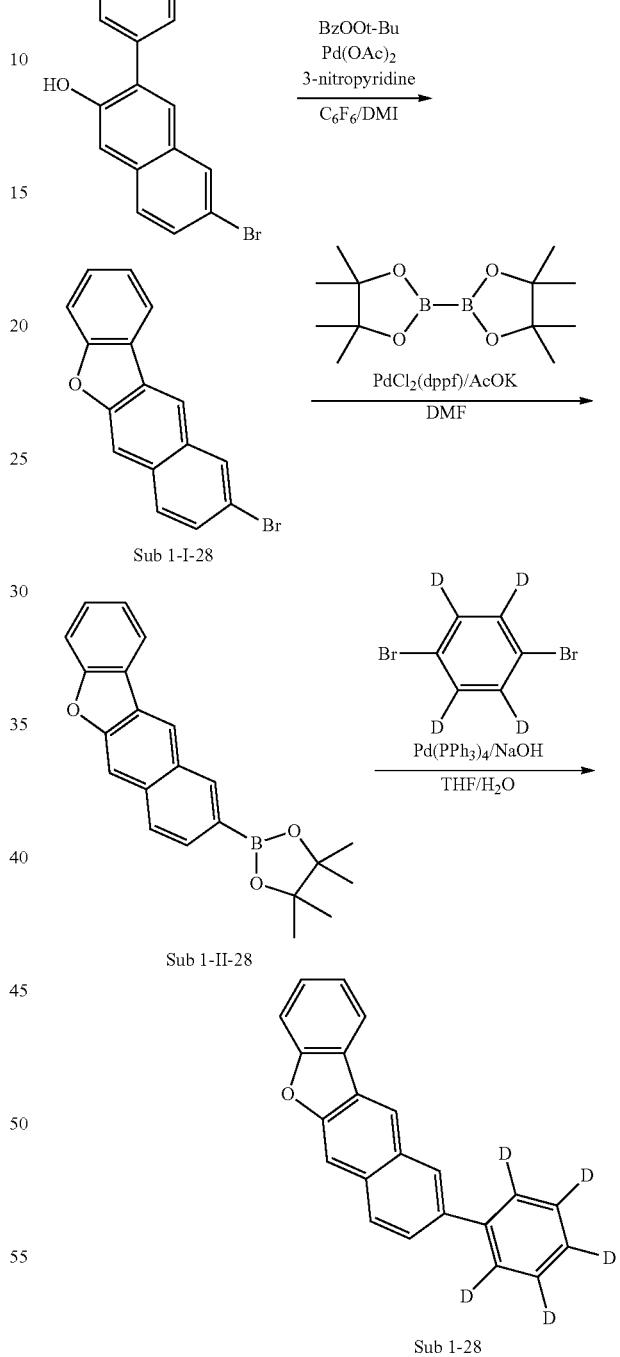

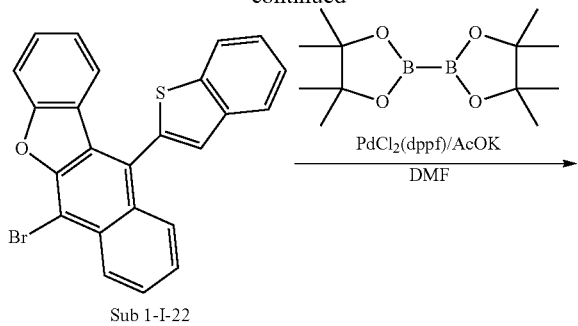

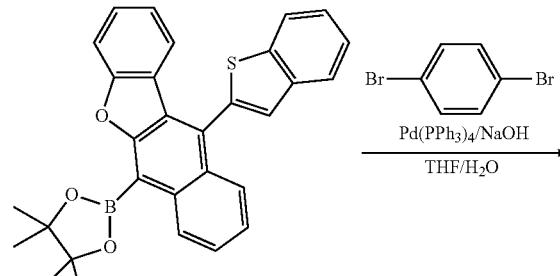

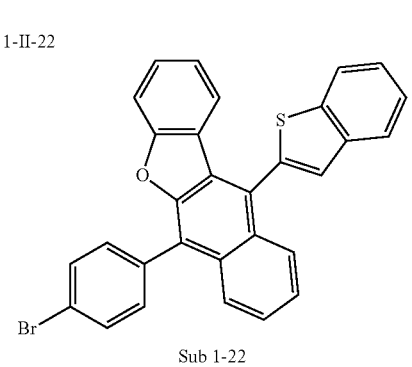

(1) Synthesis of Sub 1-I-22

Pd(OAc)$_2$ (3.58 g, 15.96 mmol), 3-nitropyridine (1.98 g, 15.96 mmol), tert-butyl peroxybenzoate (62.01 g, 319.24 mmol), C$_6$F$_6$ (240 ml), DMI (160 ml) were added to the starting material 2-(1-(benzo[b]thiophen-2-yl)-4-bromonaphthalen-2-yl)phenol (68.85 g, 159.62 mmol), and then 26.04 g (yield: 38%) of the product was obtained by using the same manner as described above for the synthesis of Sub 1-I-3.

(2) Synthesis of Sub 1-II-22

Bis(pinacolato)diboron (16.94 g, 66.72 mmol), Pd(dppf)Cl$_2$ (1.49 g, 1.82 mmol), KOAc (17.86 g, 181.96 mmol), DMF (300 ml) were added to Sub 1-I-22 (26.04 g, 60.65 mmol) obtained in the above synthesis, and then 21.96 g (yield: 76%) of the product was obtained by using the same manner as described above for the synthesis of Sub 1-II-3.

(3) Synthesis of Sub 1-22

1,4-dibromobenzene (11.96 g, 50.71 mmol), Pd(PPh$_3$)$_4$ (1.60 g, 1.38 mmol), NaOH (5.53 g, 138.29 mmol), THF (160 ml), water (95 ml) were added to Sub 1-II-22 (21.96 g, 46.10 mmol) obtained in the above synthesis, and then 17.01 g (yield: 73%) of the product was obtained by using the same manner as described above for the synthesis of Sub 1-3.

(1) Synthesis of Sub 1-I-28

Pd(OAc)$_2$ (3.15 g, 14.03 mmol), 3-nitropyridine (1.74 g, 14.03 mmol), tert-butyl peroxybenzoate (54.51 g, 280.65 mmol), C$_6$F$_6$ (210 ml), DMI (140 ml) were added to the starting material 6-bromo-3-phenylnaphthalen-2-ol (41.98 g, 140.33 mmol), and then 20.02 g (yield: 48%) of the product was obtained by using the same manner as described above for the synthesis of Sub 1-I-3.

(2) Synthesis of Sub 1-II-28

Bis(pinacolato)diboron (18.82 g, 74.11 mmol), Pd(dppf)Cl$_2$ (1.65 g, 2.02 mmol), KOAc (19.84 g, 202.12 mmol), DMF (340 ml) were added to Sub 1-I-28 (20.02 g, 67.37 mmol) obtained in the above synthesis, and then 19.25 g (yield: 83%) of the product was obtained by using the same manner as described above for the synthesis of Sub 1-II-3.

(3) Synthesis of Sub 1-28

1,4-dibromobenzene-d4 (14.76 g, 61.52 mmol), Pd(PPh$_3$)$_4$ (1.94 g, 1.68 mmol), NaOH (6.71 g, 167.78 mmol), THF (200 ml), water (95 ml) were added to Sub 1-II-28 (19.25 g, 55.93 mmol) obtained in the above synthesis, and then 12.45 g (yield: 59%) of the product was obtained by using the same manner as described above for the synthesis of Sub 1-3.

7. Synthesis Examples of Sub 1-30

<Reaction Scheme 9>

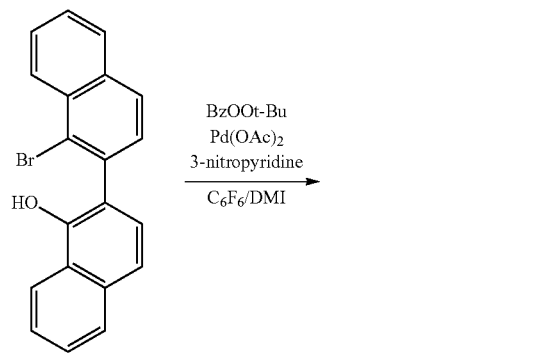

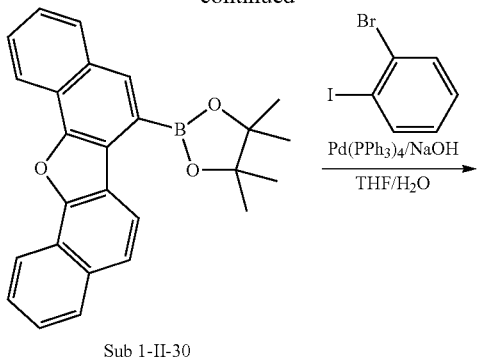

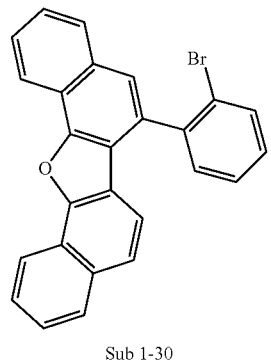

Sub 1-30

(1) Synthesis of Sub 1-I-30

Pd(OAc)$_2$ (6.28 g, 27.99 mmol), 3-nitropyridine (3.47 g, 27.99 mmol), tert-butyl peroxybenzoate (108.72 g, 559.76 mmol), C$_6$F$_6$ (420 ml), DMI (280 ml) were added to the starting material 1'-bromo-[2,2'-binaphthalen]-1-ol (97.74 g, 279.88 mmol), and then 34.01 g (yield: 35%) of the product was obtained by using the same manner as described above for the synthesis of Sub 1-I-3.

(2) Synthesis of Sub 1-II-30

Bis(pinacolato)diboron (27.36 g, 107.75 mmol), Pd(dppf)Cl$_2$ (2.40 g, 2.94 mmol), KOAc (28.84 g, 293.87 mmol), DMF (490 ml) were added to Sub 1-I-30 (34.01 g, 97.96 mmol) obtained in the above synthesis, and then 24.33 g (yield: 63%) of the product was obtained by using the same manner as described above for the synthesis of Sub 1-II-3.

(3) Synthesis of Sub 1-30

1-bromo-2-iodobenzene (19.20 g, 67.88 mmol), Pd(PPh$_3$)$_4$ (2.14 g, 1.85 mmol), NaOH (7.41 g, 185.13 mmol), THF (220 ml), water (95 ml) were added to Sub 1-II-30 (24.33 g, 61.71 mmol) obtained in the above synthesis, and then 15.67 g (yield: 60%) of the product was obtained by using the same manner as described above for the synthesis of Sub 1-3.

8. Synthesis Examples of Sub 1-38

<Reaction Scheme 10>

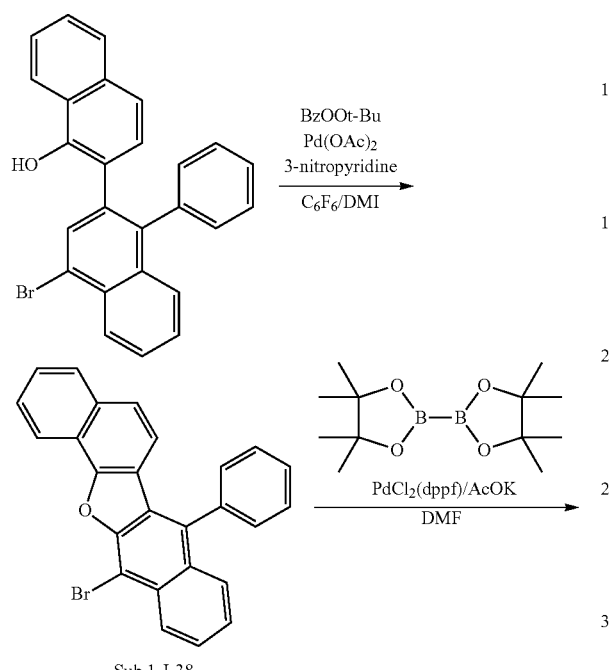

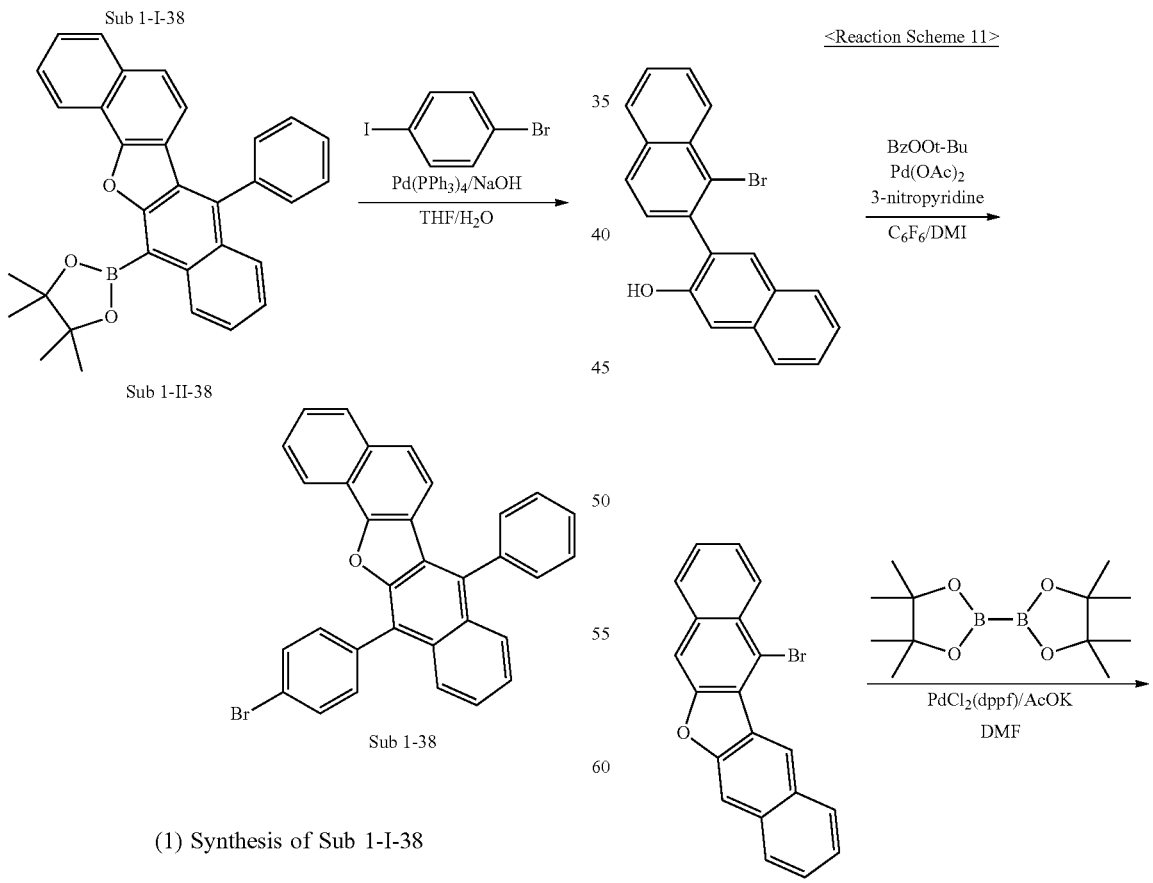

(1) Synthesis of Sub 1-I-38

Pd(OAc)₂ (3.59 g, 16.00 mmol), 3-nitropyridine (1.99 g, 16.00 mmol), tert-butyl peroxybenzoate (62.15 g, 319.99 mmol), $C_6F_6$ (240 ml), DMI (160 ml) were added to the starting material 4'-bromo-1'-phenyl-[2,2'-binaphthalen]-1-ol (68.05 g, 160.00 mmol), and then 21.67 g (yield: 32%) of the product was obtained by using the same manner as described above for the synthesis of Sub 1-I-3.

(2) Synthesis of Sub 1-II-38

Bis(pinacolato)diboron (14.30 g, 56.31 mmol), Pd(dppf)Cl₂ (1.25 g, 1.54 mmol), KOAc (15.07 g, 153.58 mmol), DMF (255 ml) were added to Sub 1-I-38 (21.67 g, 51.19 mmol) obtained in the above synthesis, and then 18.06 g (yield: 75%) of the product was obtained by using the same manner as described above for the synthesis of Sub 1-II-3.

(3) Synthesis of Sub 1-38

1-bromo-4-iodobenzene (11.95 g, 42.23 mmol), Pd(PPh₃)₄ (1.33 g, 1.15 mmol), NaOH (4.61 g, 115.19 mmol), THF (140 ml), water (95 ml) were added to Sub 1-II-38 (18.06 g, 38.40 mmol) obtained in the above synthesis, and then 13.81 g (yield: 72%) of the product was obtained by using the same manner as described above for the synthesis of Sub 1-3.

9. Synthesis Examples of Sub 1-41

<Reaction Scheme 11>

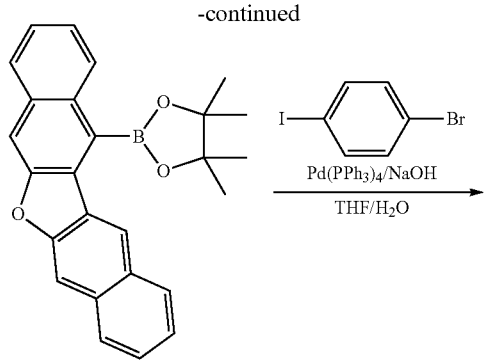

Sub 1-II-41

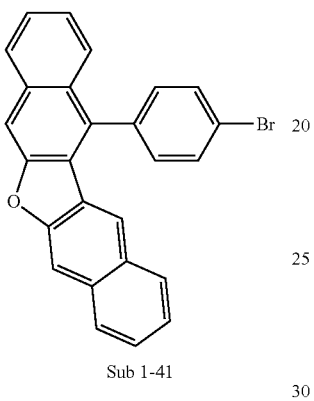

Sub 1-41

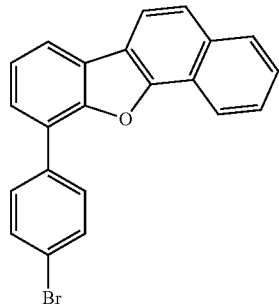

Sub 1-1

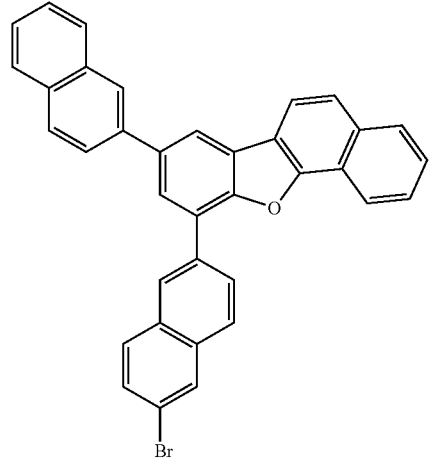

Sub 1-2

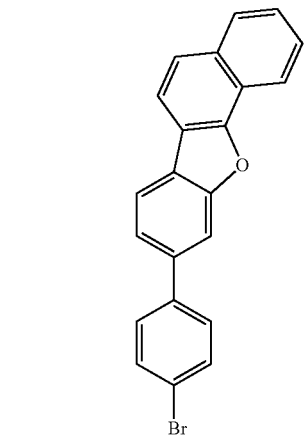

Sub 1-3

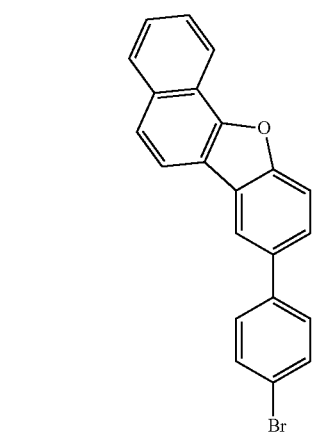

Sub 1-4

(1) Synthesis of Sub 1-I-41

Pd(OAc)$_2$ (4.04 g, 18.01 mmol), 3-nitropyridine (2.24 g, 18.01 mmol), tert-butyl peroxybenzoate (69.98 g, 360.29 mmol), C$_6$F$_6$ (270 ml), DMI (180 ml) were added to the starting material 1'-bromo-[2,2'-binaphthalen]-3-ol (62.91 g, 180.14 mmol), and then 23.14 g (yield: 37%) of the product was obtained by using the same manner as described above for the synthesis of Sub 1-I-3.

(2) Synthesis of Sub 1-II-41

Bis(pinacolato)diboron (18.62 g, 73.31 mmol), Pd(dppf)Cl$_2$ (1.63 g, 2.00 mmol), KOAc (19.62 g, 199.94 mmol), DMF (330 ml) were added to Sub 1-I-41 (23.14 g, 66.65 mmol) obtained in the above synthesis, and then 16.03 g (yield: 61%) of the product was obtained by using the same manner as described above for the synthesis of Sub 1-II-3.

(3) Synthesis of Sub 1-41

1-bromo-4-iodobenzene (12.65 g, 44.72 mmol), Pd(PPh$_3$)$_4$ (1.41 g, 1.22 mmol), NaOH (4.88 g, 121.97 mmol), THF (140 ml), water (95 ml) were added to Sub 1-II-41 (16.03 g, 40.66 mmol) obtained in the above synthesis, and then 11.01 g (yield: 64%) of the product was obtained by using the same manner as described above for the synthesis of Sub 1-3.

The compound belonging to Sub 1 may be, but not limited to, the following compounds, and Table 1 shows FD-MS (Field Desorption-Mass Spectrometry) values of compounds belonging to Sub 1.

Sub 1-5
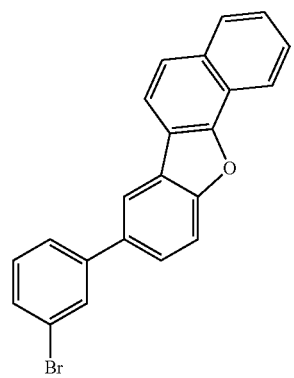
Sub 1-6
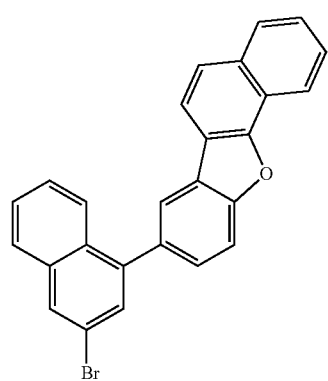
Sub 1-7
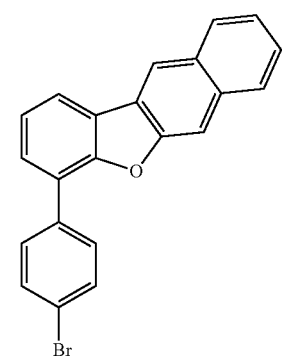
Sub 1-8
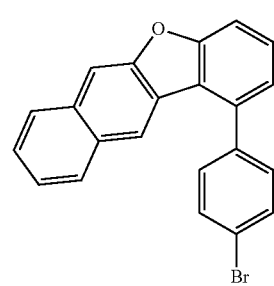
Sub 1-9
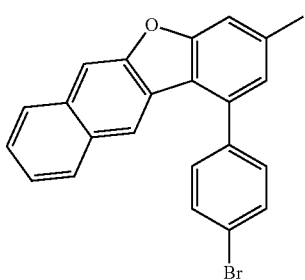
Sub 1-10
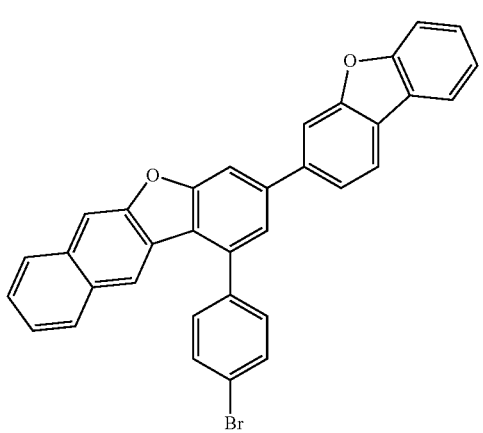
Sub 1-11
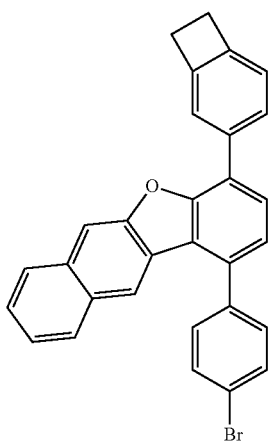
Sub 1-12
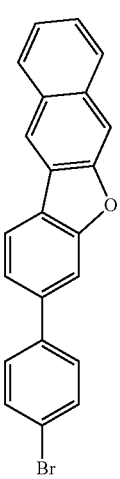

Sub 1-13 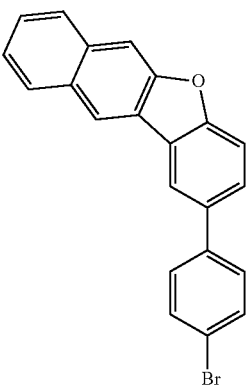
Sub 1-14 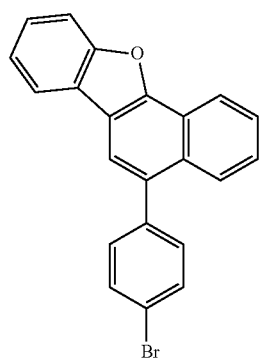
Sub 1-15 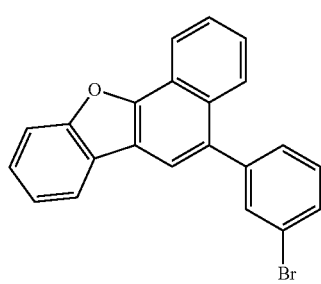
Sub 1-16 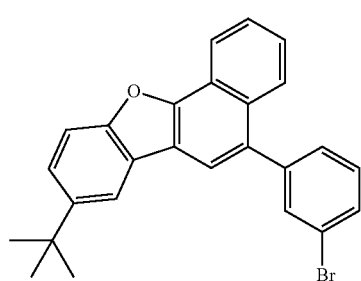
Sub 1-17 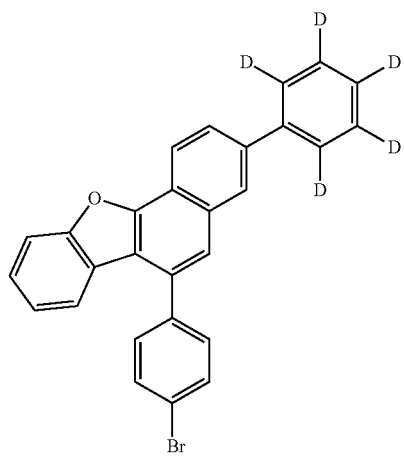
Sub 1-18 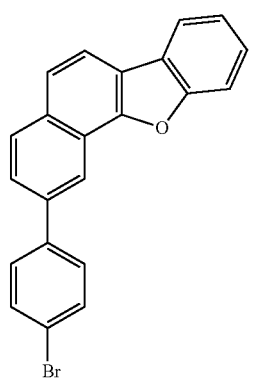
Sub 1-19 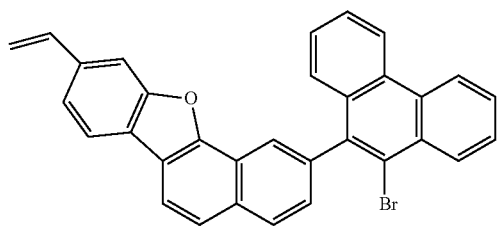
Sub 1-20 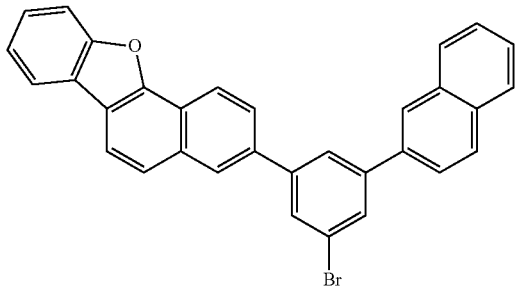

-continued
Sub 1-21
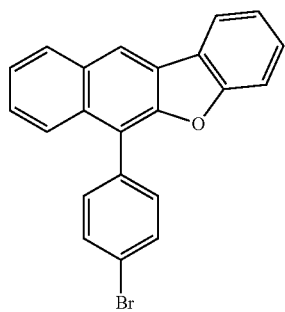
Sub 1-22
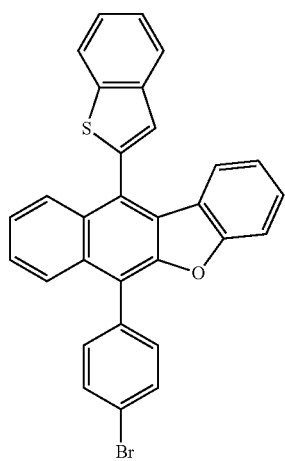
Sub 1-23
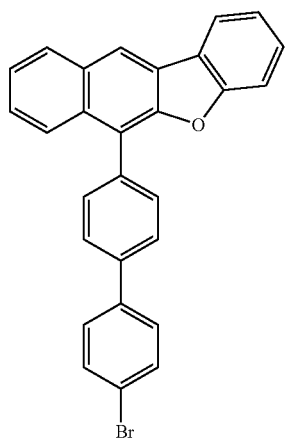
Sub 1-24
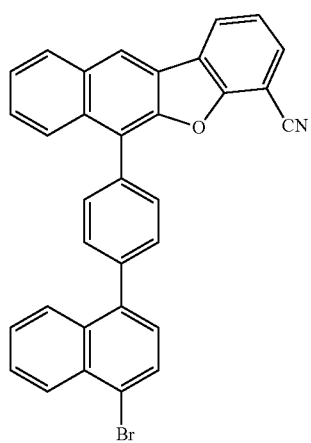
-continued
Sub 1-25
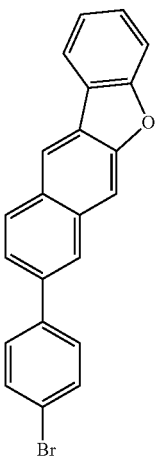
Sub 1-26
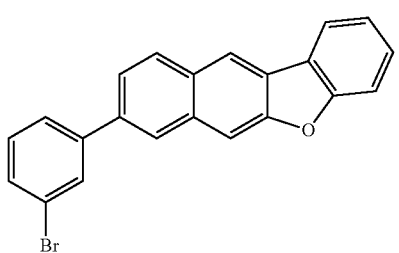
Sub 1-27
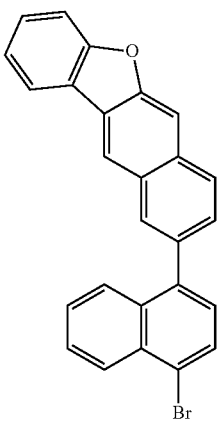
Sub 1-28
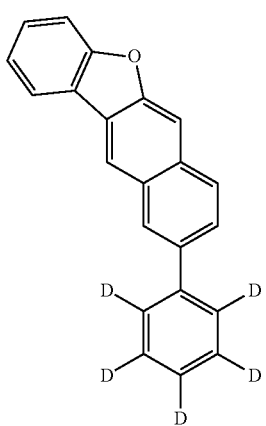

-continued
Sub 1-29
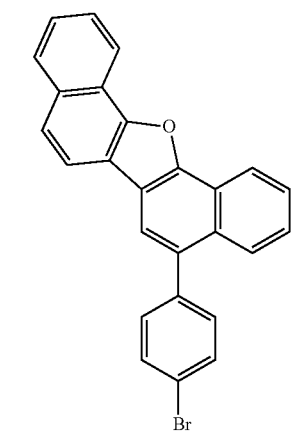
Sub 1-30
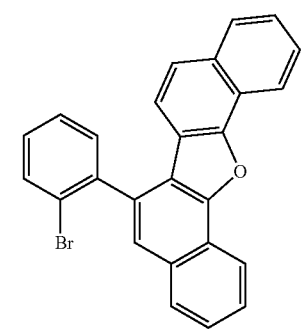
Sub 1-31
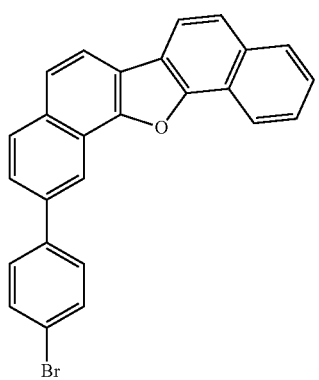
Sub 1-32
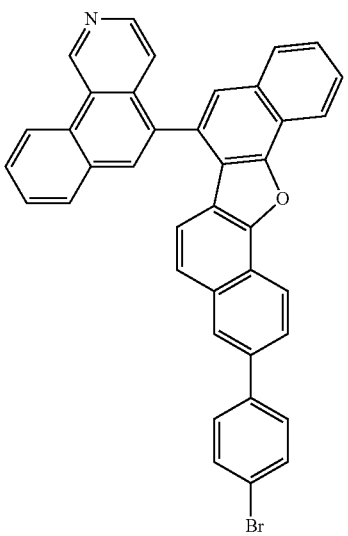
Sub 1-33
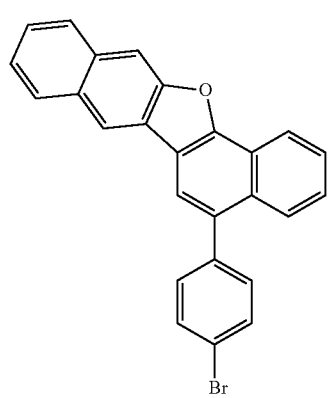
Sub 1-34
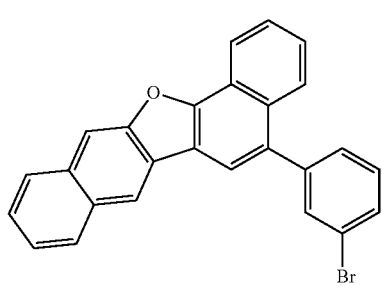
Sub 1-35
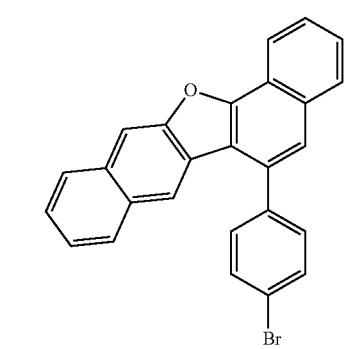

Sub 1-36
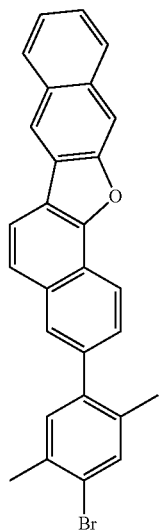
Sub 1-37
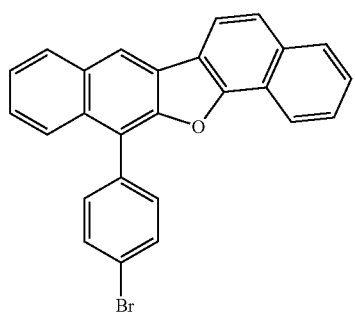
Sub 1-38
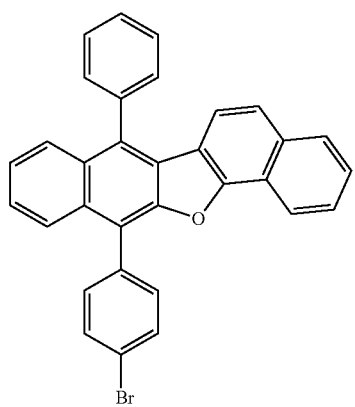
Sub 1-39
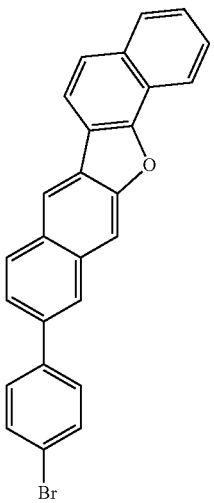
Sub 1-40
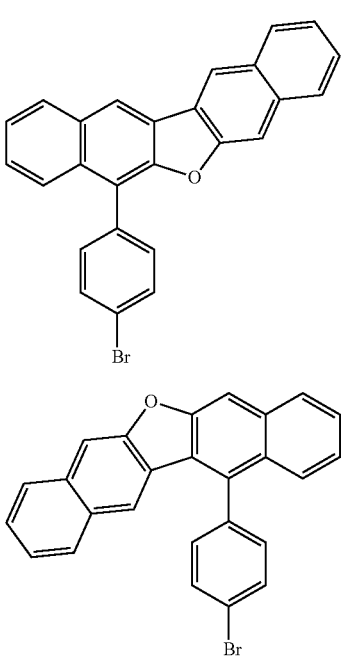
Sub 1-41
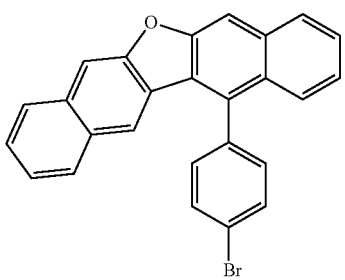
Sub 1-42
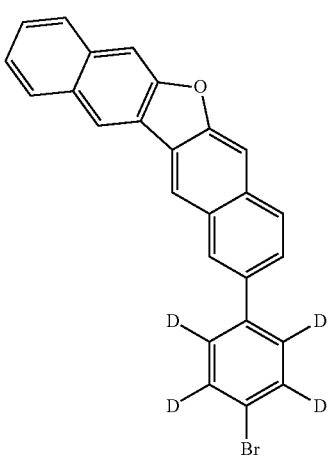

TABLE 1

| compound | FD-MS | compound | FD-MS |
|---|---|---|---|
| Sub 1-1 | m/z = 372.01($C_{22}H_{13}BrO$ = 373.24) | Sub 1-2 | m/z = 548.08($C_{36}H_{21}BrO$ = 549.46) |
| Sub 1-3 | m/z = 372.01($C_{22}H_{13}BrO$ = 373.24) | Sub 1-4 | m/z = 372.01($C_{22}H_{13}BrO$ = 373.24) |
| Sub 1-5 | m/z = 372.01($C_{22}H_{13}BrO$ = 373.24) | Sub 1-6 | m/z = 422.03($C_{26}H_{15}BrO$ = 423.30) |
| Sub 1-7 | m/z = 372.01($C_{22}H_{13}BrO$ = 373.24) | Sub 1-8 | m/z = 372.01($C_{22}H_{13}BrO$ = 373.24) |
| Sub 1-9 | m/z = 386.03($C_{23}H_{15}BrO$ = 387.27) | Sub 1-10 | m/z = 538.06($C_{34}H_{19}BrO_2$ = 539.42) |
| Sub 1-11 | m/z = 474.06($C_{30}H_{19}BrO$ = 475.38) | Sub 1-12 | m/z = 372.01($C_{22}H_{13}BrO$ = 373.24) |
| Sub 1-13 | m/z = 372.01($C_{22}H_{13}BrO$ = 373.24) | Sub 1-14 | m/z = 372.01($C_{22}H_{13}BrO$ = 373.24) |
| Sub 1-15 | m/z = 372.01($C_{22}H_{13}BrO$ = 373.24) | Sub 1-16 | m/z = 428.08($C_{26}H_{21}BrO$ = 429.35) |
| Sub 1-17 | m/z = 453.08($C_{28}H_{12}D_5BrO$ = 454.37) | Sub 1-18 | m/z = 372.01($C_{22}H_{13}BrO$ = 373.24) |
| Sub 1-19 | m/z = 498.06($C_{32}H_{19}BrO$ = 499.40) | Sub 1-20 | m/z = 498.06($C_{32}H_{19}BrO$ = 499.40) |
| Sub 1-21 | m/z = 372.01($C_{22}H_{13}BrO$ = 373.24) | Sub 1-22 | m/z = 504.02($C_{30}H_{17}BrOS$ = 505.42) |
| Sub 1-23 | m/z = 448.05($C_{28}H_{17}BrO$ = 449.34) | Sub 1-24 | m/z = 523.06($C_{33}H_{18}BrNO$ = 524.41) |
| Sub 1-25 | m/z = 372.01($C_{22}H_{13}BrO$ = 373.24) | Sub 1-26 | m/z = 372.01($C_{22}H_{13}BrO$ = 373.24) |
| Sub 1-27 | m/z = 422.03($C_{26}H_{15}BrO$ = 423.30) | Sub 1-28 | m/z = 376.04($C_{22}H_9D_4BrO$ = 377.27) |
| Sub 1-29 | m/z = 422.03($C_{26}H_{15}BrO$ = 423.30) | Sub 1-30 | m/z = 422.03($C_{26}H_{15}BrO$ = 423.30) |
| Sub 1-31 | m/z = 422.03($C_{26}H_{15}BrO$ = 423.30) | Sub 1-32 | m/z = 599.09($C_{39}H_{22}BrNO$ = 600.50) |
| Sub 1-33 | m/z = 422.03($C_{26}H_{15}BrO$ = 423.30) | Sub 1-34 | m/z = 422.03($C_{26}H_{15}BrO$ = 423.30) |
| Sub 1-35 | m/z = 422.03($C_{26}H_{15}BrO$ = 423.30) | Sub 1-36 | m/z = 450.06($C_{28}H_{19}BrO$ = 451.35) |
| Sub 1-37 | m/z = 422.03($C_{26}H_{15}BrO$ = 423.30) | Sub 1-38 | m/z = 498.06($C_{32}H_{19}BrO$ = 499.40) |
| Sub 1-39 | m/z = 422.03($C_{26}H_{15}BrO$ = 423.30) | Sub 1-40 | m/z = 422.03($C_{26}H_{15}BrO$ = 423.30) |
| Sub 1-41 | m/z = 422.03($C_{26}H_{15}BrO$ = 423.30) | Sub 1-42 | m/z = 426.06($C_{26}H_{11}D_4BrO$ = 427.33) |

II. Synthesis of Sub 2

Sub 2 of the Reaction Scheme 1 can be synthesized according to, but not limited to, the reaction route of the following Reaction Scheme 12.

<Reaction Scheme 12>

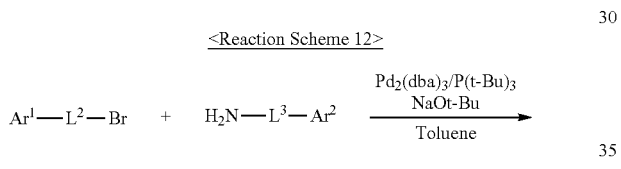

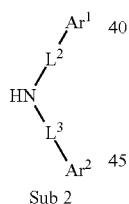

Sub 2

Synthesis Examples of compounds comprised in Sub 2 are as follows.

1. Synthesis Example of Sub 2-4

<Reaction Scheme 13>

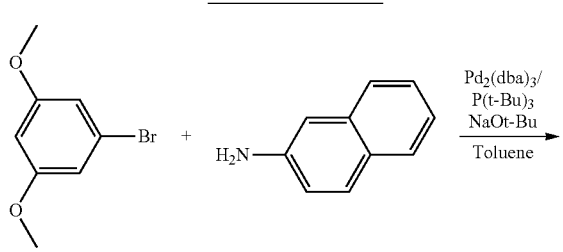

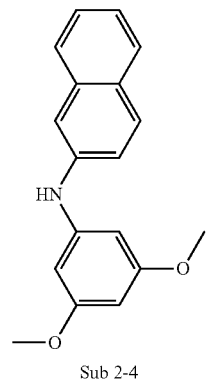

Sub 2-4

The starting material 1-bromo-3,5-dimethoxybenzene (9.62 g, 44.32 mmol) was dissolved in toluene (310 ml) in a round bottom flask, and then naphthalen-2-amine (6.98 g, 48.75 mmol), $Pd_2(dba)_3$ (1.22 g, 1.33 mmol), 50% P(t-Bu)$_3$ (1.7 ml, 3.55 mmol), NaOt-Bu (12.78 g, 132.96 mmol) were added and stirred at 80° C. When the reaction was completed, the reaction product was extracted with $CH_2Cl_2$ and water, and then, the organic layer was dried with $MgSO_4$ and concentrated. Then, the concentrate was passed through silica gel column and recrystallized to obtain 8.42 g (yield: 68%) of the product.

2. Synthesis Example of Sub 2-8

<Reaction Scheme 14>

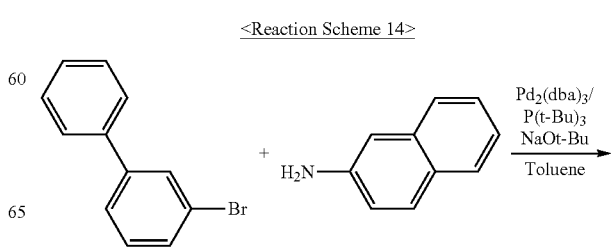

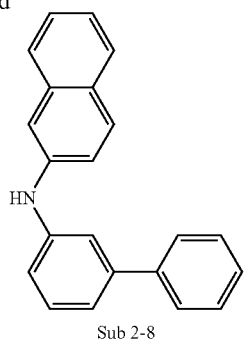

Sub 2-8

Naphthalen-2-amine (7.43 g, 51.86 mmol), Pd₂(dba)₃ (1.30 g, 1.41 mmol), 50% P(t-Bu)₃ (1.8 ml, 3.77 mmol), NaOt-Bu (13.59 g, 141.44 mmol), toluene (330 ml) were added to 3-bromo-1,1'-biphenyl (10.99 g, 47.15 mmol) obtained in the above synthesis, and then 11.14 g (yield: 80%) of the product was obtained by using the same manner as described above for the synthesis of Sub 2-4.

3. Synthesis Example of Sub 2-16

<Reaction Scheme 15>

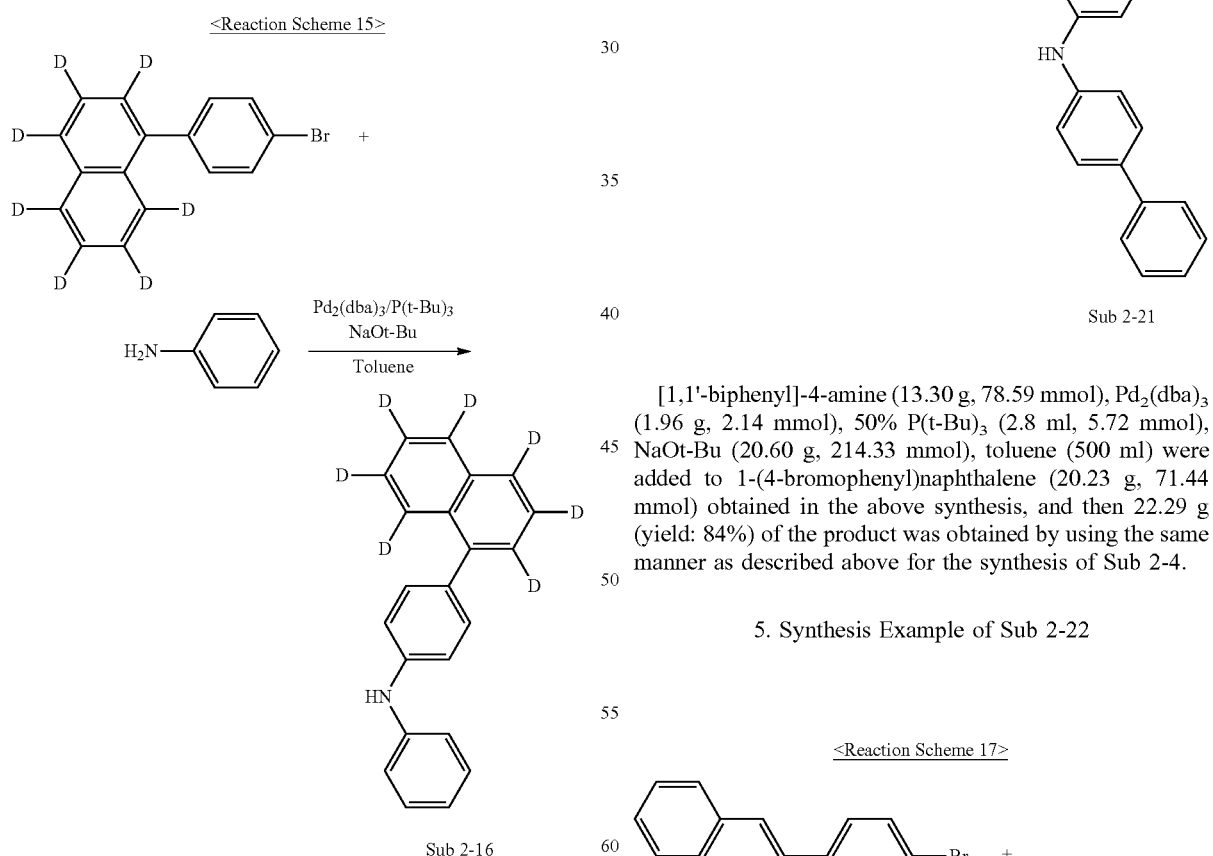

Sub 2-16

Aniline (3.79 g, 40.75 mmol), Pd₂(dba)₃ (1.02 g, 1.11 mmol), 50% P(t-Bu)₃ (1.4 ml, 2.96 mmol), NaOt-Bu (10.68 g, 111.13 mmol), toluene (260 ml) were added to naphthalene-1,2,3,4,5,6,7-d7,8-(4-bromophenyl)-(10.75 g, 37.04 mmol) obtained in the above synthesis, and then 8.18 g (yield: 73%) of the product was obtained by using the same manner as described above for the synthesis of Sub 2-4.

4. Synthesis Example of Sub 2-21

<Reaction Scheme 16>

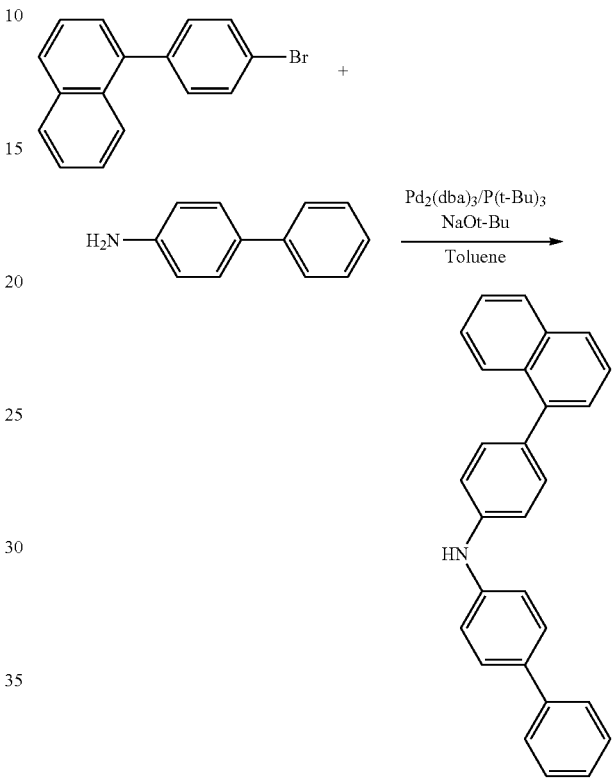

Sub 2-21

[1,1'-biphenyl]-4-amine (13.30 g, 78.59 mmol), Pd₂(dba)₃ (1.96 g, 2.14 mmol), 50% P(t-Bu)₃ (2.8 ml, 5.72 mmol), NaOt-Bu (20.60 g, 214.33 mmol), toluene (500 ml) were added to 1-(4-bromophenyl)naphthalene (20.23 g, 71.44 mmol) obtained in the above synthesis, and then 22.29 g (yield: 84%) of the product was obtained by using the same manner as described above for the synthesis of Sub 2-4.

5. Synthesis Example of Sub 2-22

<Reaction Scheme 17>

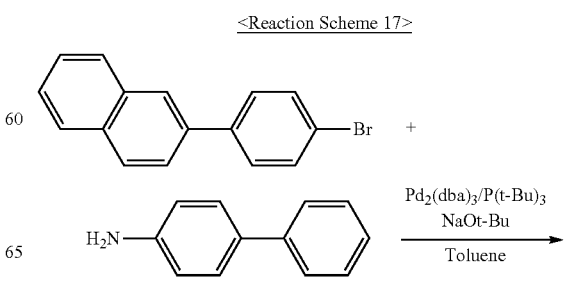

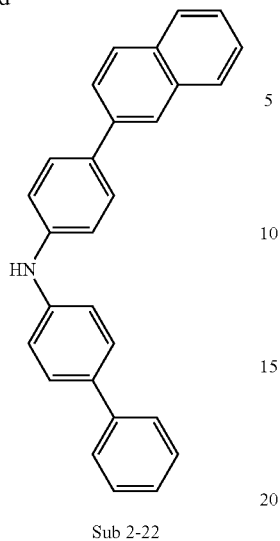

Sub 2-22

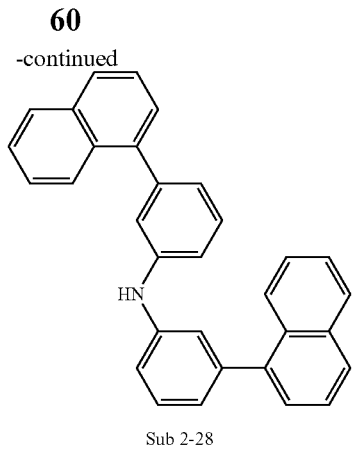

Sub 2-28

3-(naphthalen-1-yl)aniline (9.64 g, 43.98 mmol), Pd₂(dba)₃ (1.10 g, 1.20 mmol), 50% P(t-Bu)₃ (1.6 ml, 3.20 mmol), NaOt-Bu (11.53 g, 119.93 mmol), toluene (280 ml) were added to 1-(3-bromophenyl)naphthalene (11.32 g, 39.98 mmol) obtained in the above synthesis, and then 12.64 g (yield: 75%) of the product was obtained by using the same manner as described above for the synthesis of Sub 2-4.

7. Synthesis Example of Sub 2-32

[1,1'-biphenyl]-4-amine (6.63 g, 39.16 mmol), Pd₂(dba)₃ (0.98 g, 1.07 mmol), 50% P(t-Bu)₃ (1.4 ml, 2.85 mmol), NaOt-Bu (10.26 g, 106.79 mmol), toluene (250 ml) were added to 2-(4-bromophenyl)naphthalene (10.08 g, 35.60 mmol) obtained in the above synthesis, and then 10.71 g (yield: 81%) of the product was obtained by using the same manner as described above for the synthesis of Sub 2-4.

6. Synthesis Example of Sub 2-28

<Reaction Scheme 18>

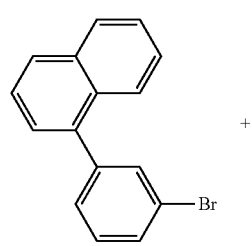

+

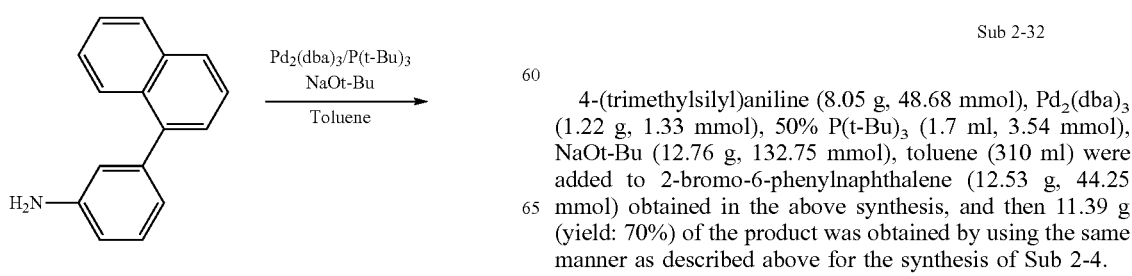

<Reaction Scheme 19>

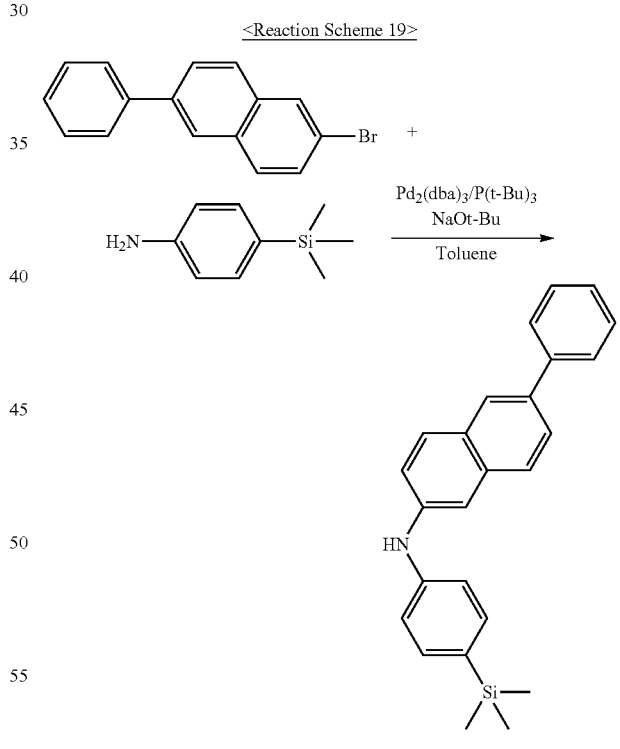

Sub 2-32

4-(trimethylsilyl)aniline (8.05 g, 48.68 mmol), Pd₂(dba)₃ (1.22 g, 1.33 mmol), 50% P(t-Bu)₃ (1.7 ml, 3.54 mmol), NaOt-Bu (12.76 g, 132.75 mmol), toluene (310 ml) were added to 2-bromo-6-phenylnaphthalene (12.53 g, 44.25 mmol) obtained in the above synthesis, and then 11.39 g (yield: 70%) of the product was obtained by using the same manner as described above for the synthesis of Sub 2-4.

The compound belonging to Sub 2 may be, but not limited to, the following compounds, and Table 2 shows FD-MS values of compounds belonging to Sub 2.
Sub 2-1
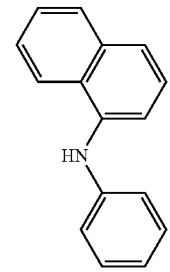
Sub 2-2
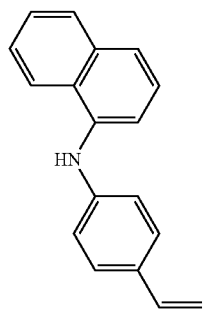
Sub 2-3
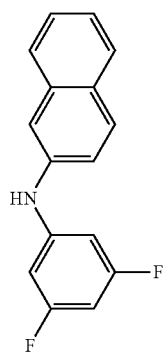
Sub 2-4
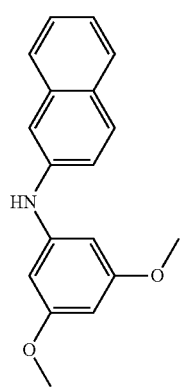
Sub 2-5
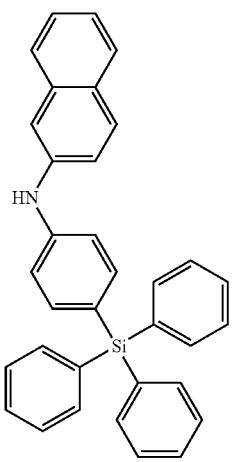
Sub 2-6
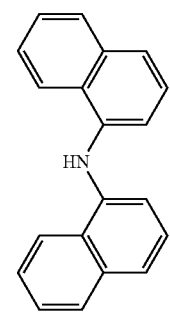
Sub 2-7
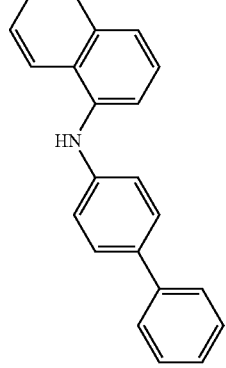
Sub 2-8
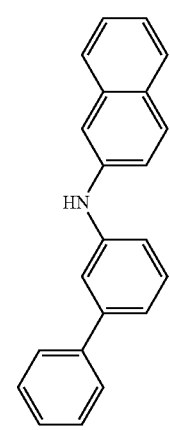

Sub 2-9
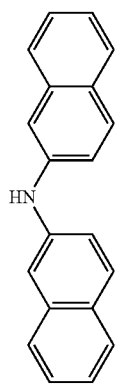
Sub 2-10
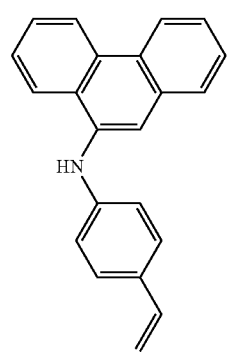
Sub 2-11
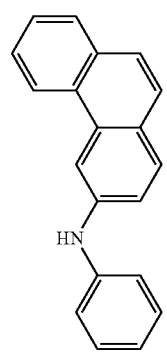
Sub 2-12
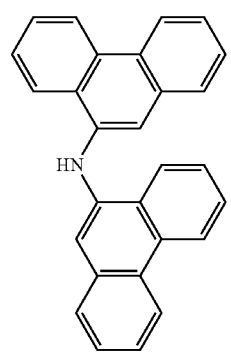
Sub 2-13
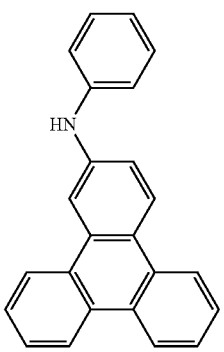
Sub 2-14
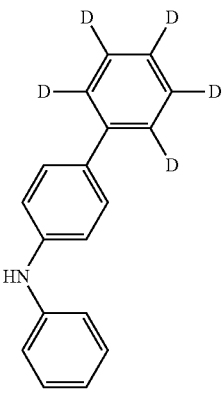
Sub 2-15
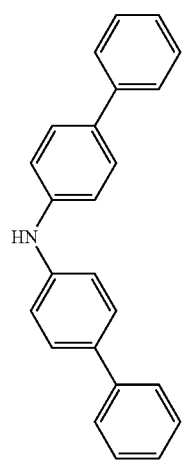
Sub 2-16
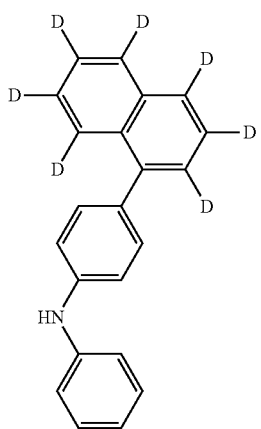

Sub 2-17
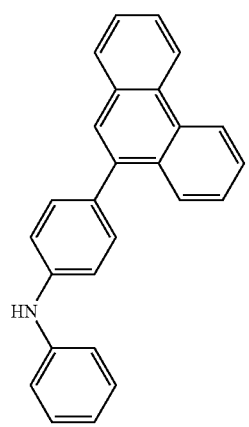
Sub 2-18
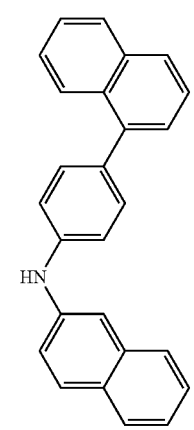
Sub 2-19
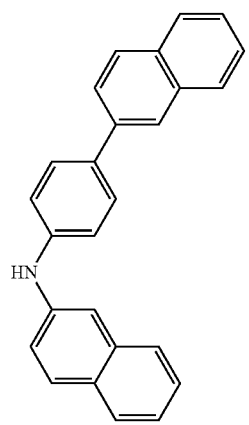
Sub 2-20
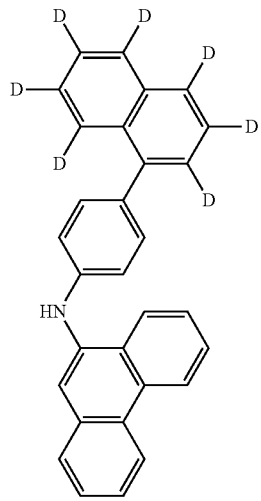
Sub 2-21
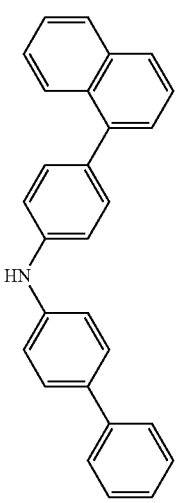
Sub 2-22
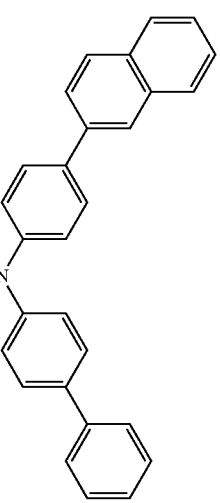

Sub 2-23
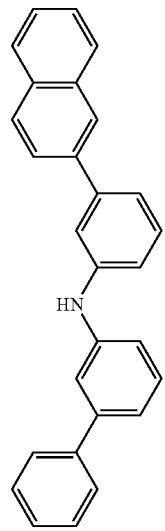
Sub 2-24
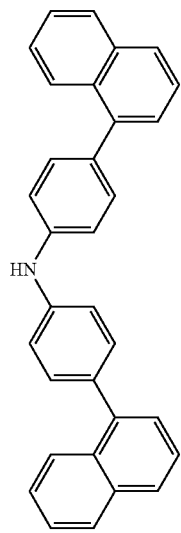
Sub 2-25
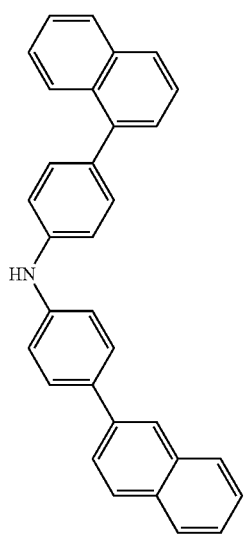
Sub 2-26
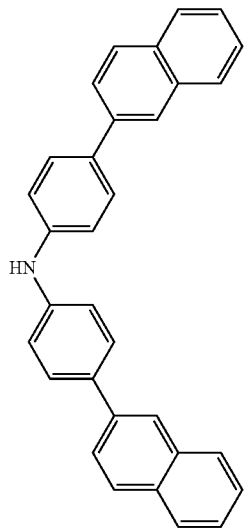
Sub 2-27
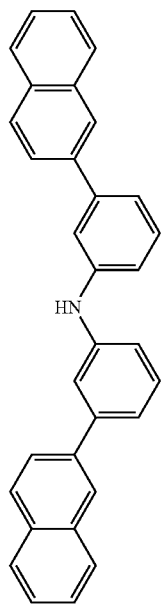
Sub 2-28
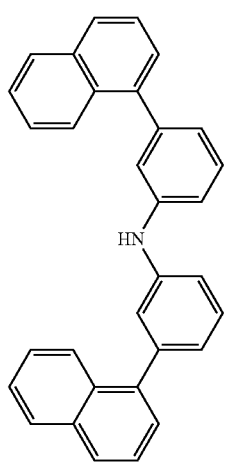

-continued
Sub 2-29
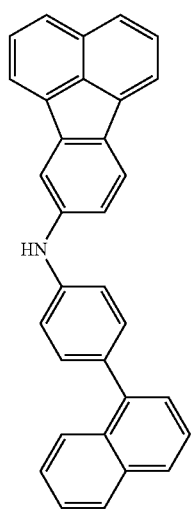
Sub 2-30
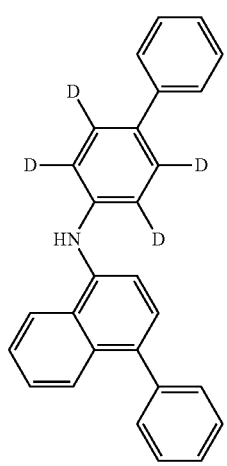
Sub 2-31
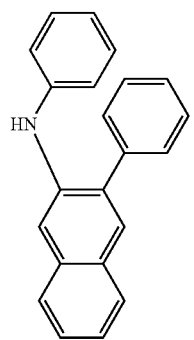
-continued
Sub 2-32
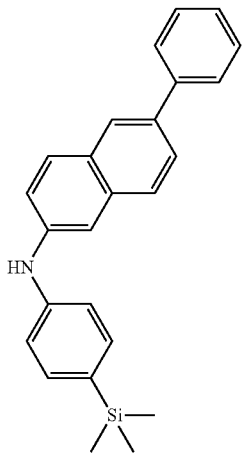
Sub 2-33
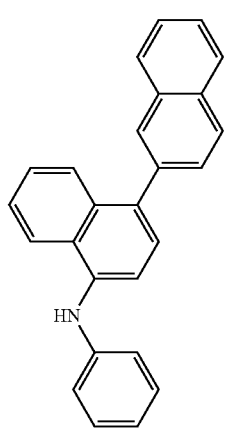
Sub 2-34
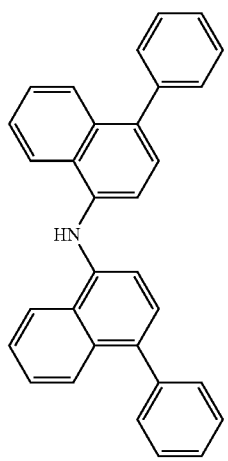

-continued

Sub 2-35

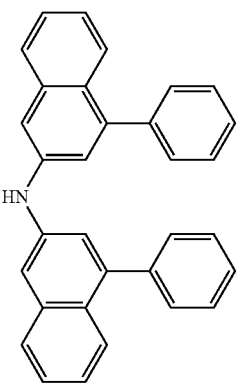

Sub 2-36

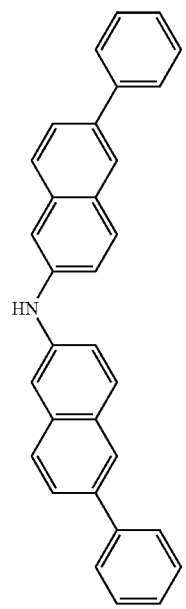

III. Synthesis of Final Products

Sub 1 (1 eq.) was dissolved in toluene in a round bottom flask, and Sub 2 (1 eq.), Pd$_2$(dba)$_3$ (0.03 eq.), P(t-Bu)$_3$ (0.08 eq.) and NaOt-Bu (3 eq.) were added, then, stirring at 100° C. was followed. When the reaction was completed, the reaction product was extracted with CH$_2$Cl$_2$ and water, and then the organic layer was dried with MgSO$_4$ and concentrated. Then, the concentrate was passed through silica gel column and recrystallized to obtain final product.

1. Synthesis Example of P-3

<Reaction Scheme 20>

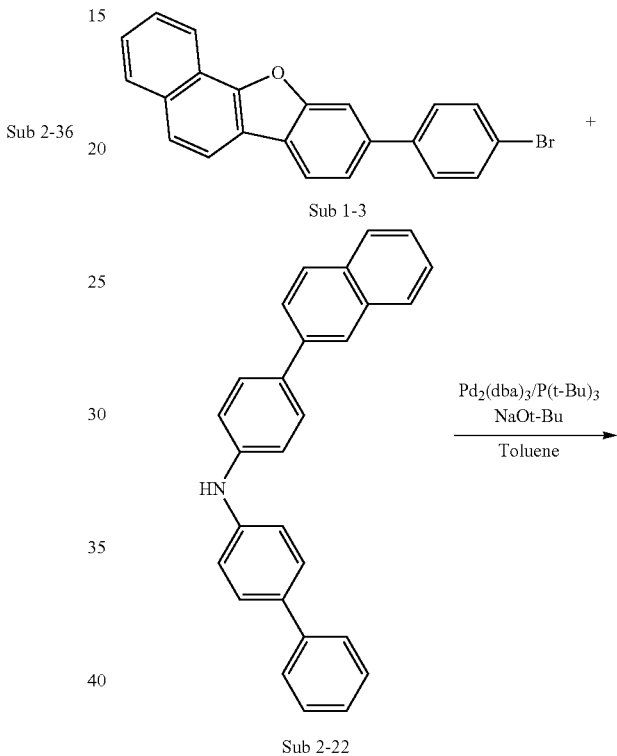

TABLE 2

| compound | FD-MS | compound | FD-MS |
|---|---|---|---|
| Sub 2-1 | m/z = 219.10(C$_{16}$H$_{13}$N = 219.28) | Sub 2-2 | m/z = 245.12(C$_{18}$H$_{15}$N = 245.32) |
| Sub 2-3 | m/z = 255.09(C$_{16}$H$_{11}$F$_2$N = 255.26) | Sub 2-4 | m/z = 279.13(C$_{18}$H$_{27}$NO$_2$ = 279.33) |
| Sub 2-5 | m/z = 477.19(C$_{34}$H$_{27}$NSi = 477.67) | Sub 2-6 | m/z = 269.12(C$_{20}$H$_{15}$N = 269.34) |
| Sub 2-7 | m/z = 295.14(C$_{22}$H$_{17}$N = 295.38) | Sub 2-8 | m/z = 295.14(C$_{22}$H$_{17}$N = 295.38) |
| Sub 2-9 | m/z = 269.12(C$_{20}$H$_{15}$N = 269.34) | Sub 2-10 | m/z = 295.14(C$_{22}$H$_{17}$N = 295.38) |
| Sub 2-11 | m/z = 269.12(C$_{20}$H$_{15}$N = 269.34) | Sub 2-12 | m/z = 369.15(C$_{28}$H$_{19}$N = 369.46) |
| Sub 2-13 | m/z = 319.14(C$_{24}$H$_{17}$N = 319.40) | Sub 2-14 | m/z = 250.15(C$_{18}$H$_{10}$D$_5$N = 250.35) |
| Sub 2-15 | m/z = 321.15(C$_{24}$H$_{19}$N = 321.41) | Sub 2-16 | m/z = 302.18(C$_{22}$H$_{10}$D$_7$N = 302.42) |
| Sub 2-17 | m/z = 345.15(C$_{26}$H$_{19}$N = 345.44) | Sub 2-18 | m/z = 345.15(C$_{26}$H$_{19}$N = 345.44) |
| Sub 2-19 | m/z = 345.15(C$_{26}$H$_{19}$N = 345.44) | Sub 2-20 | m/z = 402.21(C$_{30}$H$_{14}$D$_7$N = 402.54) |
| Sub 2-21 | m/z = 371.17(C$_{28}$H$_{21}$N = 371.47) | Sub 2-22 | m/z = 371.17(C$_{28}$H$_{21}$N = 371.47) |
| Sub 2-23 | m/z = 371.17(C$_{28}$H$_{21}$N = 371.47) | Sub 2-24 | m/z = 421.18(C$_{32}$H$_{23}$N = 421.53) |
| Sub 2-25 | m/z = 421.18(C$_{32}$H$_{23}$N = 421.53) | Sub 2-26 | m/z = 421.18(C$_{32}$H$_{23}$N = 421.53) |
| Sub 2-27 | m/z = 421.18(C$_{32}$H$_{23}$N = 421.53) | Sub 2-28 | m/z = 421.18(C$_{32}$H$_{23}$N = 421.53) |
| Sub 2-29 | m/z = 419.17(C$_{32}$H$_{21}$N = 419.52) | Sub 2-30 | m/z = 375.19(C$_{28}$H$_{17}$D$_4$N = 375.50) |
| Sub 2-31 | m/z = 295.14(C$_{22}$H$_{17}$N = 295.38) | Sub 2-32 | m/z = 367.18(C$_{25}$H$_{25}$NSi = 367.56) |
| Sub 2-33 | m/z = 345.15(C$_{26}$H$_{19}$N = 345.44) | Sub 2-34 | m/z = 421.18(C$_{32}$H$_{23}$N = 421.53) |
| Sub 2-35 | m/z = 421.18(C$_{32}$H$_{23}$N = 421.53) | Sub 2-36 | m/z = 421.18(C$_{32}$H$_{23}$N = 421.53) |

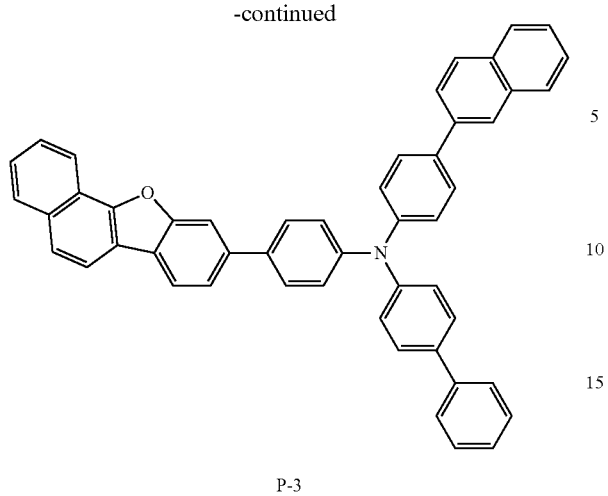

P-3

Sub 1-3 (5.11 g, 13.69 mmol) obtained in the above synthesis was dissolved in toluene (140 ml) in a round bottom flask, and Sub 2-22 (5.09 g, 13.69 mmol), Pd₂(dba)₃ (0.38 g, 0.41 mmol), 50% P(t-Bu)₃ (0.5 ml, 1.10 mmol), NaOt-Bu (3.95 g, 41.07 mmol) were added, then, stirring at 100° C. was followed. When the reaction was completed, the reaction product was extracted with CH₂Cl₂ and water, and then the organic layer was dried with MgSO₄ and concentrated. Then, the concentrate was passed through silica gel column and recrystallized to obtain 7.82 g (yield: 86%) of product.

2. Synthesis Example of P-12

<Reaction Scheme 21>

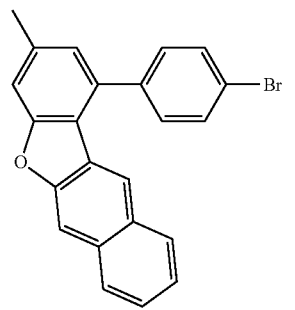

Sub 1-9

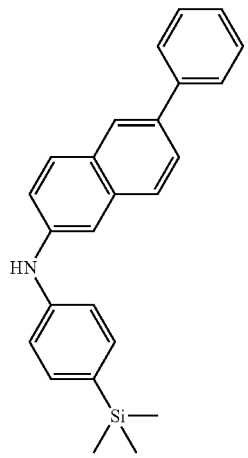

Sub 2-32

$\xrightarrow{\text{Pd}_2(\text{dba})_3/\text{P(t-Bu)}_3 \text{ NaOt-Bu}}_{\text{Toluene}}$

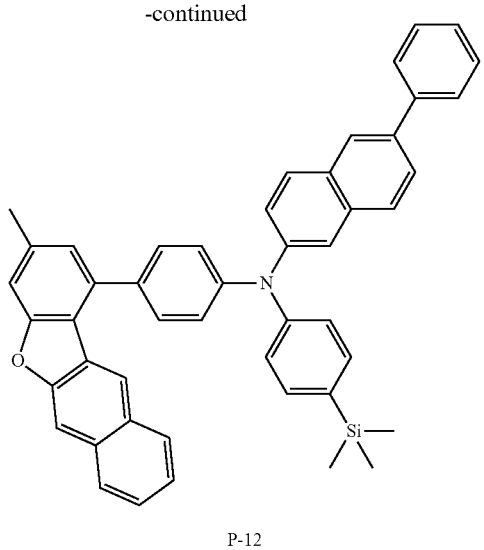

P-12

Sub 2-32 (5.55 g, 15.11 mmol), Pd₂(dba)₃ (0.41 g, 0.45 mmol), 50% P(t-Bu)₃ (0.6 ml, 1.21 mmol), NaOt-Bu (4.36 g, 45.32 mmol), toluene (150 ml) were added to Sub 1-9 (5.85 g, 15.11 mmol) obtained in the above synthesis, and then 7.63 g (yield: 75%) of the product was obtained by using the same manner as described above for the synthesis of the compound P-3.

3. Synthesis Example of P-20

<Reaction Scheme 22>

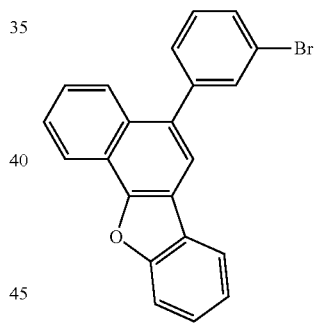

Sub 1-15

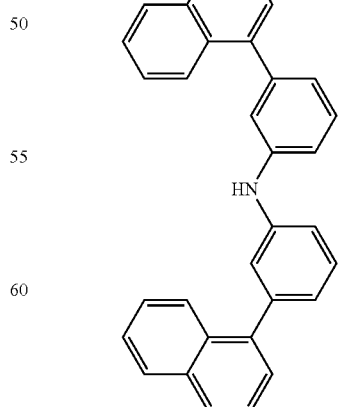

Sub 2-28

$\xrightarrow{\text{Pd}_2(\text{dba})_3/\text{P(t-Bu)}_3 \text{ NaOt-Bu}}_{\text{Toluene}}$

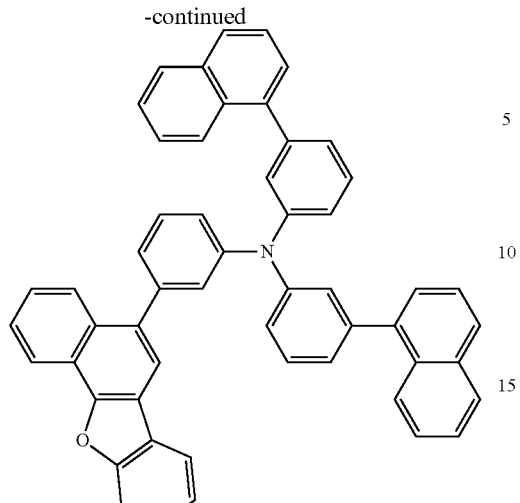

P-20

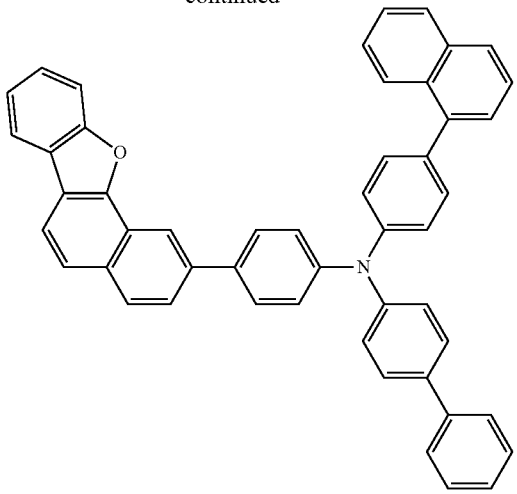

P-24

Sub 2-28 (5.92 g, 14.04 mmol), Pd$_2$(dba)$_3$ (0.39 g, 0.42 mmol), 50% P(t-Bu)$_3$ (0.5 ml, 1.12 mmol), NaOt-Bu (4.05 g, 42.12 mmol), toluene (140 ml) were added to Sub 1-15 (5.24 g, 14.04 mmol) obtained in the above synthesis, and then 7.32 g (yield: 73%) of the product was obtained by using the same manner as described above for the synthesis of the compound P-3.

Sub 2-21 (4.84 g, 13.02 mmol), Pd$_2$(dba)$_3$ (0.36 g, 0.39 mmol), 50% P(t-Bu)$_3$ (0.5 ml, 1.04 mmol), NaOt-Bu (3.75 g, 39.06 mmol), toluene (130 ml) were added to Sub 1-18 (4.86 g, 13.02 mmol) obtained in the above synthesis, and then 7.61 g (yield: 88%) of the product was obtained by using the same manner as described above for the synthesis of the compound P-3.

4. Synthesis Example of P-24

<Reaction Scheme 23>

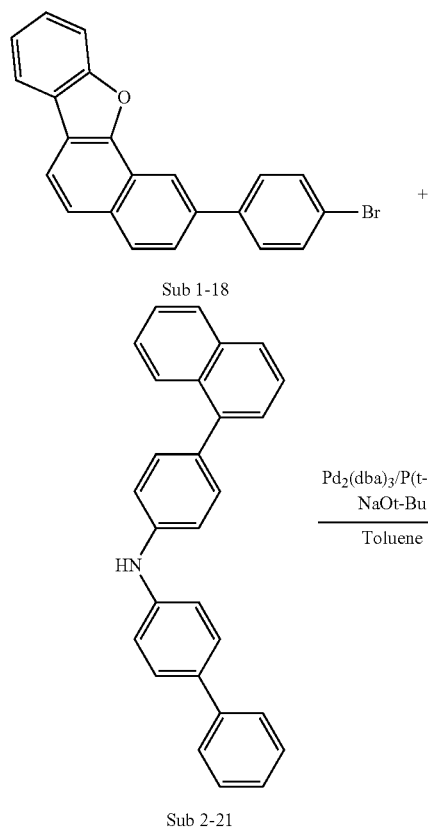

5. Synthesis Example of P-28

<Reaction Scheme 24>

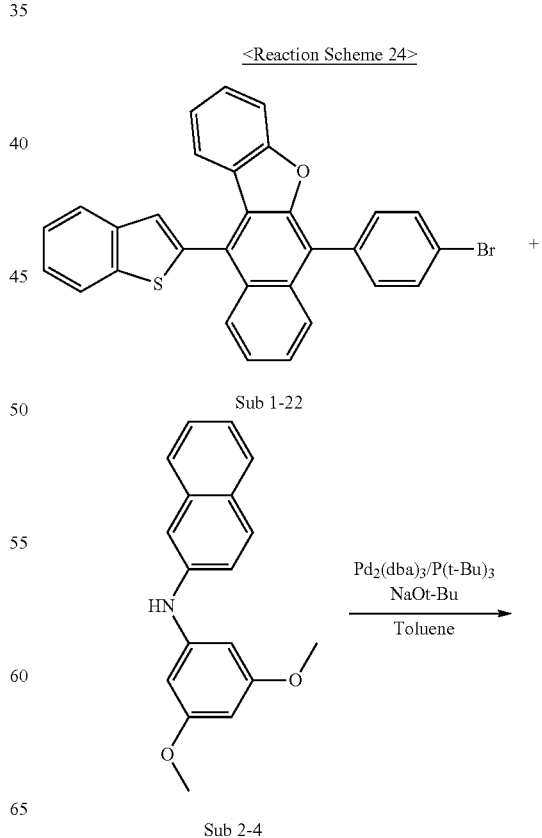

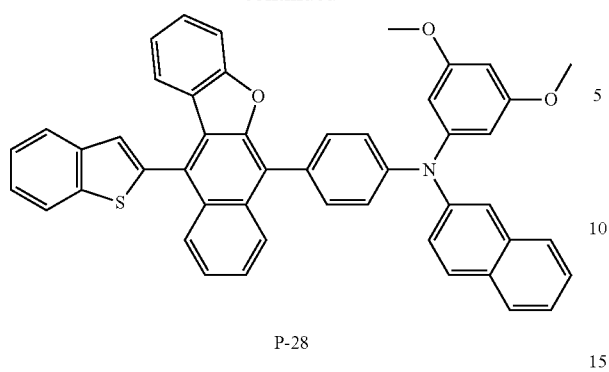

P-28

Sub 2-4 (4.22 g, 15.12 mmol), Pd$_2$(dba)$_3$ (0.42 g, 0.45 mmol), 50% P(t-Bu)$_3$ (0.6 ml, 1.21 mmol), NaOt-Bu (4.36 g, 45.35 mmol), toluene (150 ml) were added to Sub 1-22 (7.64 g, 15.12 mmol) obtained in the above synthesis, and then 7.45 g (yield: 70%) of the product was obtained by using the same manner as described above for the synthesis of the compound P-3.

6. Synthesis Example of P-34

<Reaction Scheme 25>

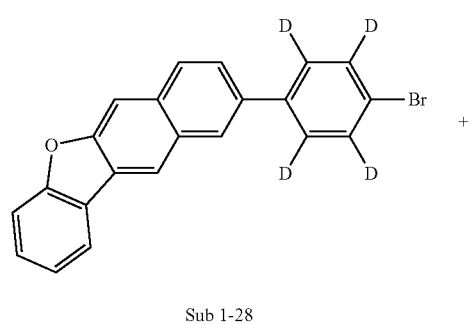

Sub 1-28

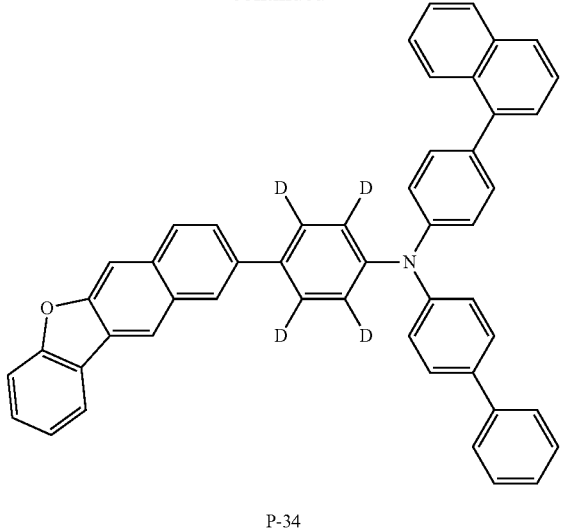

P-34

Sub 2-21 (5.19 g, 13.97 mmol), Pd$_2$(dba)$_3$ (0.38 g, 0.42 mmol), 50% P(t-Bu)$_3$ (0.5 ml, 1.12 mmol), NaOt-Bu (4.03 g, 41.91 mmol), toluene (140 ml) were added to Sub 1-28 (5.27 g, 13.97 mmol) obtained in the above synthesis, and then 7.18 g (yield: 77%) of the product was obtained by using the same manner as described above for the synthesis of the compound P-3.

7. Synthesis Example of P-36

<Reaction Scheme 26>

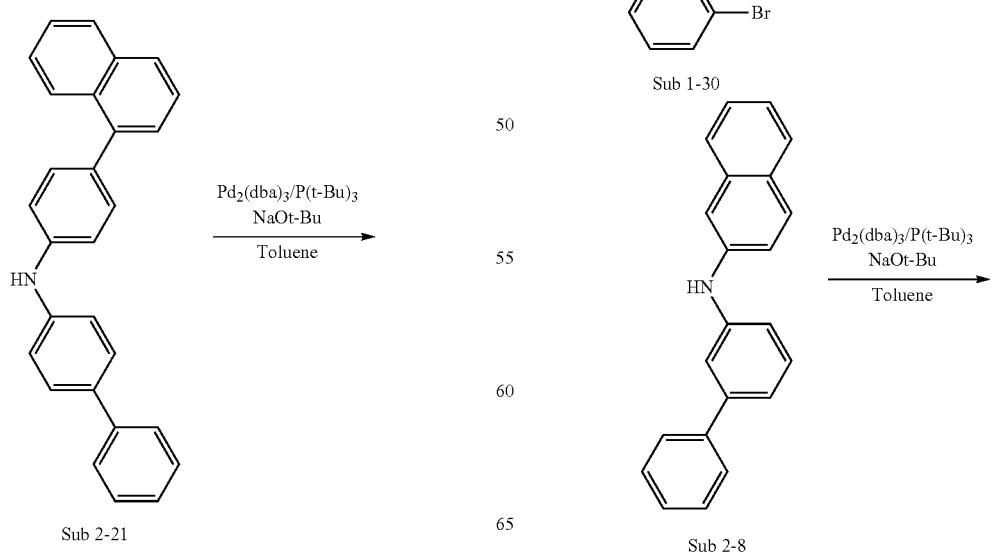

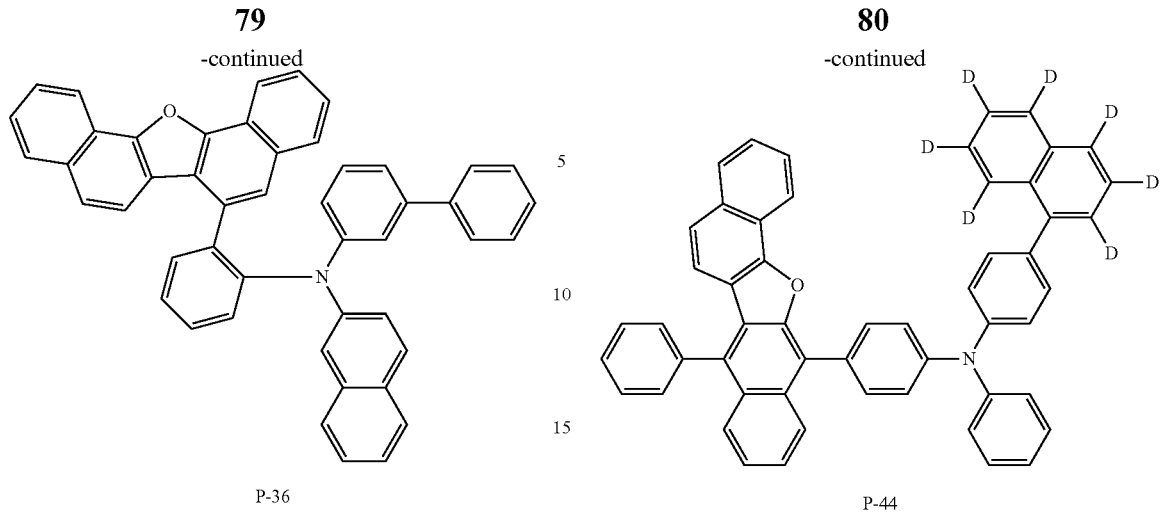

P-36

P-44

Sub 2-8 (5.62 g, 19.04 mmol), Pd$_2$(dba)$_3$ (0.52 g, 0.57 mmol), 50% P(t-Bu)$_3$ (0.7 ml, 1.52 mmol), NaOt-Bu (5.49 g, 57.12 mmol), toluene (190 ml) were added to Sub 1-30 (8.06 g, 19.04 mmol) obtained in the above synthesis, and then 7.77 g (yield: 64%) of the product was obtained by using the same manner as described above for the synthesis of the compound P-3.

8. Synthesis Example of P-44

Sub 2-16 (3.95 g, 13.06 mmol), Pd$_2$(dba)$_3$ (0.36 g, 0.39 mmol), 50% P(t-Bu)$_3$ (0.5 ml, 1.04 mmol), NaOt-Bu (3.76 g, 39.17 mmol), toluene (130 ml) were added to Sub 1-38 (6.52 g, 13.06 mmol) obtained in the above synthesis, and then 7.72 g (yield: 82%) of the product was obtained by using the same manner as described above for the synthesis of the compound P-3.

9. Synthesis Example of P-47

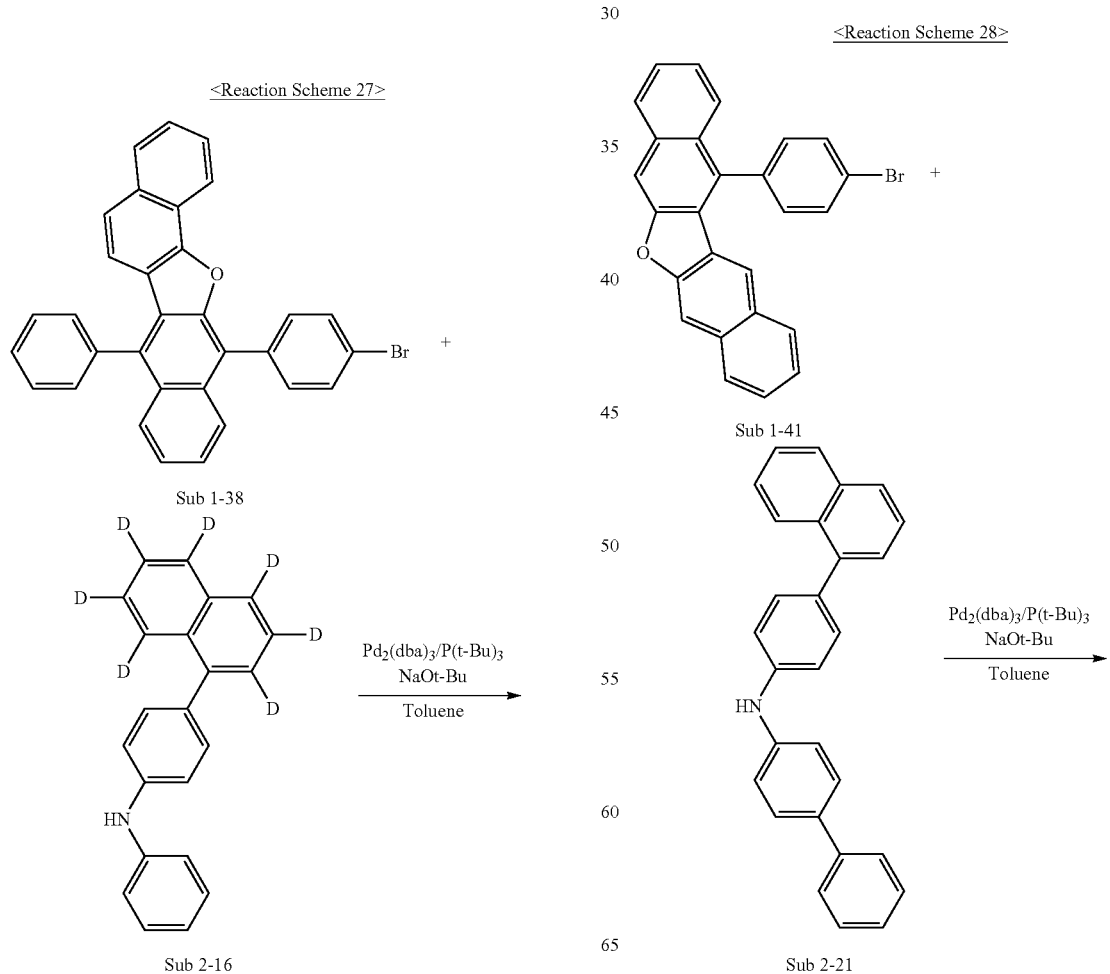

-continued

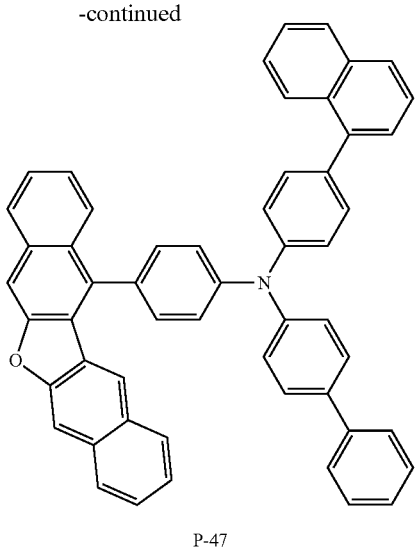

P-47

Sub 2-21 (4.50 g, 12.12 mmol), Pd$_2$(dba)$_3$ (0.33 g, 0.36 mmol), 50% P(t-Bu)$_3$ (0.5 ml, 0.97 mmol), NaOt-Bu (3.49 g, 36.36 mmol), toluene (120 ml) were added to Sub Sub 1-41 (5.13 g, 12.12 mmol) obtained in the above synthesis, and then 7.35 g (yield: 85%) of the product was obtained by using the same manner as described above for the synthesis of the compound P-3.

The FD-MS values of compounds P-1 to P-48 of the present invention prepared according to the above synthesis examples are shown in Table 3 below.

TABLE 3

| compound | FD-MS | compound | FD-MS |
| --- | --- | --- | --- |
| P-1 | m/z = 713.27($C_{54}H_{35}NO$ = 713.86) | P-2 | m/z = 737.27($C_{56}H_{35}NO$ = 737.88) |
| P-3 | m/z = 663.26($C_{50}H_{33}NO$ = 663.80) | P-4 | m/z = 694.30($C_{52}H_{26}D_7NO$ = 694.87) |
| P-5 | m/z = 663.26($C_{50}H_{33}NO$ = 663.80) | P-6 | m/z = 713.27($C_{54}H_{35}NO$ = 713.86) |
| P-7 | m/z = 713.27($C_{54}H_{35}NO$ = 713.86) | P-8 | m/z = 763.29($C_{58}H_{37}NO$ = 763.92) |
| P-9 | m/z = 587.22($C_{44}H_{29}NO$ = 587.71) | P-10 | m/z = 667.28($C_{50}H_{29}D_4NO$ = 667.83) |
| P-11 | m/z = 713.27($C_{54}H_{35}NO$ = 713.86) | P-12 | m/z = 673.28($C_{48}H_{39}NOSi$ = 673.91) |
| P-13 | m/z = 677.24($C_{50}H_{31}NO_2$ = 677.79) | P-14 | m/z = 689.27($C_{52}H_{35}NO$ = 689.84) |
| P-15 | m/z = 663.26($C_{50}H_{33}NO$ = 663.80) | P-16 | m/z = 711.26($C_{54}H_{33}NO$ = 711.85) |
| P-17 | m/z = 661.24($C_{50}H_{31}NO$ = 661.79) | P-18 | m/z = 663.26($C_{50}H_{33}NO$ = 663.80) |
| P-19 | m/z = 713.27($C_{54}H_{35}NO$ = 713.86) | P-20 | m/z = 713.27($C_{54}H_{35}NO$ = 713.86) |
| P-21 | m/z = 617.27($C_{46}H_{35}NO$ = 617.78) | P-22 | m/z = 623.30($C_{46}H_{21}D_{10}NO$ = 623.81) |
| P-23 | m/z = 613.24($C_{46}H_{31}NO$ = 613.74) | P-24 | m/z = 663.26($C_{50}H_{33}NO$ = 663.80) |
| P-25 | m/z = 663.26($C_{50}H_{33}NO$ = 663.80) | P-26 | m/z = 687.26($C_{52}H_{33}NO$ = 687.82) |
| P-27 | m/z = 637.24($C_{48}H_{31}NO$ = 637.77) | P-28 | m/z = 703.22($C_{48}H_{33}NO_3S$ = 703.85) |
| P-29 | m/z = 689.27($C_{52}H_{35}NO$ = 689.84) | P-30 | m/z = 662.24($C_{49}H_{30}N_2O$ = 662.78) |
| P-31 | m/z = 713.27($C_{54}H_{35}NO$ = 713.86) | P-32 | m/z = 587.22($C_{44}H_{29}NO$ = 587.71) |
| P-33 | m/z = 687.26($C_{52}H_{33}NO$ = 687.82) | P-34 | m/z = 667.28($C_{50}H_{29}D_4NO$ = 667.83) |
| P-35 | m/z = 763.29($C_{58}H_{37}NO$ = 763.92) | P-36 | m/z = 637.24($C_{48}H_{31}NO$ = 637.77) |
| P-37 | m/z = 687.26($C_{52}H_{33}NO$ = 687.82) | P-38 | m/z = 774.25($C_{55}H_{32}F_2N_2O$ = 774.85) |
| P-39 | m/z = 713.27($C_{54}H_{35}NO$ = 713.86) | P-40 | m/z = 713.27($C_{54}H_{35}NO$ = 713.86) |
| P-41 | m/z = 687.26($C_{52}H_{33}NO$ = 687.82) | P-42 | m/z = 847.33($C_{62}H_{45}NOSi$ = 848.11) |
| P-43 | m/z = 687.26($C_{52}H_{33}NO$ = 687.82) | P-44 | m/z = 720.32($C_{54}H_{28}D_7NO$ = 720.90) |
| P-45 | m/z = 661.24($C_{50}H_{31}NO$ = 661.79) | P-46 | m/z = 711.26($C_{54}H_{33}NO$ = 711.85) |
| P-47 | m/z = 713.27($C_{54}H_{35}NO$ = 713.86) | P-48 | m/z = 767.31($C_{58}H_{33}D_4NO$ = 767.95) |

In the above, even though an exemplary synthesis example of the present invention represented by the Formula 1 are described, all of them are based on Buchwald-Hartwig cross coupling reaction, Pd(II)-catalyzed oxidative cyclization reaction (Org. Lett. 2011, 13, 5504), Miyaura boration reaction and Suzuki cross-coupling reaction. Therefore, it will be understood by those skilled in the art that the above reaction proceeds even when other substituents (substituents of A ring, B ring, $L^1$ to $L^3$, $Ar^1$, $Ar^2$ and the like) defined in Formula 1 are bonded, in addition to the substituents described in the specific synthesis example.

For example, the reaction of Sub 1 and Sub 2→Final Product in Reaction Scheme 1, and the reaction of starting material→Sub 2 in Reaction Scheme 12 are based on Buchwald-Hartwig cross coupling reaction, the reaction of starting material→Sub 1-I in Reaction Scheme 2 is based on Pd(II)-catalyzed oxidative cyclization reaction, and the reaction of Sub 1-I→Sub 1-II in Reaction Scheme 2 is based on Miyaura boration reaction. Further, the reaction of Sub 1-II→Sub 1 in Reaction Scheme 2 is based on Suzuki cross-coupling reaction. The above reactions will proceed even if a substituent not specifically mentioned is attached.

Fabrication and Evaluation of Organic Electronic Element

[Example I-1] Green OLED (A Hole Transport Layer

Organic light emitting diodes (OLEDs) were fabricated according to a conventional method by using a compound of the present invention as a hole transport layer material.

First, an ITO layer (anode) was formed on a glass substrate, and then 4,4',4"-tris[2-naphthyl(phenyl)amino]triphenylamine (hereinafter, "2-TNATA") was vacuum-deposited on the ITO layer to form a hole injection layer with a thickness of 60 nm.

Subsequently, compound P-1 of the present invention was vacuum-deposited with a thickness of 60 nm on the hole injection layer to form a hole transport layer.

Subsequently, a light emitting layer with a thickness of 30 nm was formed on the hole transport layer by using 4,4'-N, N'-dicarbazole-biphenyl (hereinafter, "CBP") as a host material and tris(2-phenylpyridine)-iridium (hereinafter, "Ir (ppy)$_3$") as a dopant material in a weight ratio of 90:10.

Next, ((1,1'-bisphenyl)-4-olato)bis(2-methyl-8-quinolinolato)aluminum (hereinafter, "BAlq") was vacuum-deposited with a thickness of 10 nm on the light emitting layer to form a hole blocking layer, and tris(8-quinolinolato)aluminum (hereinafter, "Alq$_3$") was formed with a thickness of 40 nm to form an electron transport layer.

Next, halogenated alkali metal LiF was deposited with a thickness of 0.2 nm on the electron transport layer to form an electron injection layer, and then Al was deposited with a thickness of 150 nm on the electron injection layer to form a cathode. In this way, the OLED was completed.

[Example I-2] to [Example I-34] Green OLED (A Hole Transport Layer

The OLEDs were fabricated in the same manner as described in Example I-1 except that the compounds P-3 to P-48 of the present invention described in Table 4 instead of the compound P-1 of the present invention were used as the hole transport layer material.

[Comparative Example I-1] to [Comparative Example I-8]

The OLEDs were fabricated in the same manner as described in Example 1 except that the following Comparative Compounds 1 to 8 instead of the compound P-1 of the present invention were each used as the hole transport layer material.

<Comp.compd 1>

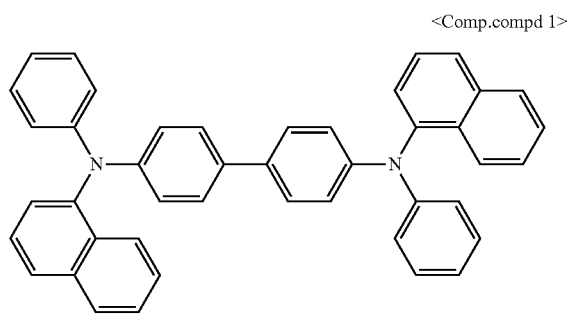

<Comp.compd 2>

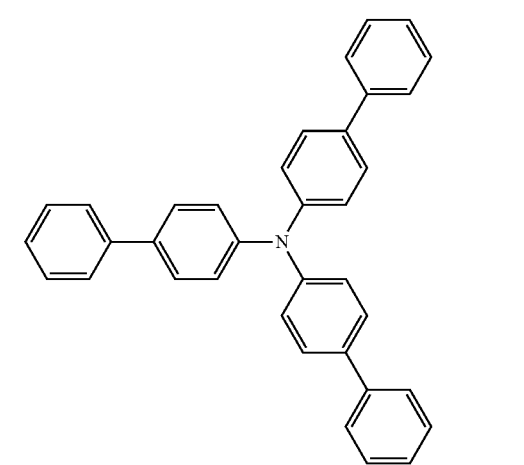

<Comp.compd 3>

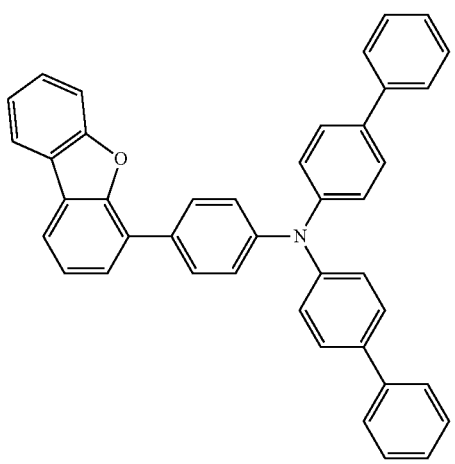

<Comp.compd 4>

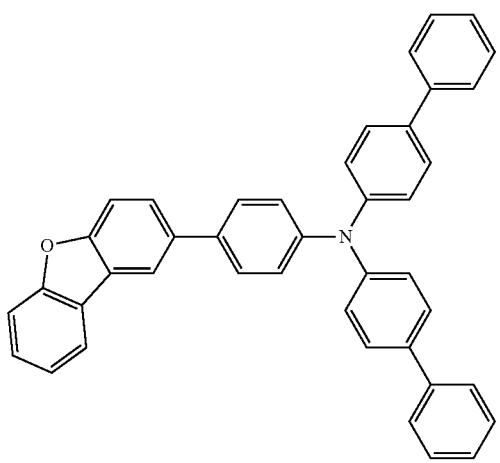

<Comp.compd 5>

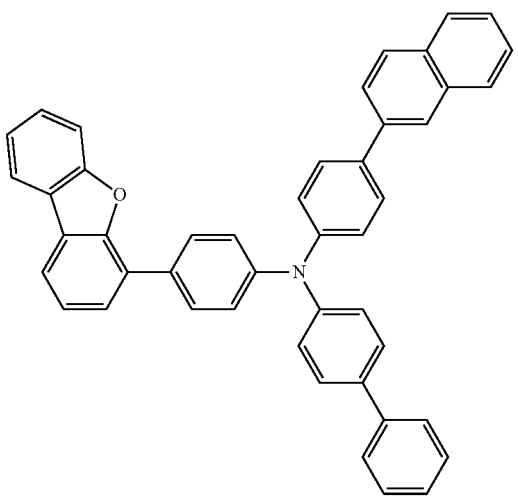

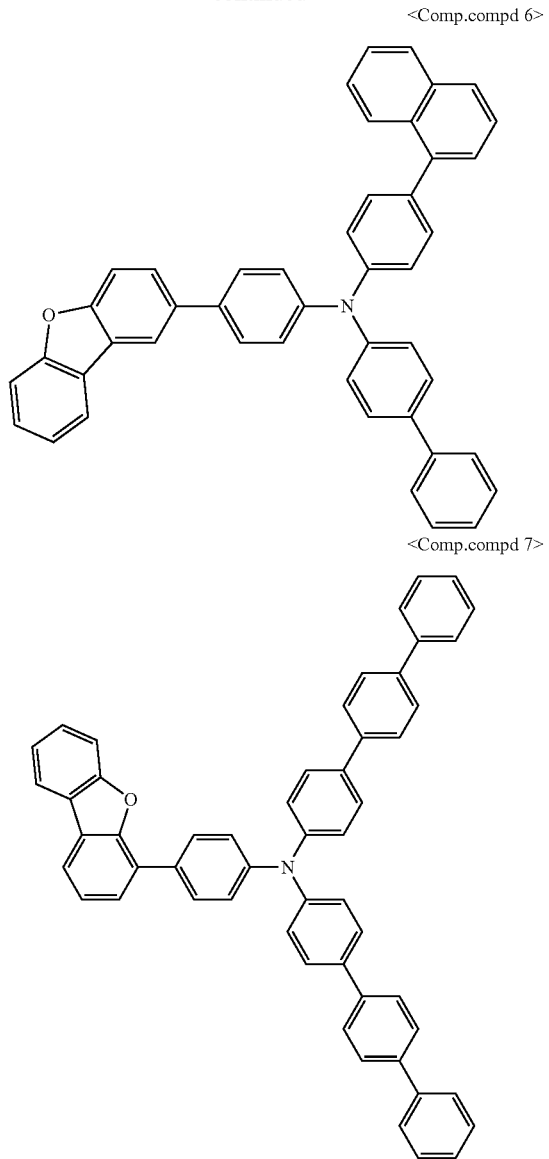

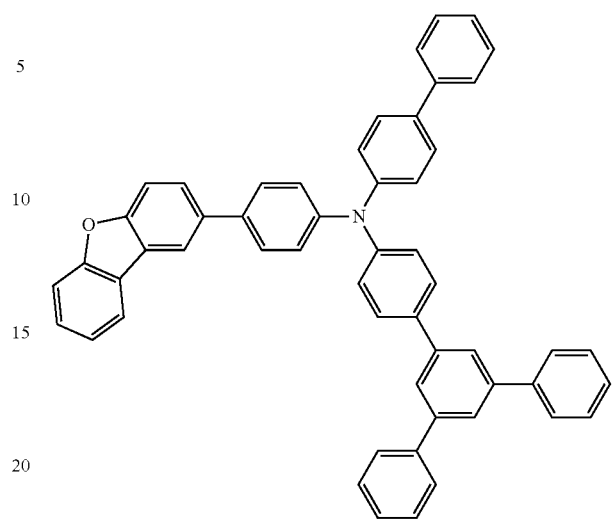

Electroluminescence (EL) characteristics were measured with a PR-650 (Photoresearch) by applying a forward bias DC voltage to the OLEDs prepared in Examples I-1 to I-34 of the present invention and Comparative Examples I-1 to I-8. And, the T95 life time was measured using a life time measuring apparatus manufactured by Macscience Inc. at reference brightness of 5000 cd/m². The measurement results are shown in Table 4 below.

TABLE 4

| | compound | Voltage (V) | Current Density (mA/cm²) | Brightness (cd/m²) | Efficiency (cd/A) | Lifetime T(95) | CIE x | CIE y |
|---|---|---|---|---|---|---|---|---|
| comp. Ex(I-1) | comp. Com1 | 6.0 | 21.5 | 5000 | 23.3 | 57.2 | 0.32 | 0.61 |
| comp. Ex(I-2) | comp. Com2 | 5.9 | 19.9 | 5000 | 25.1 | 69.6 | 0.32 | 0.62 |
| comp. Ex(I-3) | comp. Com3 | 5.9 | 17.6 | 5000 | 28.4 | 76.5 | 0.33 | 0.62 |
| comp. Ex(I-4) | comp. Com4 | 5.8 | 17.8 | 5000 | 28.1 | 76.5 | 0.33 | 0.62 |
| comp. Ex(I-5) | comp. Com5 | 5.8 | 15.4 | 5000 | 32.4 | 84.2 | 0.33 | 0.61 |
| comp. Ex(I-6) | comp. Com6 | 5.8 | 15.5 | 5000 | 32.3 | 82.3 | 0.33 | 0.62 |
| comp. Ex(I-7) | comp. Com7 | 5.9 | 18.5 | 5000 | 27.1 | 72.0 | 0.33 | 0.61 |
| comp. Ex(I-8) | comp. Com8 | 5.9 | 18.4 | 5000 | 27.2 | 72.6 | 0.33 | 0.61 |
| Ex.(I-1) | Com.(P-1) | 5.5 | 13.1 | 5000 | 38.1 | 139.1 | 0.33 | 0.61 |
| Ex.(I-2) | Com.(P-3) | 5.6 | 12.8 | 5000 | 39.1 | 141.9 | 0.33 | 0.62 |
| Ex.(I-3) | Com.(P-4) | 5.5 | 13.3 | 5000 | 37.5 | 137.4 | 0.33 | 0.62 |
| Ex.(I-4) | Com.(P-5) | 5.5 | 12.5 | 5000 | 39.9 | 147.3 | 0.33 | 0.61 |
| Ex.(I-5) | Com.(P-6) | 5.6 | 13.1 | 5000 | 38.3 | 140.9 | 0.33 | 0.61 |
| Ex.(I-6) | Com.(P-7) | 5.5 | 13.2 | 5000 | 38.0 | 140.3 | 0.33 | 0.61 |
| Ex.(I-7) | Com.(P-9) | 5.6 | 13.7 | 5000 | 36.5 | 133.2 | 0.33 | 0.61 |
| Ex.(I-8) | Com.(P-10) | 5.7 | 13.7 | 5000 | 36.5 | 135.5 | 0.33 | 0.62 |
| Ex.(I-9) | Com.(P-11) | 5.6 | 13.6 | 5000 | 36.7 | 135.4 | 0.33 | 0.61 |

TABLE 4-continued

|  | compound | Voltage (V) | Current Density (mA/cm²) | Brightness (cd/m²) | Efficiency (cd/A) | Lifetime T(95) | CIE x | CIE y |
|---|---|---|---|---|---|---|---|---|
| Ex.(I-10) | Com.(P-13) | 5.6 | 13.9 | 5000 | 36.1 | 137.0 | 0.33 | 0.62 |
| Ex.(I-11) | Com.(P-15) | 5.6 | 13.2 | 5000 | 37.8 | 139.9 | 0.33 | 0.61 |
| Ex.(I-12) | Com.(P-16) | 5.6 | 13.7 | 5000 | 36.6 | 134.0 | 0.33 | 0.61 |
| Ex.(I-13) | Com.(P-17) | 5.6 | 13.6 | 5000 | 36.7 | 135.8 | 0.33 | 0.61 |
| Ex.(I-14) | Com.(P-18) | 5.6 | 13.1 | 5000 | 38.3 | 136.6 | 0.33 | 0.61 |
| Ex.(I-15) | Com.(P-19) | 5.7 | 14.2 | 5000 | 35.2 | 132.7 | 0.33 | 0.61 |
| Ex.(I-16) | Com.(P-20) | 5.6 | 14.1 | 5000 | 35.4 | 128.4 | 0.33 | 0.62 |
| Ex.(I-17) | Com.(P-21) | 5.7 | 14.5 | 5000 | 34.4 | 128.2 | 0.33 | 0.62 |
| Ex.(I-18) | Com.(P-22) | 5.6 | 14.2 | 5000 | 35.2 | 132.0 | 0.33 | 0.62 |
| Ex.(I-19) | Com.(P-23) | 5.7 | 14.1 | 5000 | 35.4 | 129.9 | 0.33 | 0.61 |
| Ex.(I-20) | Com.(P-24) | 5.7 | 13.7 | 5000 | 36.4 | 132.5 | 0.33 | 0.61 |
| Ex.(I-21) | Com.(P-26) | 5.6 | 14.3 | 5000 | 35.0 | 131.7 | 0.33 | 0.62 |
| Ex.(I-22) | Com.(P-27) | 5.7 | 14.1 | 5000 | 35.6 | 130.3 | 0.33 | 0.62 |
| Ex.(I-23) | Com.(P-29) | 5.7 | 14.0 | 5000 | 35.7 | 129.1 | 0.33 | 0.62 |
| Ex.(I-24) | Com.(P-31) | 5.7 | 14.2 | 5000 | 35.2 | 130.9 | 0.33 | 0.61 |
| Ex.(I-25) | Com.(P-34) | 5.7 | 14.0 | 5000 | 35.8 | 130.3 | 0.33 | 0.61 |
| Ex.(I-26) | Com.(P-35) | 5.6 | 14.7 | 5000 | 34.1 | 125.1 | 0.33 | 0.62 |
| Ex.(I-27) | Com.(P-36) | 5.7 | 14.9 | 5000 | 33.5 | 127.1 | 0.33 | 0.61 |
| Ex.(I-28) | Com.(P-37) | 5.6 | 14.6 | 5000 | 34.2 | 127.4 | 0.33 | 0.62 |
| Ex.(I-29) | Com.(P-39) | 5.7 | 14.5 | 5000 | 34.5 | 132.3 | 0.33 | 0.62 |
| Ex.(I-30) | Com.(P-43) | 5.7 | 14.7 | 5000 | 34.1 | 127.6 | 0.33 | 0.62 |
| Ex.(I-31) | Com.(P-44) | 5.7 | 14.8 | 5000 | 33.7 | 128.5 | 0.33 | 0.62 |
| Ex.(I-32) | Com.(P-46) | 5.7 | 15.0 | 5000 | 33.4 | 126.5 | 0.33 | 0.62 |
| Ex.(I-33) | Com.(P-47) | 5.7 | 14.3 | 5000 | 34.9 | 128.8 | 0.33 | 0.62 |
| Ex.(I-34) | Com.(P-48) | 5.7 | 15.2 | 5000 | 32.8 | 125.3 | 0.33 | 0.62 |

From the results of the above table 4, it is found that luminous efficiency and lifetime of OLED are improved when the compound of the present invention is used as material of a hole transport layer.

Comparative Example I-3 to Comparative Example I-8, wherein Comparative compounds 3 to 8 having tertiary amine substituted with dibenzofuran are used as a hole transport layer material, exhibited higher luminous efficiency than Comparative Example I-1, wherein NPB, which is generally widely used, is used as a hole transport layer material, and Comparative Example I-2, wherein Comparative compound 2 having tertiary amine substituted with aryl groups are used as a hole transport layer material. Further, Example I-1 to Example I-34 of the present invention, wherein the compound of the present invention having tertiary amine substituted with dibenzofuran which is fused with aromatic ring is used as a hole transport layer material, exhibited lower driving voltage, higher luminous efficiency and improved lifetime than Comparative Example I-3 to Comparative Example I-8.

These results are considered to be due to the fact that the compound of the present invention has more substituents that increase the planarity of the molecules than Comparative Compounds 1 to 8.

The introduction of a substituent which enhances the planarity of the molecule is intended to increase the π-π orbital overlap between the molecules by increasing the intermolecular π-π stacking, so that the lone pair electron of the π orbital facilitates intermolecular transport, thereby improving the hole transporting ability.

Therefore, as the hole transfer ability becomes better, the deterioration of the interface between ITO and HTL is reduced, as a result, the lifetime of the device is improved, and the charge balance between the holes and the electrons in the light emitting layer is well-balanced because the hole can be easily transported to the light emitting layer, and thus the luminous efficiency and lifetime are improved.

These results can also be confirmed by comparing comparative compounds 3 to 8. It can be confirmed that although substituent that lower the planarity of the molecule is introduced into the comparative compounds 7 and 8 and the tertiary amine thereof is equally substituted with the dibenzofurane, the luminous efficiency of the comparative compounds 7 and 8 is further reduced than that of comparative compounds 3 to 6 due to a reduction in the charge balance in the light emitting layer.

The compound of the present invention having dibenzofuran which is bonded to the tertiary amine and to which an aromatic ring is fused has the increased planarity of the molecule and the packing density, as a result, the driving voltage of the device is lowered and the Joule heat generated when the device is driven is reduced, so that the device has high thermal stability. Therefore, it can be confirmed that the life span of the present invention is remarkably increased as compared to the comparative compounds 3 to 8.

Taking all the above described properties (high hole-transporting ability and thermal stability), it can be seen that electrical properties and interface characteristics can be greatly changed depending on whether or not a substituent which increases the planarity of the molecule is introduced and this acts as a major factor in improving the performance of the device.

In addition, even though similar core is used, it will be very difficult for those skilled in the art to infer the properties showing in a transport layer formed by the inventive compound because it is necessary to grasp interrelation between hole transport layer and a light emitting layer (host).

[Example II-1] Green OLED (an Emission-Auxiliary Layer

Organic light emitting diodes (OLEDs) were fabricated according to a conventional method by using a compound of the present invention as an emission-auxiliary layer material.

First, an ITO layer (anode) was formed on a glass substrate, and a film of 2-TNATA was vacuum-deposited on the ITO layer to form a hole injection layer with a thickness of 60 nm. Subsequently, Comparative compound 1 was vacuum-deposited with a thickness of 60 nm on the hole injection layer to form a hole transport layer.

Subsequently, a film of the compound P-1 of the present invention was vacuum-deposited on the hole transport layer to form a emission-auxiliary layer with a thickness of 20 nm. A light emitting layer with a thickness of 30 nm was deposited on the emission-auxiliary layer by using the CBP as a host material and Ir(ppy)$_3$ as a dopant material in a weight ratio of 90:10.

Next, a film of BAlq was vacuum-deposited with a thickness of 10 nm on the light emitting layer to form a hole blocking layer, and a film of Alq$_3$ was formed with a thickness of 40 nm to form an electron transport layer.

Next, LiF as halogenated alkali metal was deposited with a thickness of 0.2 nm on the electron transport layer to form an electron injection layer, and then Al was deposited with a thickness of 150 nm on the electron injection layer to form a cathode. In this way, the OLED was completed.

[Example II-2] to [Example II-28] Green OLED (an Emission-Auxiliary Layer

The OLEDs were fabricated in the same manner as described in Example II-1 except that the compounds P-3 to P-48 of the present invention described in Table 5, instead of the compound P-1 of the present invention, were used as an emission-auxiliary layer material.

Comparative Example II-1

The OLED was fabricated in the same manner as described in Example II-1 except that an emission-auxiliary layer was not formed.

[Comparative Example II-2] to [Comparative Example II-7]

The OLEDs were fabricated in the same manner as described in Example II-1 except that the Comparative compounds 3 to 8, instead of the compound P-1 of the present invention, were used as an emission-auxiliary layer material.

Example II-291

The OLEDs were fabricated in the same manner as described in Example II-1 except that the following Comparative compound 9 instead of the Comparative compound 1 were used as a hole transport layer material.

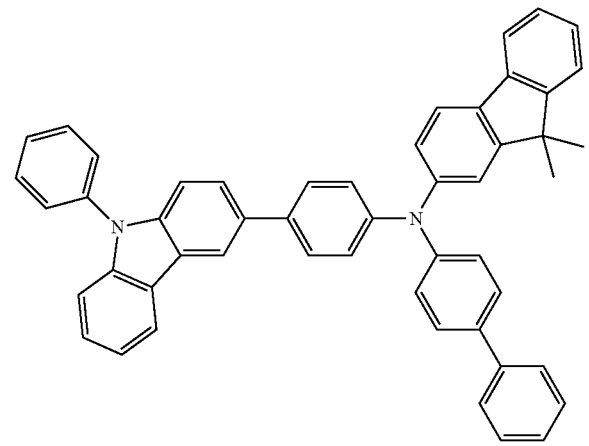

<Comp.compd 9>

[Example II-30] to [Example II-46] Green OLED (an Emission-Auxiliary Layer

The OLEDs were fabricated in the same manner as described in Example II-29 except that the compounds P-3 to P-48 of the present invention described in Table 6, instead of the compound P-1 of the present invention, were used as an emission-auxiliary layer material.

Comparative Example II-8

The OLED was fabricated in the same manner as described in Example II-29 except that an emission-auxiliary layer was not formed.

[Comparative Example II-9] to [Comparative Example II-14]

The OLEDs were fabricated in the same manner as described in Example II-29 except that the Comparative compounds 3 to 8, instead of the compound P-1 of the present invention, were used as an emission-auxiliary layer material.

Electroluminescence (EL) characteristics were measured with a PR-650 (Photoresearch) by applying a forward bias DC voltage to the OLEDs prepared in Examples II-1 to II-46 of the present invention and Comparative Examples II-1 to II-14. And, the T95 life time was measured using a life time measuring apparatus manufactured by Macscience Inc. at reference brightness of 5000 cd/m$^2$. The measurement results are shown in Tables 5 and 6 below.

TABLE 5

| | HTL com. | EAL com. | Voltage (V) | Current Density (mA/cm$^2$) | Brightness (cd/m$^2$) | Efficiency (cd/A) | Lifetime T(95) |
|---|---|---|---|---|---|---|---|
| comp. Ex(II-1) | comp. Com 1 | — | 6.0 | 21.5 | 5000 | 23.3 | 57.2 |
| comp. Ex(II-2) | comp. Com 1 | comp. Com3 | 6.4 | 13.7 | 5000 | 36.5 | 105.9 |
| comp. Ex(II-3) | comp. Com 1 | comp. Com4 | 6.4 | 13.7 | 5000 | 36.6 | 101.4 |
| comp. Ex(II-4) | comp. Com 1 | comp. Com5 | 6.3 | 12.5 | 5000 | 40.0 | 116.8 |
| comp. Ex(II-5) | comp. Com 1 | comp. Com6 | 6.3 | 12.6 | 5000 | 39.8 | 116.5 |
| comp. Ex(II-6) | comp. Com 1 | comp. Com7 | 6.4 | 14.3 | 5000 | 35.0 | 96.5 |
| comp. Ex(II-7) | comp. Com 1 | comp. Com8 | 6.4 | 14.2 | 5000 | 35.2 | 96.3 |
| Ex.(II-1) | comp. Com 1 | Com.(P-1) | 6.2 | 11.0 | 5000 | 45.4 | 155.8 |
| Ex.(II-2) | comp. Com 1 | Com.(P-3) | 6.1 | 10.8 | 5000 | 46.1 | 155.6 |

TABLE 5-continued

|  | HTL com. | EAL com. | Voltage (V) | Current Density (mA/cm$^2$) | Brightness (cd/m$^2$) | Efficiency (cd/A) | Lifetime T(95) |
|---|---|---|---|---|---|---|---|
| Ex.(II-3) | comp. Com 1 | Com.(P-4) | 6.1 | 11.0 | 5000 | 44.7 | 153.4 |
| Ex.(II-4) | comp. Com 1 | Com.(P-5) | 6.1 | 10.5 | 5000 | 47.4 | 160.1 |
| Ex.(II-5) | comp. Com 1 | Com.(P-6) | 6.1 | 11.0 | 5000 | 45.6 | 157.4 |
| Ex.(II-6) | comp. Com 1 | Com.(P-7) | 6.2 | 10.9 | 5000 | 45.7 | 154.0 |
| Ex.(II-7) | comp. Com 1 | Com.(P-9) | 6.2 | 11.3 | 5000 | 44.2 | 149.8 |
| Ex.(II-8) | comp. Com 1 | Com.(P-10) | 6.2 | 11.4 | 5000 | 44.0 | 146.7 |
| Ex.(II-9) | comp. Com 1 | Com.(P-11) | 6.2 | 11.3 | 5000 | 44.3 | 151.2 |
| Ex.(II-10) | comp. Com 1 | Com.(P-15) | 6.1 | 11.2 | 5000 | 44.5 | 151.0 |
| Ex.(II-11) | comp. Com 1 | Com.(P-16) | 6.2 | 11.5 | 5000 | 43.6 | 148.3 |
| Ex.(II-12) | comp. Com 1 | Com.(P-18) | 6.2 | 11.0 | 5000 | 45.4 | 153.7 |
| Ex.(II-13) | comp. Com 1 | Com.(P-19) | 6.3 | 11.3 | 5000 | 44.1 | 147.5 |
| Ex.(II-14) | comp. Com 1 | Com.(P-20) | 6.3 | 11.5 | 5000 | 43.5 | 149.1 |
| Ex.(II-15) | comp. Com 1 | Com.(P-22) | 6.2 | 11.5 | 5000 | 43.3 | 148.5 |
| Ex.(II-16) | comp. Com 1 | Com.(P-23) | 6.2 | 11.6 | 5000 | 43.1 | 150.3 |
| Ex.(II-17) | comp. Com 1 | Com.(P-24) | 6.3 | 11.4 | 5000 | 44.0 | 151.3 |
| Ex.(II-18) | comp. Com 1 | Com.(P-27) | 6.3 | 11.6 | 5000 | 43.2 | 152.6 |
| Ex.(II-19) | comp. Com 1 | Com.(P-29) | 6.2 | 11.5 | 5000 | 43.4 | 148.2 |
| Ex.(II-20) | comp. Com 1 | Com.(P-34) | 6.2 | 11.3 | 5000 | 44.2 | 149.4 |
| Ex.(II-21) | comp. Com 1 | Com.(P-36) | 6.3 | 11.8 | 5000 | 42.5 | 142.2 |
| Ex.(II-22) | comp. Com 1 | Com.(P-39) | 6.2 | 11.7 | 5000 | 42.8 | 152.5 |
| Ex.(II-23) | comp. Com 1 | Com.(P-40) | 6.3 | 11.8 | 5000 | 42.5 | 143.5 |
| Ex.(II-24) | comp. Com 1 | Com.(P-41) | 6.3 | 11.7 | 5000 | 42.7 | 142.6 |
| Ex.(II-25) | comp. Com 1 | Com.(P-43) | 6.3 | 11.8 | 5000 | 42.3 | 143.1 |
| Ex.(II-26) | comp. Com 1 | Com.(P-44) | 6.3 | 11.9 | 5000 | 42.0 | 144.0 |
| Ex.(II-27) | comp. Com 1 | Com.(P-47) | 6.3 | 11.6 | 5000 | 43.0 | 152.4 |
| Ex.(II-28) | comp. Com 1 | Com.(P-48) | 6.3 | 11.8 | 5000 | 42.3 | 146.1 |

TABLE 6

|  | HTL com. | EAL com. | Voltage (V) | Current Density (mA/cm$^2$) | Brightness (cd/m$^2$) | Efficiency (cd/A) | Lifetime T(95) |
|---|---|---|---|---|---|---|---|
| comp. Ex(II-8) | comp. Com 9 | — | 5.0 | 14.3 | 5000 | 35.0 | 97.3 |
| comp. Ex(II-9) | comp. Com 9 | comp. Com3 | 5.4 | 13.0 | 5000 | 38.5 | 119.7 |
| comp. Ex(II-10) | comp. Com 9 | comp. Com4 | 5.3 | 12.9 | 5000 | 38.6 | 120.1 |
| comp. Ex(II-11) | comp. Com 9 | comp. Com5 | 5.3 | 11.9 | 5000 | 42.0 | 129.3 |
| comp. Ex(II-12) | comp. Com 9 | comp. Com6 | 5.3 | 12.0 | 5000 | 41.7 | 131.4 |
| comp. Ex(II-13) | comp. Com 9 | comp. Com7 | 5.4 | 13.5 | 5000 | 37.0 | 115.5 |
| comp. Ex(II-14) | comp. Com 9 | comp. Com8 | 5.4 | 13.5 | 5000 | 37.1 | 115.2 |
| Ex.(II-29) | comp. Com 9 | Com.(P-1) | 5.2 | 10.3 | 5000 | 48.7 | 169.6 |
| Ex.(II-30) | comp. Com 9 | Com.(P-3) | 5.1 | 10.1 | 5000 | 49.4 | 170.9 |
| Ex.(II-31) | comp. Com 9 | Com.(P-4) | 5.1 | 10.4 | 5000 | 48.2 | 168.1 |
| Ex.(II-32) | comp. Com 9 | Com.(P-5) | 5.1 | 9.9 | 5000 | 50.4 | 175.5 |
| Ex.(II-33) | comp. Com 9 | Com.(P-6) | 5.1 | 10.3 | 5000 | 48.5 | 171.5 |
| Ex.(II-34) | comp. Com 9 | Com.(P-7) | 5.1 | 10.4 | 5000 | 48.1 | 164.2 |
| Ex.(II-35) | comp. Com 9 | Com.(P-11) | 5.2 | 10.7 | 5000 | 46.8 | 167.8 |
| Ex.(II-36) | comp. Com 9 | Com.(P-15) | 5.1 | 10.4 | 5000 | 48.0 | 167.8 |
| Ex.(II-37) | comp. Com 9 | Com.(P-18) | 5.2 | 10.3 | 5000 | 48.5 | 167.0 |
| Ex.(II-38) | comp. Com 9 | Com.(P-19) | 5.2 | 10.7 | 5000 | 46.8 | 164.1 |
| Ex.(II-39) | comp. Com 9 | Com.(P-20) | 5.2 | 10.7 | 5000 | 46.9 | 162.1 |
| Ex.(II-40) | comp. Com 9 | Com.(P-24) | 5.3 | 10.7 | 5000 | 46.7 | 166.0 |
| Ex.(II-41) | comp. Com 9 | Com.(P-27) | 5.2 | 10.8 | 5000 | 46.4 | 167.2 |
| Ex.(II-42) | comp. Com 9 | Com.(P-34) | 5.2 | 10.7 | 5000 | 46.7 | 162.6 |
| Ex.(II-43) | comp. Com 9 | Com.(P-39) | 5.3 | 10.7 | 5000 | 46.6 | 166.4 |
| Ex.(II-44) | comp. Com 9 | Com.(P-44) | 5.2 | 10.8 | 5000 | 46.5 | 163.1 |
| Ex.(II-45) | comp. Com 9 | Com.(P-47) | 5.2 | 10.8 | 5000 | 46.4 | 166.6 |
| Ex.(II-46) | comp. Com 9 | Com.(P-48) | 5.3 | 10.8 | 5000 | 46.5 | 162.1 |

[Test Example III-1] Blue Organic Light Emitting Diode (Emission-Auxiliary Layer Organic light emitting diodes (OLEDs) were fabricated according to a conventional method by using a compound of the present invention as an emission-auxiliary layer material. First, an ITO layer (anode) was formed on a glass substrate, and 2-TNATA was vacuum-deposited on the ITO layer to form a hole injection layer with a thickness of 60 nm. Subsequently, the Comparative compound 9 was vacuum-deposited with a thickness of 60 nm on the hole injection layer to form a hole transport layer. Next, the inventive compound P-1 was vacuum-deposited with a thickness of 20 nm on the hole transport layer to form an emission-auxiliary layer. Thereafter, a light emitting layer with a thickness of 30 nm was deposited on the emission-auxiliary layer by doping the emission-auxiliary layer with 9, 10-di(naphthalen-2-yl)anthracene (hereinafter abbreviated as "ADN") as a host material and BD-052X (made by Idemitsu kosan) as a dopant material in a weight ratio of 96:4. Also, BAlq was vacuum-deposited with a thickness of 10 nm on the light emitting layer to form a hole blocking layer, and then a film of $Alq_3$ was formed with a thickness of 40 nm to form an electron injection layer. Subsequently, LiF as halogenated alkali metal was deposited with a thickness of 0.2 nm on the electron injection layer, and then Al was deposited with a thickness of 150 nm thereon to form a cathode. In this way, an OLED was completed.

[Example III-2] to [Example III-12] Green OLED (an Emission-Auxiliary Layer

The OLEDs were fabricated in the same manner as described in Example III-1 except that the compounds P-3 to P-34 of the present invention described in Table 7, instead of the compound P-1 of the present invention, were used as an emission-auxiliary layer material.

Comparative Example III-1

The OLED was fabricated in the same manner as described in Example III-1 except that an emission-auxiliary layer was not formed.

[Comparative Example IIII-2] to [Comparative Example III-7]

The OLEDs were fabricated in the same manner as described in Example III-1 except that the Comparative compounds 3 to 8, instead of the compound P-1 of the present invention, were used as an emission-auxiliary layer material.

Electroluminescence (EL) characteristics were measured with a PR-650 (Photoresearch) by applying a forward bias DC voltage to the OLEDs prepared in Examples III-1 to III-12 of the present invention and Comparative Examples III-1 to III-7. And, the T95 life time was measured using a life time measuring apparatus manufactured by Macscience Inc. at reference brightness of 500 $cd/m^2$. The measurement results are shown in Table 7 below.

auxiliary layer material, compared with the organic electroluminescent device of Comparative Example II-1 to Comparative Example III-7.

From these results, it is confirmed that luminescent efficiency and lifetime of device are improved when Comparative Compounds 3 to 8 and the compound of the present invention are used as an emission-auxiliary layer material, among them, particularly the compound of the present invention, compared with device not having an emission-auxiliary layer.

It is confirmed that the structure (introduction of substituents increasing a planarity of molecule) in which the aromatic ring-condensed dibenzofurane is bonded to the tertiary amine acts as a major factor in improving the performance of the device in the light-emitting auxiliary layer (green phosphorescence, blue fluorescence) as well as in the hole transport layer. Also, it is confirmed that the compound of the present invention used as the light emitting auxiliary layer material has a deep HOMO energy level and a high T1 value, thereby maintaining the charge balance in the light emitting layer and performing an effective electronic blocking function, as a result, the light emitting efficiency and lifetime are improved.

In addition, in the evaluation results of the device fabrication described above, even though the characteristics of devise have been described when the compound of the present invention is used as material of only one layer of the hole transport layer and an emission-auxiliary layer, the compound of the present invention can be used as material of both the hole transport layer and an emission-auxiliary layer.

Although exemplary embodiments of the present invention have been described for illustrative purposes, those skilled in the art will appreciate that various modifications, additions and substitutions are possible, without departing from the scope and spirit of the invention as disclosed in the accompanying claims. Therefore, the embodiment disclosed in the present invention is intended to illustrate the scope of

TABLE 7

| | HTL com. | EAL com. | Voltage (V) | Current Density ($mA/cm^2$) | Brightness ($cd/m^2$) | Efficiency (cd/A) | Lifetime T(95) |
| --- | --- | --- | --- | --- | --- | --- | --- |
| comp. Ex(III-1) | comp. Com 9 | — | 4.2 | 12.2 | 500 | 4.1 | 95.8 |
| comp. Ex(III-2) | comp. Com 9 | comp. Com3 | 4.5 | 7.7 | 500 | 6.5 | 111.9 |
| comp. Ex(III-3) | comp. Com 9 | comp. Com4 | 4.4 | 7.6 | 500 | 6.6 | 109.1 |
| comp. Ex(III-4) | comp. Com 9 | comp. Com5 | 4.4 | 7.4 | 500 | 6.8 | 118.4 |
| comp. Ex(III-5) | comp. Com 9 | comp. Com6 | 4.3 | 7.2 | 500 | 6.9 | 120.7 |
| comp. Ex(III-6) | comp. Com 9 | comp. Com7 | 4.6 | 8.3 | 500 | 6.0 | 98.4 |
| comp. Ex(III-7) | comp. Com 9 | comp. Com8 | 4.6 | 8.1 | 500 | 6.2 | 103.2 |
| Ex.(III-1) | comp. Com 9 | Com.(P-1) | 4.3 | 6.7 | 500 | 7.5 | 166.5 |
| Ex.(III-2) | comp. Com 9 | Com.(P-3) | 4.3 | 6.6 | 500 | 7.6 | 170.7 |
| Ex.(III-3) | comp. Com 9 | Com.(P-4) | 4.3 | 6.7 | 500 | 7.4 | 162.7 |
| Ex.(III-4) | comp. Com 9 | Com.(P-5) | 4.3 | 6.6 | 500 | 7.6 | 175.7 |
| Ex.(III-5) | comp. Com 9 | Com.(P-6) | 4.3 | 6.7 | 500 | 7.5 | 168.5 |
| Ex.(III-6) | comp. Com 9 | Com.(P-7) | 4.3 | 6.7 | 500 | 7.5 | 162.2 |
| Ex.(III-7) | comp. Com 9 | Com.(P-11) | 4.3 | 6.8 | 500 | 7.4 | 155.6 |
| Ex.(III-8) | comp. Com 9 | Com.(P-15) | 4.4 | 6.7 | 500 | 7.4 | 159.8 |
| Ex.(III-9) | comp. Com 9 | Com.(P-18) | 4.3 | 6.7 | 500 | 7.5 | 164.3 |
| Ex.(III-10) | comp. Com 9 | Com.(P-19) | 4.4 | 6.8 | 500 | 7.4 | 159.3 |
| Ex.(III-11) | comp. Com 9 | Com.(P-20) | 4.4 | 6.8 | 500 | 7.4 | 154.8 |
| Ex.(III-12) | comp. Com 9 | Com.(P-34) | 4.4 | 6.8 | 500 | 7.3 | 155.3 |

From the results shown in Tables 5 to 7, it can be seen that the luminous efficiency and lifetime of the organic electroluminescent device are remarkably improved when compounds of the present invention were used as an emissionthe technical idea of the present invention, and the scope of the present invention is not limited by the embodiment. The scope of the present invention shall be construed on the basis of the accompanying claims, and it shall be construed that all

The invention claimed is:

1. A compound of Formula 3:

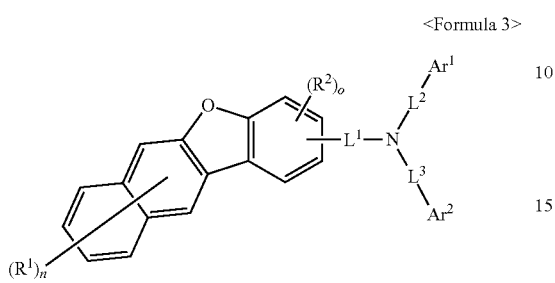

<Formula 3> wherein:
$R^1$ and $R^2$ are each independently selected from the group consisting of deuterium, a cyano group, a $C_6$-$C_{60}$ aryl group, a fluorenyl group, a $C_2$-$C_{60}$ heterocyclic group containing at least one heteroatom selected from the group consisting of O, N, S, Si, and P, a fused ring group of a $C_3$-$C_{60}$ aliphatic ring and a $C_6$-$C_{60}$ aromatic ring, a $C_1$-$C_{50}$ alkyl group, a $C_2$-$C_{20}$ alkenyl group, a $C_2$-$C_{20}$ alkynyl group, a $C_1$-$C_{30}$ alkoxyl group, and a $C_6$-$C_{30}$ aryloxyl group, n is an integer of 0 to 6 and o is an integer of 0 to 3, and a plurality of $R^1$ and $R^2$ are each the same or different from each other when n and o are each an integer of 2 or more, $L^1$ is a 1,4-phenylene group, $L^2$ and $L^3$ are each independently a single bond or a $C_6$-$C_{60}$ arylene group, $Ar^1$ and $Ar^2$ are each independently a $C_6$-$C_{60}$ aryl group, with the proviso that at least one of $Ar^1$ and $Ar^2$ is a naphthyl or phenanthrenyl group, when $R^1$ and $R^2$ are each the aryl group, fluorenyl group, heterocyclic group, fused ring group, alkyl group, alkenyl group, alkynyl group, alkoxyl group, or aryloxy group, each of the groups may be each optionally further substituted with one or more substituents selected from the group consisting of deuterium, halogen, a silane group substituted or unsubstituted with a $C_1$-$C_{20}$ alkyl group or a $C_6$-$C_{20}$ aryl group, a siloxane group, a boron group, a germanium group, a cyano group, a $C_1$-$C_{20}$ alkylthio group, a $C_1$-$C_{20}$ alkoxyl group, a $C_1$-$C_{20}$ alkyl group, a $C_2$-$C_{20}$ alkenyl group, a $C_2$-$C_{20}$ alkynyl group, a $C_6$-$C_{20}$ aryl group, a $C_6$-$C_{20}$ aryl group substituted with deuterium, a fluorenyl group, a $C_2$-$C_{20}$ heterocyclic group containing at least one heteroatom selected from the group consisting of O, N, S, Si, and P, a $C_3$-$C_{20}$ cycloalkyl group, a $C_7$-$C_{20}$ arylalkyl group, and a $C_8$-$C_{20}$ arylalkenyl group, the phenylene group of $L^1$ may be optionally substituted with one or more substituents selected from the group consisting of deuterium, halogen, a silane group substituted or unsubstituted with a $C_1$-$C_{20}$ alkyl group or a $C_6$-$C_{20}$ aryl group, a siloxane group, a boron group, a germanium group, a cyano group, a nitro group, a $C_1$-$C_{20}$ alkylthio group, a $C_1$-$C_{20}$ alkoxyl group, a $C_1$-$C_{20}$ alkyl group, a $C_2$-$C_{20}$ alkenyl group, a $C_2$-$C_{20}$ alkynyl group, a $C_6$-$C_{20}$ aryl group, a $C_6$-$C_{20}$ aryl group substituted with deuterium, a fluorenyl group, a $C_2$-$C_{20}$ heterocyclic group containing at least one heteroatom selected from the group consisting of O, N, S, Si, and P, a $C_3$-$C_{20}$ cycloalkyl group, a $C_7$-$C_{20}$ arylalkyl group, and a $C_8$-$C_{20}$ arylalkenyl group, the arylene group of $L^2$ and $L^3$ may be optionally further substituted with one or more substituents selected from the group consisting of deuterium, halogen, a silane group substituted or unsubstituted with a $C_1$-$C_{20}$ alkyl group or a $C_6$-$C_{20}$ aryl group, a siloxane group, a boron group, a germanium group, a cyano group, a nitro group, a $C_1$-$C_{20}$ alkylthio group, a $C_1$-$C_{20}$ alkoxyl group, a $C_1$-$C_{20}$ alkyl group, a $C_2$-$C_{20}$ alkenyl group, a $C_2$-$C_{20}$ alkynyl group, a $C_3$-$C_{20}$ cycloalkyl group, a $C_7$-$C_{20}$ arylalkyl group, and a $C_8$-$C_{20}$ arylalkenyl group, and the aryl group of $Ar^1$ and $Ar^2$ may be optionally further substituted with one or more substituents selected from the group consisting of deuterium, halogen, a silane group substituted or unsubstituted with a $C_1$-$C_{20}$ alkyl group or a $C_6$-$C_{20}$ aryl group, a siloxane group, a boron group, a germanium group, a cyano group, a nitro group, a $C_1$-$C_{20}$ alkylthio group, a $C_1$-$C_{20}$ alkoxyl group, a $C_1$-$C_{20}$ alkyl group, a $C_2$-$C_{20}$ alkenyl group, a $C_2$-$C_{20}$ alkynyl group, a $C_6$-$C_{20}$ aryl group substituted with deuterium, a fluorenyl group, a $C_3$-$C_{20}$ cycloalkyl group, a $C_7$-$C_{20}$ arylalkyl group, and a $C_8$-$C_{20}$ arylalkenyl group, and adjacent substituents in $Ar^1$ or adjacent substituents in $Ar^2$ may be linked to each other to form a ring, with the proviso that:
(i) a compound of formula 3 wherein $L^2$-$Ar^1$ or $L^3$-$Ar^2$ includes a terphenyl or a substituted or unsubstituted fluorenyl group, is excluded.

2. A compound represented by one of Formulas 4 to 9:

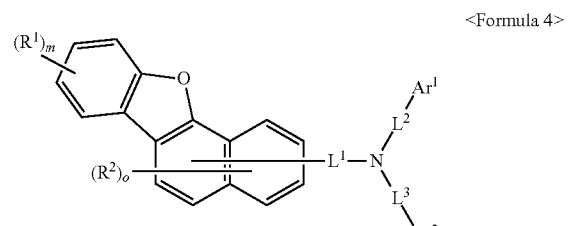

<Formula 4>

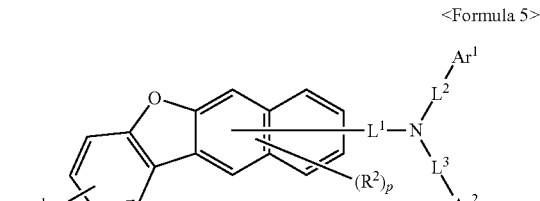

<Formula 5>

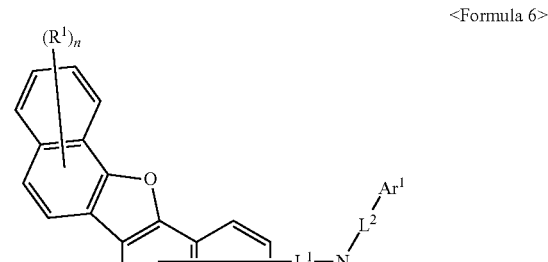

<Formula 6>

-continued

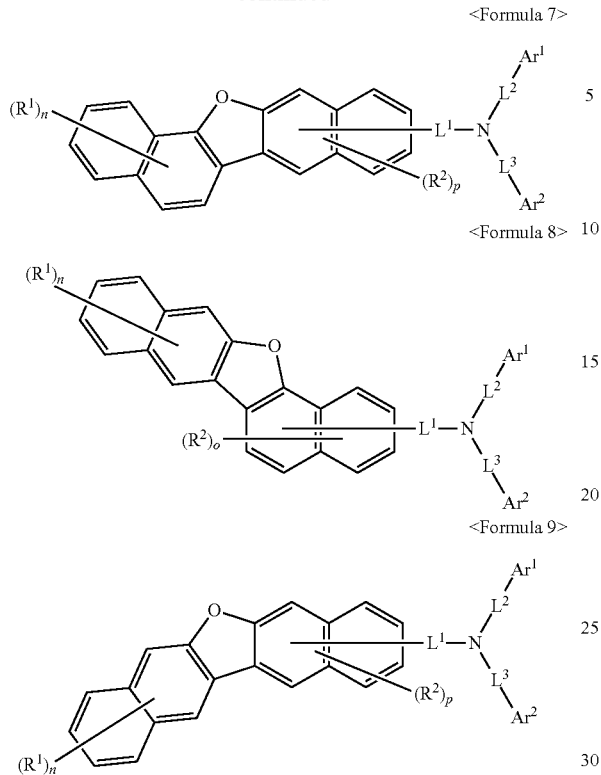

<Formula 7>

<Formula 8>

<Formula 9>

$R^1$ and $R^2$ are each independently selected from the group consisting of deuterium, a cyano group, a $C_6$-$C_{60}$ aryl group, a fluorenyl group, a $C_2$-$C_{60}$ heterocyclic group containing at least one heteroatom selected from the group consisting of O, N, S, Si, and P, a fused ring group of a $C_3$-$C_{60}$ aliphatic ring and a $C_6$-$C_{60}$ aromatic ring, a $C_1$-$C_{50}$ alkyl group, a $C_2$-$C_{20}$ alkenyl group, a $C_2$-$C_{20}$ alkynyl group, a $C_1$-$C_{30}$ alkoxyl group, and a $C_6$-$C_{30}$ aryloxyl group, $L^1$ is $C_6$-$C_{60}$ arylene group, $L^2$ and $L^3$ are each independently a single bond or a $C_6$-$C_{60}$ arylene group, $Ar^1$ and $Ar^2$ are each independently a $C_6$-$C_{60}$ aryl group, when $R^1$ and $R^2$ are each the aryl group, fluorenyl group, heterocyclic group, fused ring group, alkyl group, alkenyl group, alkynyl group, alkoxyl group, or aryloxy group, each of the groups may be optionally further substituted with one or more substituents selected from the group consisting of deuterium, halogen, a silane group substituted or unsubstituted with a $C_1$-$C_{20}$ alkyl group or a $C_6$-$C_{20}$ aryl group, a siloxane group, a boron group, a germanium group, a cyano group, a $C_1$-$C_{20}$ alkylthio group, a $C_1$-$C_{20}$ alkoxyl group, a $C_1$-$C_{20}$ alkyl group, a $C_2$-$C_{20}$ alkenyl group, a $C_2$-$C_{20}$ alkynyl group, a $C_6$-$C_{20}$ aryl group, a $C_6$-$C_{20}$ aryl group substituted with deuterium, a fluorenyl group, a $C_2$-$C_{20}$ heterocyclic group containing at least one heteroatom selected from the group consisting of O, N, S, Si, and P, a $C_3$-$C_{20}$ cycloalkyl group, a $C_7$-$C_{20}$ arylalkyl group, and a $C_8$-$C_{20}$ arylalkenyl group, the arylene group of $L^1$ may be optionally further substituted with one or more substituents selected from the group consisting of deuterium, halogen, a silane group substituted or unsubstituted with a $C_1$-$C_{20}$ alkyl group or a $C_6$-$C_{20}$ aryl group, a siloxane group, a boron group, a germanium group, a cyano group, a nitro group, a $C_1$-$C_{20}$ alkylthio group, a $C_1$-$C_{20}$ alkoxyl group, a $C_1$-$C_{20}$ alkyl group, a $C_2$-$C_{20}$ alkenyl group, a $C_2$-$C_{20}$ alkynyl group, a $C_6$-$C_{20}$ aryl group, a $C_6$-$C_{20}$ aryl group substituted with deuterium, a fluorenyl group, a $C_2$-$C_{20}$ heterocyclic group containing at least one heteroatom selected from the group consisting of O, N, S, Si, and P, a $C_3$-$C_{20}$ cycloalkyl group, a $C_7$-$C_{20}$ arylalkyl group, and a $C_8$-$C_{20}$ arylalkenyl group, the arylene group of $L^2$ and $L^3$ may be optionally further substituted with one or more substituents selected from the group consisting of deuterium, halogen, a silane group substituted or unsubstituted with a $C_1$-$C_{20}$ alkyl group or a $C_6$-$C_{20}$ aryl group, a siloxane group, a boron group, a germanium group, a cyano group, a nitro group, a $C_1$-$C_{20}$ alkylthio group, a $C_1$-$C_{20}$ alkoxyl group, a $C_1$-$C_{20}$ alkyl group, a $C_2$-$C_{20}$ alkenyl group, a $C_2$-$C_{20}$ alkynyl group, a $C_3$-$C_{20}$ cycloalkyl group, a $C_7$-$C_{20}$ arylalkyl group, and a $C_8$-$C_{20}$ arylalkenyl group, the aryl group of $Ar^1$ and $Ar^2$ may be optionally further substituted with one or more substituents selected from the group consisting of deuterium, halogen, a silane group substituted or unsubstituted with a $C_1$-$C_{20}$ alkyl group or a $C_6$-$C_{20}$ aryl group, a siloxane group, a boron group, a germanium group, a cyano group, a nitro group, a $C_1$-$C_{20}$ alkylthio group, a $C_1$-$C_{20}$ alkoxyl group, a $C_1$-$C_{20}$ alkyl group, a $C_2$-$C_{20}$ alkenyl group, a $C_2$-$C_{20}$ alkynyl group, a $C_6$-$C_{20}$ aryl group substituted with deuterium, a fluorenyl group, a $C_3$-$C_{20}$ cycloalkyl group, a $C_7$-$C_{20}$ arylalkyl group, and a $C_8$-$C_{20}$ arylalkenyl group, and adjacent substituents in $Ar^1$ or adjacent substituents in $Ar^2$ may be linked to each other to form a ring, and m is an integer of 0 to 4, n is an integer of 0 to 6, p is an integer of 0 to 5, and a plurality of $R^1$ and $R^2$ are each the same or different from each other when m, n and p are each an integer of 2 or more, with the proviso that a compound of the formulas wherein $L^2$-$Ar^1$ or $L^3$-$Ar^2$ includes a terphenyl or unsubstituted or substituted fluorenyl group, is excluded.

3. A compound selected from the group consisting of the compounds below:

P-1

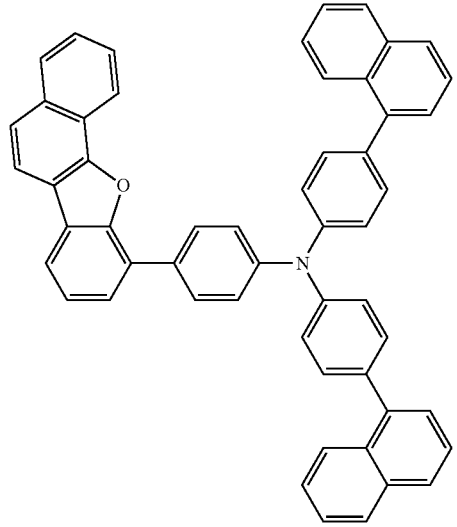

P-3
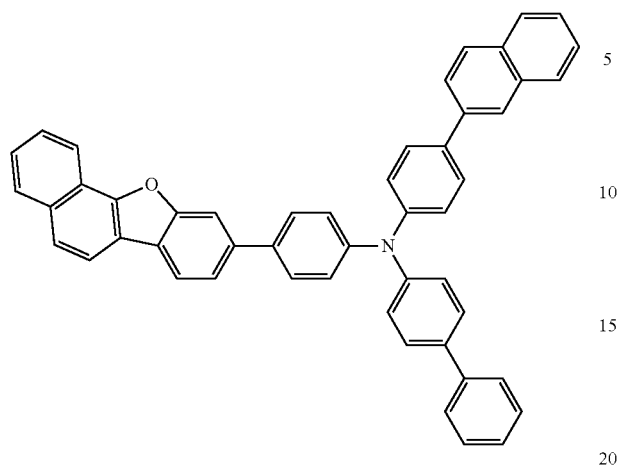
P-6
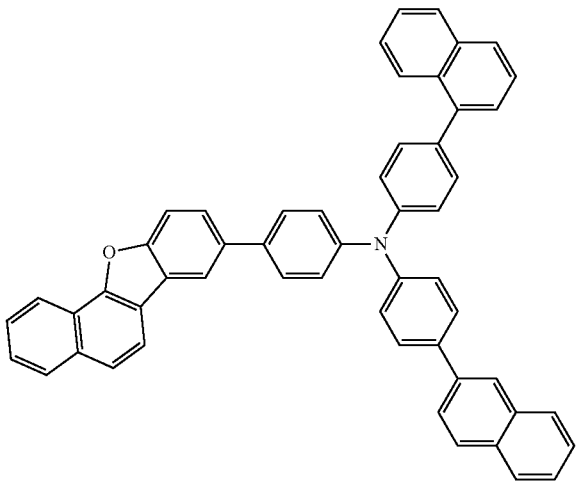
P-4
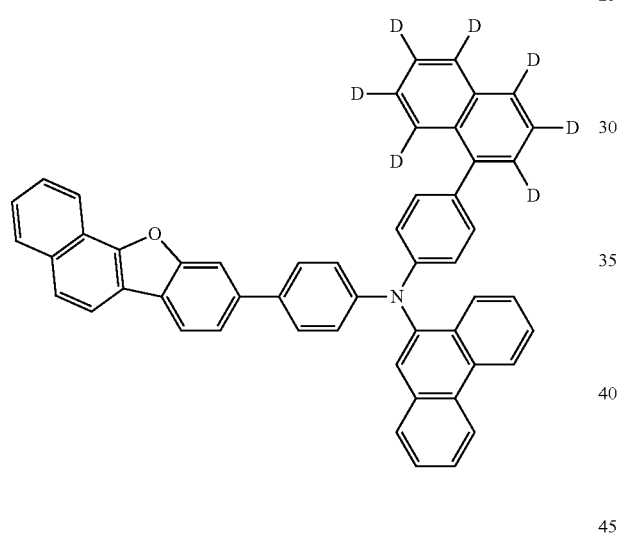
P-9
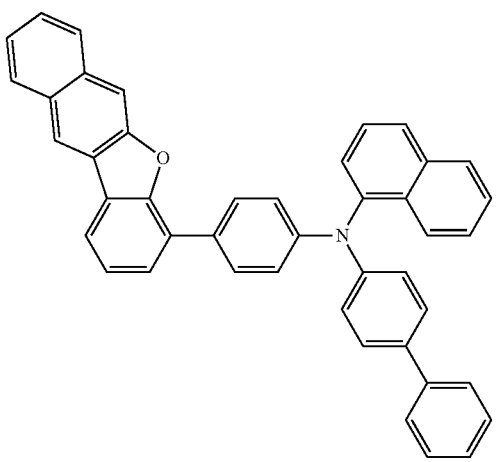
P-5
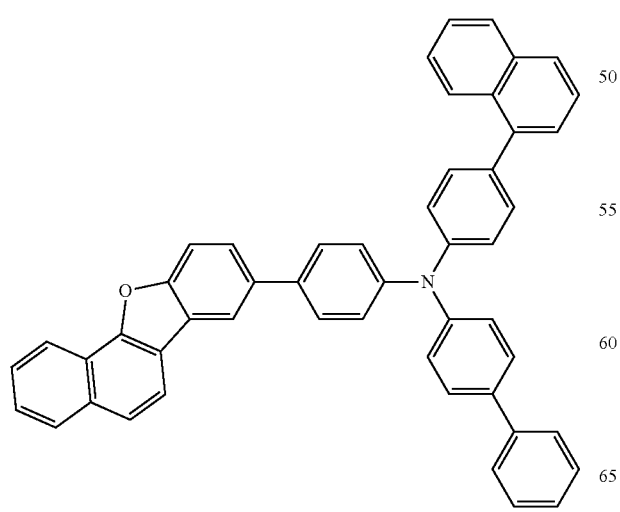
P-10
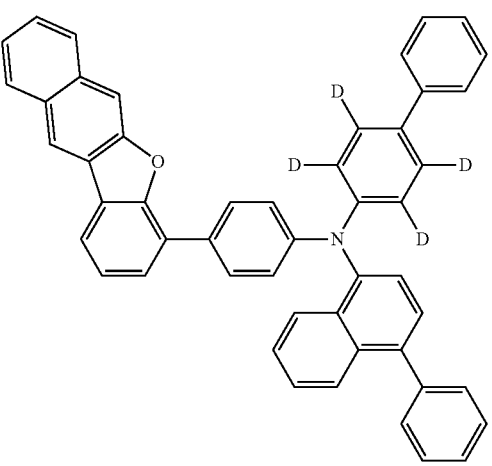

P-11
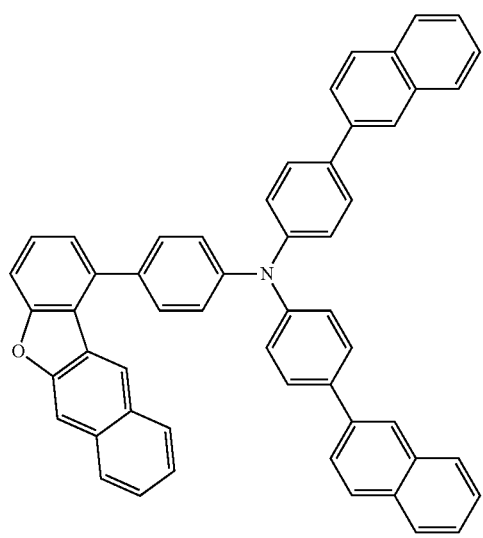
P-14
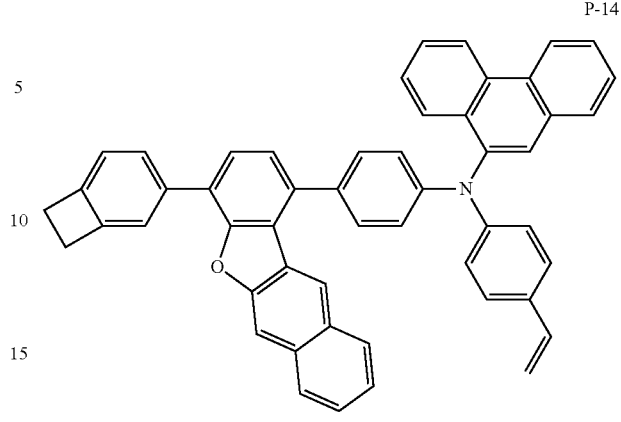
P-12
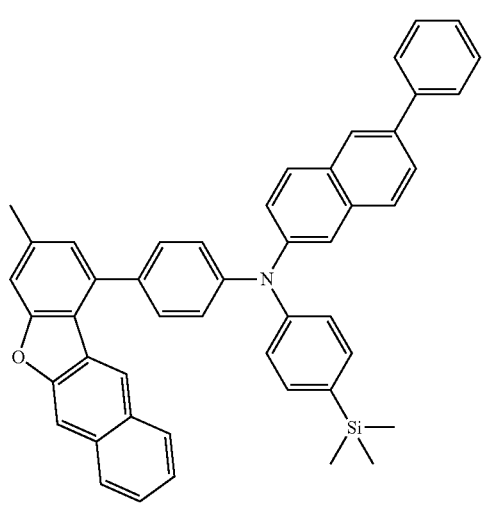
P-15
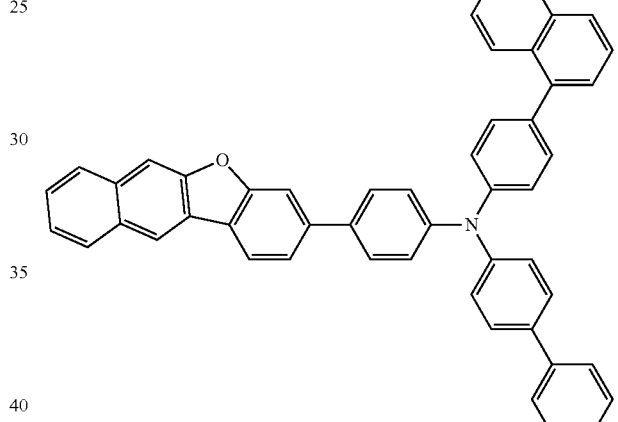
P-13
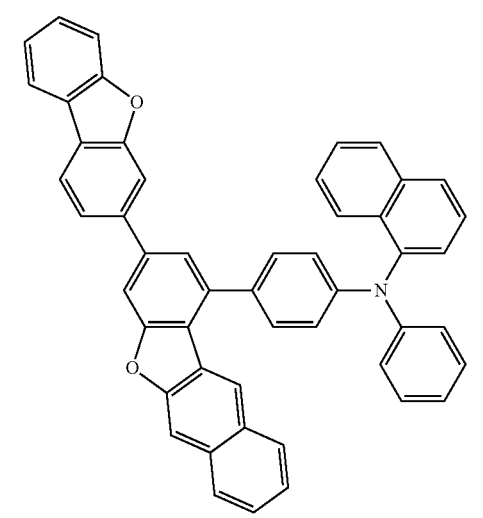
P-16
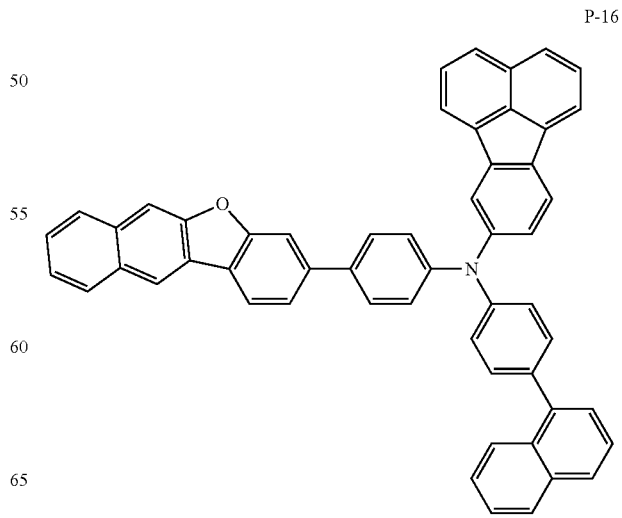

P-17
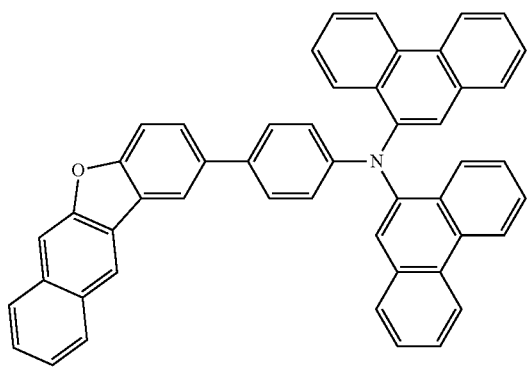
P-18
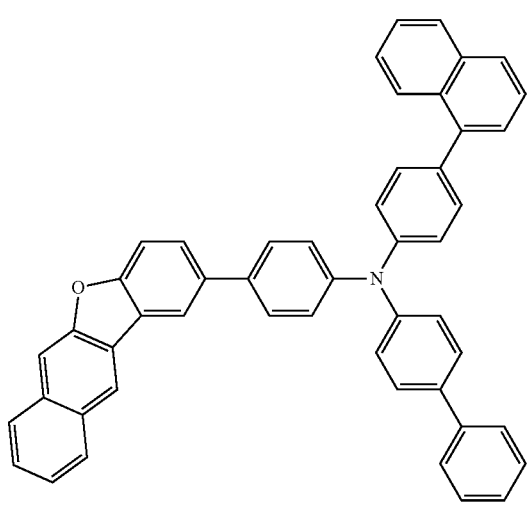
P-19
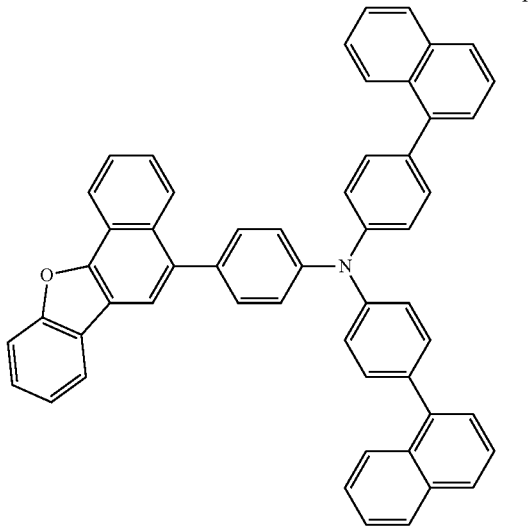
P-20
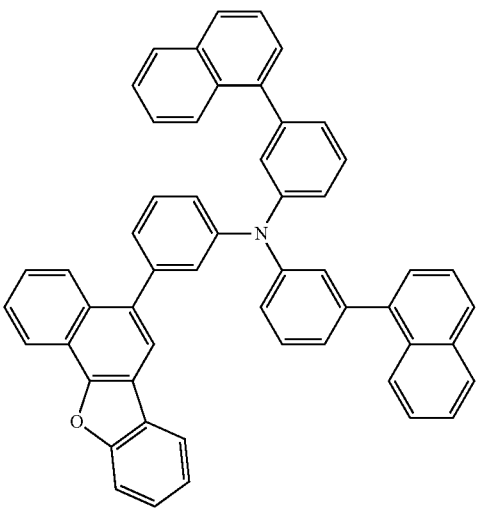
P-21
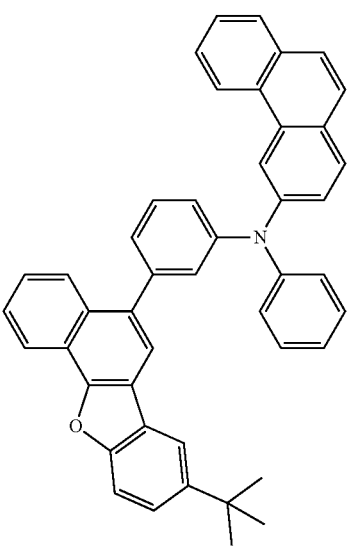
P-22
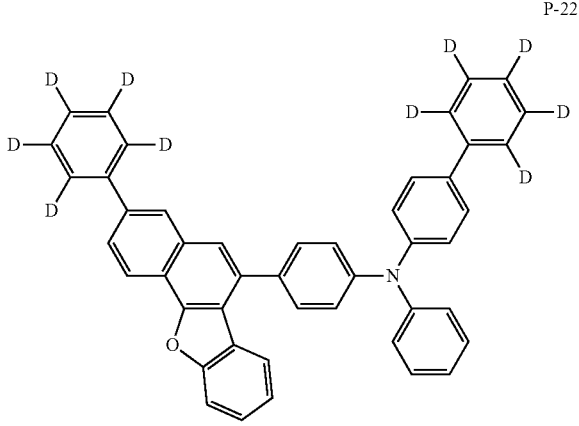

-continued
P-23
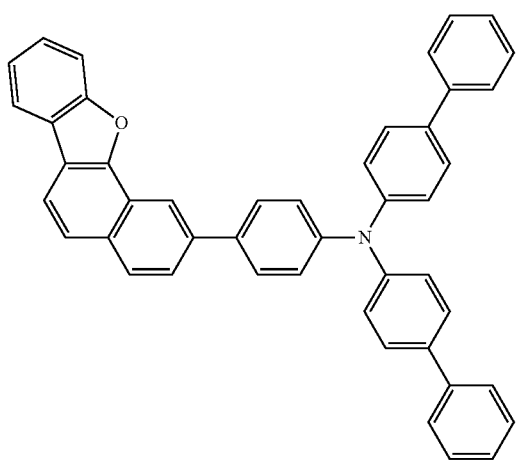
P-24
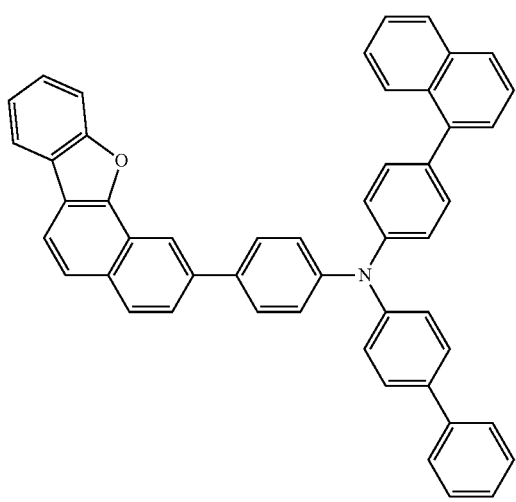
P-25
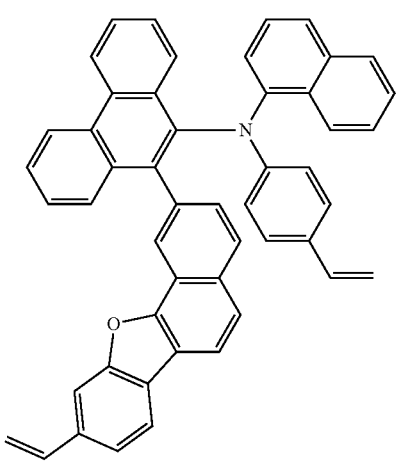
-continued
P-26
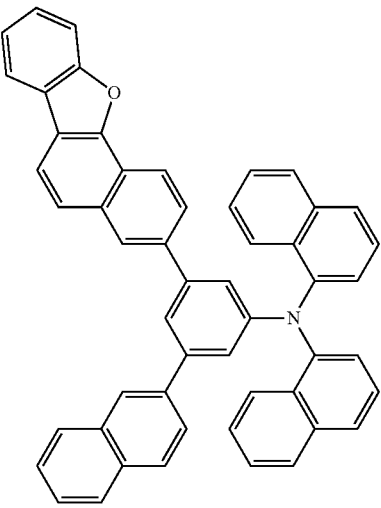
P-27
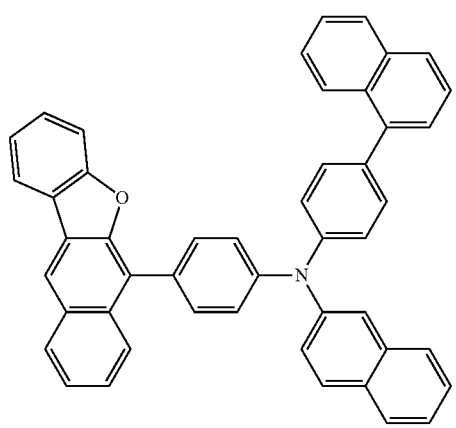
P-28
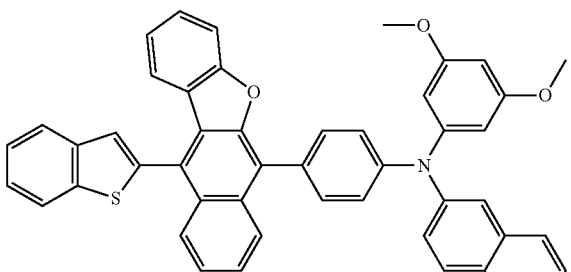
P-30
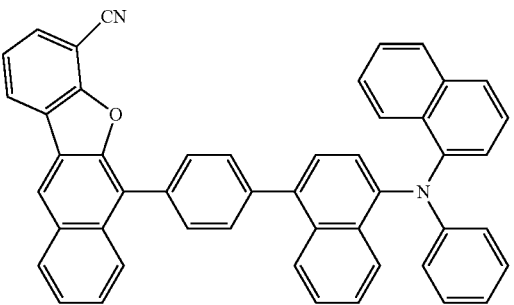

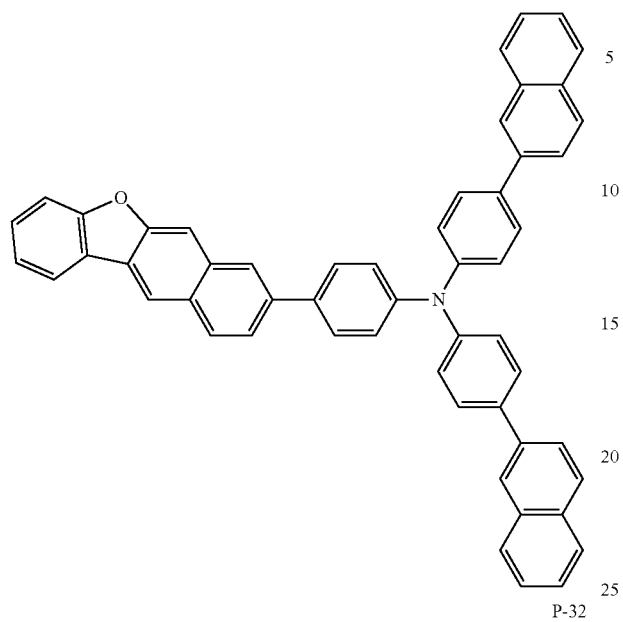
P-31
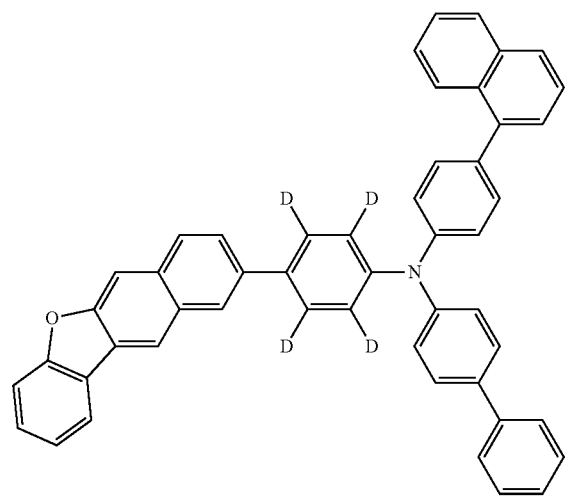
P-34
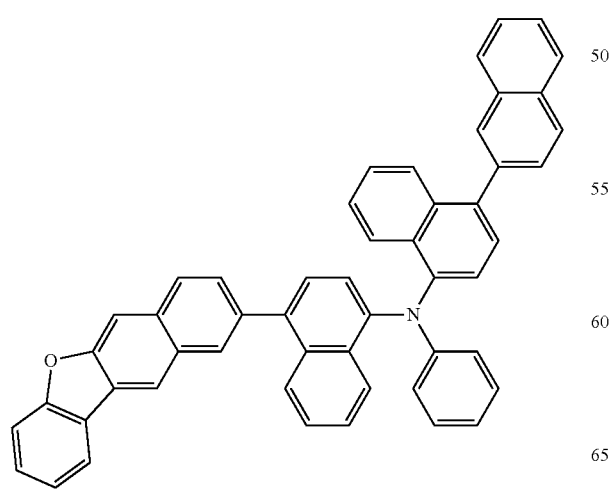
P-32
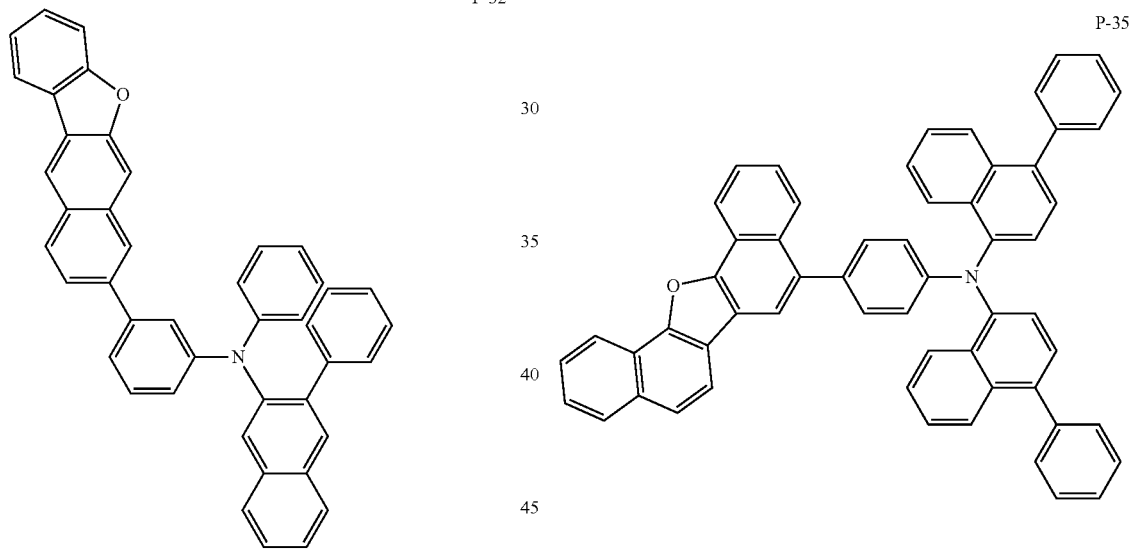
P-35
P-33
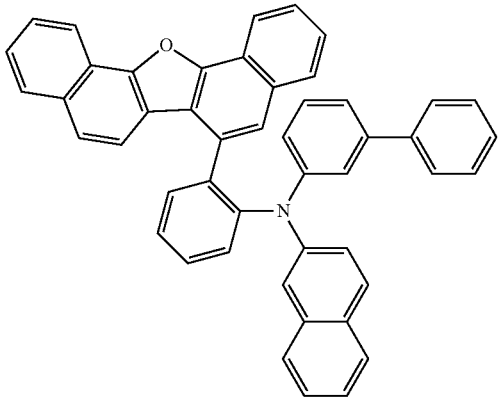
P-36

P-37
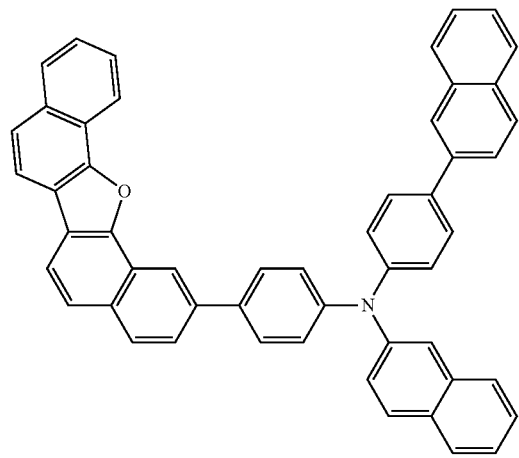
P-38
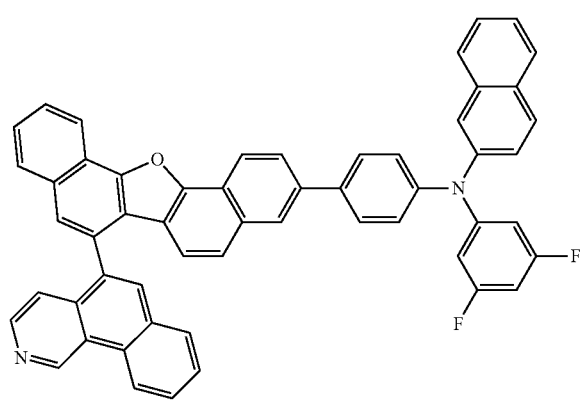
P-39
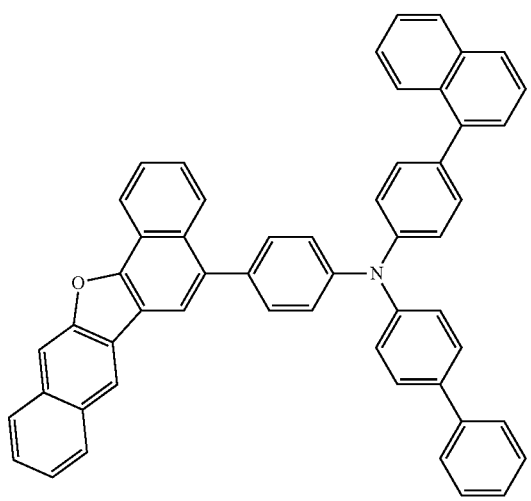
P-40
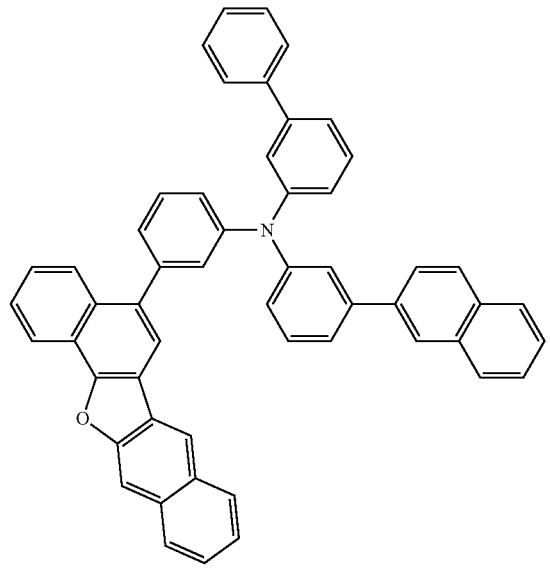
P-41
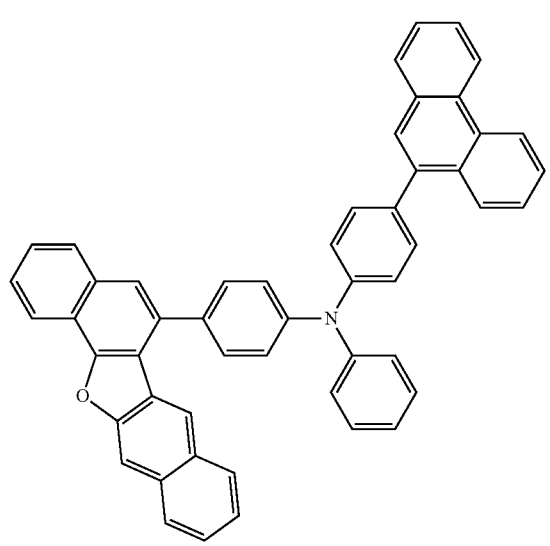
P-42
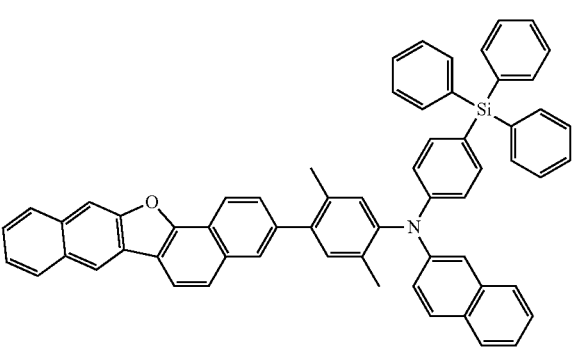

P-43
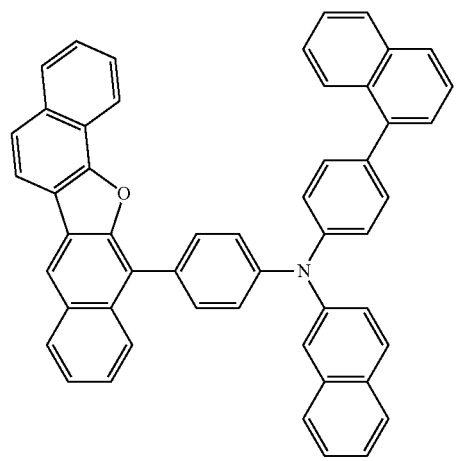
P-44
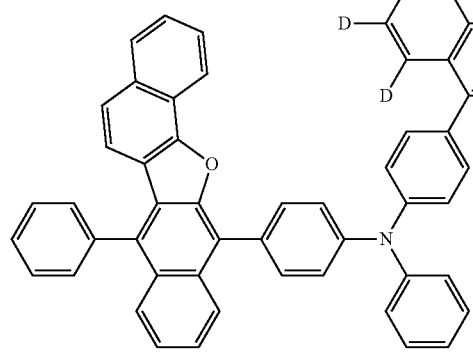
P-45
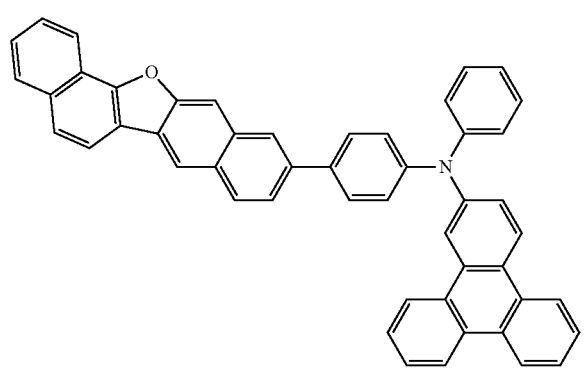
P-46
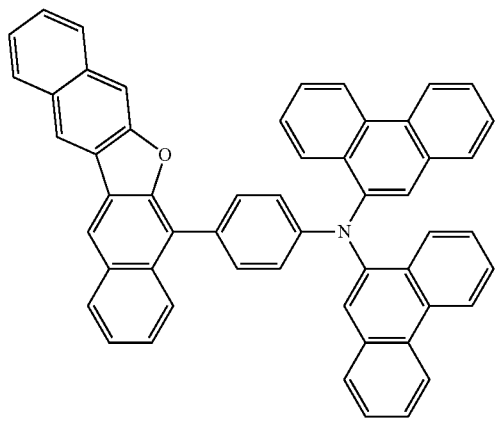
P-47
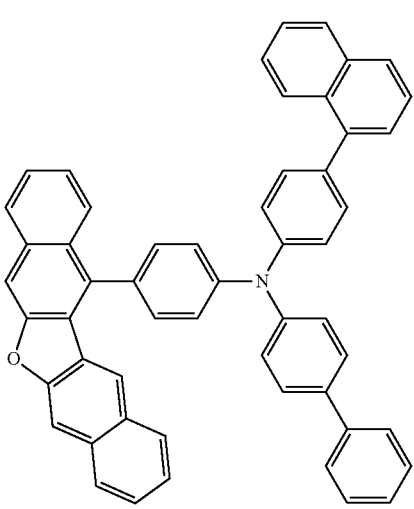
P-48
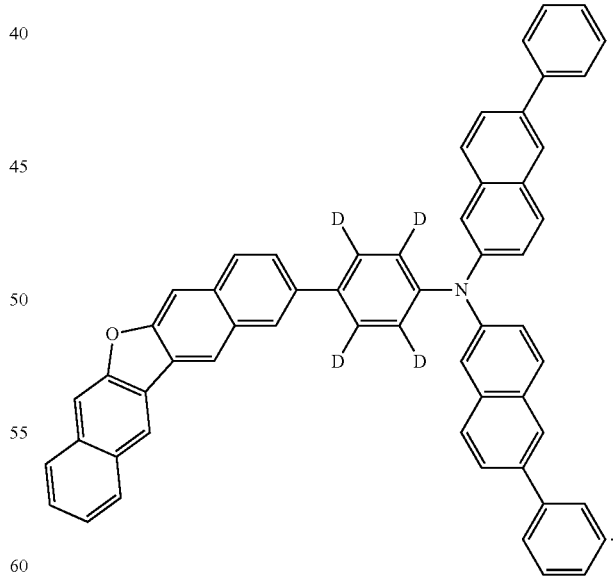
4. An organic electric element comprising a first electrode, a second electrode, and an organic material layer formed between the first electrode and the second electrode, wherein the organic material layer comprises the compound of claim 1.

5. The organic electric element of claim 4, wherein the compound is comprised in at least one layer of a hole injection layer, a hole transport layer, an emission-auxiliary layer, a light emitting layer, an electron transport-auxiliary layer, an electron transport layer and an electron injection layer.

6. The organic electric element of claim 4, wherein the organic material layer is formed by any one of the processes of spin coating, nozzle printing, inkjet printing, slot coating, dip coating or roll-to-roll.

7. An electronic device comprising a display device and a control unit for driving the display device, wherein the display device comprises the organic electric element of claim 4.

8. The electronic device of claim 7, wherein the organic electric element is an organic light emitting diode, an organic solar cell, an organic photo conductor, an organic transistor, or an element for monochromatic or white illumination.

9. An organic electric element comprising a first electrode, a second electrode, and an organic material layer formed between the first electrode and the second electrode, wherein the organic material layer comprises the compound of claim 3.

10. An electronic device comprising a display device and a control unit for driving the display device, wherein the display device comprises the organic electric element of claim 9.

11. An organic electric element comprising a first electrode, a second electrode, and an organic material layer formed between the first electrode and the second electrode, wherein the organic material layer comprises the compound of claim 2.

12. An electronic device comprising a display device and a control unit for driving the display device, wherein the display device comprises the organic electric element of claim 11.

* * * * *